(12) United States Patent
Tehrani et al.

(10) Patent No.: US 12,171,555 B2
(45) Date of Patent: *Dec. 24, 2024

(54) WEARABLE, NON-INTRUSIVE MICRONEEDLE SENSOR

(71) Applicant: The Regents of the University of California, Oakland, CA (US)

(72) Inventors: Farshad Tehrani, San Diego, CA (US);
Joseph Wang, San Diego, CA (US);
Hazhir Teymourian, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/407,265

(22) Filed: Jan. 8, 2024

(65) Prior Publication Data
US 2024/0180459 A1 Jun. 6, 2024

Related U.S. Application Data

(63) Continuation of application No. 18/313,168, filed on May 5, 2023, now Pat. No. 11,877,846, which is a
(Continued)

(51) Int. Cl.
*A61B 5/1473* (2006.01)
*A61B 5/00* (2006.01)

(52) U.S. Cl.
CPC ........ *A61B 5/14735* (2013.01); *A61B 5/0022* (2013.01); *A61B 5/685* (2013.01); *A61B 2562/046* (2013.01); *A61B 2562/125* (2013.01)

(58) Field of Classification Search
CPC . A61B 5/685; A61B 5/14532; A61B 5/14514; A61B 2562/125;
(Continued)

(56) References Cited

U.S. PATENT DOCUMENTS 4,969,468 A 11/1990 Byers et al.
6,312,612 B1 11/2001 Sherman et al.
(Continued)

FOREIGN PATENT DOCUMENTS

AU 2004200303 A1 2/2004
CN 108404286 A 8/2018
(Continued)

OTHER PUBLICATIONS

Gowers, S. et al. Development of a Minimally Invasive Microneedle-Based Sensor for Continuous Monitoring of B-Lactam Antibiotic Concentrations in Vivo. ACS Publications, 1072-1080 (2019).
(Continued)

*Primary Examiner* — Eric J Messersmith
(74) *Attorney, Agent, or Firm* — Perkins Coie LLP

(57) ABSTRACT

Disclosed here are devices, systems, and methods for continuous monitoring of biomarkers using a wearable, non-intrusive microneedle sensor patch platform. In some aspects, a wearable, non-intrusive microneedle sensor device includes a microneedle sensor unit couplable to an electronics unit, where the microneedle sensor unit comprises a substrate, an array of spiked microneedle structures configured as electrochemical sensor electrodes, an array of base structures that encase a lower portion of spiked microneedle structures, and electrical interconnections that electrically couple the electrodes to the electronics unit for processing of detectable signals associated with one or multiple biomarkers in a biofluid.

18 Claims, 55 Drawing Sheets

Related U.S. Application Data continuation of application No. 17/860,070, filed on Jul. 7, 2022, now Pat. No. 11,684,298.

(60) Provisional application No. 63/219,325, filed on Jul. 7, 2021.

(58) Field of Classification Search
CPC ........ A61B 2562/046; A61B 5/150984; A61B 5/150022; A61B 5/150969; A61B 5/14503; A61B 5/150282; A61B 5/1451
See application file for complete search history.

(56) References Cited

U.S. PATENT DOCUMENTS

| | | | |
|---|---|---|---|
| 6,611,707 | B1 | 8/2003 | Prausnitz et al. |
| 7,785,301 | B2 | 8/2010 | Yuzhakov et al. |
| 8,088,321 | B2 | 1/2012 | Ferguson et al. |
| 8,506,529 | B1* | 8/2013 | Yang ................. A61B 5/14514 604/114 |
| 8,708,966 | B2 | 4/2014 | Allen et al. |
| 8,986,256 | B2 | 3/2015 | Scholten et al. |
| 9,008,745 | B2 | 4/2015 | Pushpala et al. |
| 9,182,368 | B2 | 11/2015 | Pushpala et al. |
| 9,743,870 | B2 | 8/2017 | Wang et al. |
| 9,933,387 | B1 | 4/2018 | McCanna et al. |
| 10,034,636 | B2 | 7/2018 | Huang |
| 10,092,207 | B1 | 10/2018 | Windmiller |
| 10,492,708 | B1 | 12/2019 | Windmiller |
| 10,524,730 | B2 | 1/2020 | Reitz et al. |
| 10,549,080 | B2 | 2/2020 | Pushpala et al. |
| 10,820,860 | B2 | 11/2020 | Pushpala et al. |
| 10,835,163 | B2 | 11/2020 | Haghgooie et al. |
| 11,045,142 | B1 | 6/2021 | Windmiller et al. |
| 11,172,851 | B2 | 11/2021 | Pushpala et al. |
| 11,272,866 | B2 | 3/2022 | Pushpala et al. |
| 11,478,194 | B2 | 10/2022 | Windmiller et al. |
| 2003/0078549 | A1 | 4/2003 | Stupar et al. |
| 2005/0013753 | A1 | 1/2005 | Eaton et al. |
| 2009/0062752 | A1 | 3/2009 | Gonnelli |
| 2011/0237925 | A1 | 9/2011 | Yue et al. |
| 2013/0197338 | A1 | 8/2013 | Yu et al. |
| 2016/0029966 | A1 | 2/2016 | Salas-Boni et al. |
| 2016/0166184 | A1 | 6/2016 | Teng et al. |
| 2017/0007813 | A1 | 1/2017 | Negi et al. |
| 2017/0128009 | A1 | 5/2017 | Pushpala et al. |
| 2017/0164881 | A1 | 6/2017 | Fujita et al. |
| 2018/0338712 | A1 | 11/2018 | Cass et al. |
| 2019/0001108 | A1 | 1/2019 | Ono |
| 2019/0125223 | A1 | 5/2019 | Wang et al. |
| 2019/0240469 | A1 | 8/2019 | McAllister et al. |
| 2019/0309433 | A1 | 10/2019 | Sattayasamitsathit et al. |
| 2019/0358441 | A1 | 11/2019 | Zvezdin |
| 2020/0085341 | A1 | 3/2020 | Windmiller |
| 2020/0101286 | A1 | 4/2020 | Windmiller et al. |
| 2020/0138343 | A1 | 5/2020 | Gerasopoulos et al. |
| 2020/0254240 | A1 | 8/2020 | Windmiller et al. |
| 2020/0297997 | A1 | 9/2020 | Windmiller et al. |
| 2021/0060322 | A1 | 3/2021 | Burton |
| 2021/0100504 | A1 | 4/2021 | Pushpala et al. |
| 2021/0187286 | A1 | 6/2021 | Windmiller et al. |
| 2021/0379370 | A1 | 12/2021 | Windmiller et al. |
| 2021/0393201 | A1 | 12/2021 | Morelock et al. |
| 2022/0054813 | A1 | 2/2022 | Pushpala et al. |
| 2022/0087610 | A1 | 3/2022 | Pushpala et al. |
| 2022/0151518 | A1 | 5/2022 | Pushpala et al. |
| 2022/0370011 | A1* | 11/2022 | Windmiller ........ A61B 5/14532 |
| 2023/0099617 | A1* | 3/2023 | Mansfield, III ... A61M 37/0015 |

FOREIGN PATENT DOCUMENTS

| | | |
|---|---|---|
| CN | 211 357 412 | 8/2020 |
| CN | 113352654 A | 9/2021 |
| CN | 113648529 A | 11/2021 |
| CN | 114010934 A | 2/2022 |
| CN | 114129503 A | 3/2022 |
| DE | 102008048984 A1 | 4/2010 |
| EP | 1377338 A2 | 1/2004 |
| EP | 2359885 A1 | 8/2011 |
| EP | 2898821 A1 | 7/2015 |
| EP | 3285851 A1 | 2/2018 |
| FR | 3099696 A1 | 2/2021 |
| JP | 5053330 B2 | 10/2012 |
| KR | 100793615 B1 | 1/2008 |
| KR | 20080074058 A | 8/2008 |
| KR | 101621945 B1 | 5/2016 |
| WO | 2016/009228 A1 | 1/2016 |
| WO | 2020/186118 A1 | 9/2020 |
| WO | 2021007344 A1 | 1/2021 |
| WO | 2021/081456 A1 | 4/2021 |
| WO | 2021/119546 A1 | 6/2021 |
| WO | 2021/216186 A2 | 10/2021 |
| WO | 2021216744 A2 | 10/2021 |
| WO | 2022/170283 A1 | 8/2022 |

OTHER PUBLICATIONS

Ingrole, R. et al. Trends of microneedle technology in the scientific literature, patents, clinical trials and internet activity. Biomaterials 267, 1-24 (2021).

Jiang, X. et al. Microneedle-based skin patch for blood-free rapid diagnostic testing. Microsystems and Nanoengineering, 1-11 (2020).

Jina, A. et al. Design, Development, and Evaluation of a Novel Microneedle Array-based Continuous Glucose Monitor, Journal of Diabetes Science and Technology, vol. 8(3), 483-487 (2014).

Kathuria, H. et al. Polymeric Microneedle Array Fabrication by Photolithography. Journal of Visualized Experiments, vol. 105, 1-8 (2015).

Khezrian, S. et al. Label-free electrochemical IgE aptasensor based on covalent attachment of aptamer onto multiwalled carbon nanotubes/ionic liquid/chitosan nanocomposite modified electrode. Biosensors and Bioelectronics, vol. 43, 218-225 (2013).

Kim, J. et al. Simultaneous Monitoring of Sweat and Interstitial Fluid Using a Single Wearable Biosensor Platform, Advanced Science, 1-11 (2018).

Kolluru, C. et al. Recruitment and Collection of Dermal Interstitial Fluid Using a Microneedle Patch, Adv. Healthc Mater, 1-19 (2019).

Kolluru, C. et al. Monitoring drug pharmacokinetics and immunologic biomarkers in dermal interstitial fluid using a microneedle patch, Biomed Microdevices, vol. 21(1), 1-16 (2020).

Lee, S.J. et al. A patch type non-enzymatic biosensor based on 3D SUS micro-needle electrode array for minimally invasive continuous glucose monitoring, Sensors and Actuators B: Chemical, 1144-1151 (2016).

Liu, G. et al. Microneedles for transdermal diagnostics: Recent advances and new horizons, Biomaterials, 1-16 (2020).

Ribet, F. et al. Real-time intradermal continuous glucose monitoring using a minimally invasive microneedle-based system, Biomedical Microdevices, 1-10 (2018).

Shao, Y. et al. Recent advances in solid-contact ion-selective electrodes: functional materials, transduction mechanisms, and development trends, Chem. Soc. Rev. 4405-4465 (2020).

Sharma, S. et al. Evaluation of a minimally invasive glucose biosensor for continuous tissue monitoring, Anal Bioanal Chem, 8427-8435 (2016).

Sharma, S. et al. Rapid, low cost prototyping of transdermal devices for personal healthcare monitoring, Sens Biosensing Res. 104-108 (2017).

Sharma, S. et al. A pilot study in humans of microneedle sensor arrays for continuous glucose monitoring, Analytical Methods, 2088-2095 (2018).

Takeuchi, K. et al. Functionalized microneedles for continuous glucose monitoring, Nano Convergence, 1-10 (2018).

Tasca, F. et al. Microneedle-based electrochemical devices for transdermal biosensing: a review, Electrochemistry, 42-49 (2019).

Tehrani, F. et al. An integrated wearable microneedle array for the continuous monitoring of multiple biomarkers in interstitial fluid, Nature Biomedical Engineering, 1-14 (2021).

Teymourian, H. et al. Closing the loop for patients with Parkinson

(56) References Cited

OTHER PUBLICATIONS disease: where are we?, Nature Reviews| Neurology, 1-11 (2022).
Teymourian, H. et al. Wearable Electrochemical Sensors for the Monitoring and Screening of Drugs, ACS Sensors, vol. 5, 2679-2700 (2020).
Al Sulaiman, D. et al. Hydrogel-Coated Microneedle Arrays for Minimally Invasive Sampling and Sensing of Specific Circulating Nucleic Acids from Skin Interstitial Fluid, ACS Nano, vol. 13, 9620-9628 (2019).
Arroyo-Currás, N. et al. Real-time measurement of small molecules directly in awake, ambulatory animals, PNAS, vol. 114(4), 645-650 (2017).
Babity, S. et al. Advances in the Design of Transdermal Microneedles for Diagnostic and Monitoring Applications, Advanced Science News, vol. 14, 1-16 (2018).
Bollella, P. et al. Microneedle-based biosensor for minimally-invasive lactate detection, Biosensors and Bioelectronics, vol. 123, 152-159 (2019).
Bollella, P. et al. Minimally Invasive Glucose Monitoring Using a Highly Porous Gold Microneedles-Based Biosensor: Characterization and Application in Artificial Interstitial Fluid, Catalysts, vol. 9, 1-14, (2019).
Campbell, A. et al. Wearable Electrochemical Alcohol Biosensors, Curr Opin Electrochem, 1-17 (2018).
Chinnadayyala, S. et al. Review—In Vivo and In Vitro Microneedle Based Enzymatic and Non-Enzymatic Continuous Glucose Monitoring Biosensors. ECS Journal of Solid State Science and Technology, vol. 7, Q3159-Q3171 (2018).
Ciui, B. et al. Wearable Wireless Tyrosinase Bandage and Microneedle Sensors: Toward Melanoma Screening. Advanced Healthcare Materials, 1-9 (2018).
El-Laboudi, A. et al. Use of Microneedle Array Devices for Continuous Glucose Monitoring: A Review. Diabetes Technology & Therapeutics, vol. 15(1), 101-115 (2013).
Garcia-López, E. et al. Study of the fabrication of AISI 316L microneedle arrays. Science Direct, Procedia Manufacturing vol. 26, 117-124 (2018).
Goud, K. et al. Wearable Electrochemical Microneedle Sensor for Continuous Monitoring of Levodopa: Toward Parkinson Management. ACS Sensors, vol. 4, 2196-2204 (2019).
Madden, J. et al. Biosensing in dermal interstitial fluid using microneedle based electrochemical devices. Sensing and Bio-Sensing Research, vol. 29, 1-17 (2020).
Menon, I. et al. Microneedles: A New Generation Vaccine Delivery System. Micromachines. 1-18 (2021).
Miller, P. et al. Multiplexed microneedle-based biosensor array for characterization of metabolic acidosis. Talanta, vol. 88. 739-742 (2012).
Miller, P. et al. Microneedle-based sensors for medical diagnosis. Journals of Materials Chemistry B, vol. 4, No. 8, 6 pages (2016).
Miller, P. et al. Extraction and biomolecular analysis of dermal interstitial fluid collected with hollow microneedles. Communications Biology. 1-11 (2018).
Min, J. et al. Wearable electrochemical biosensors in North America. Biosensors and Bioelectronics, vol. 172, 1-16 (2021).
Mishra, R. et al. A microneedle biosensor for minimally-invasive transdermal detection of nerve agents. Royal Society of Chemistry. 918-924 (2017).
Mishra, R. et al. Continuous Opioid Monitoring along with Nerve Agents on a Wearable Microneedle Sensor Array. Journal of the American Chemical Society, vol. 142, 5991-5995 (2020).
Mohan, A.M. et al. Continuous minimally-invasive alcohol monitoring using microneedle sensor arrays. Biosensors and Bioelectronics, vol. 91, 574-579 (2017).
Ruiz-Valdepeñas Montiel, V. et al. Delayed Sensor Activation Based on Transient Coatings: Biofouling Protection in Complex Biofluids. Journal of the American Chemical Society. vol. 140, 14050-14053 (2018).
Parrilla, M. et al. Wearable All-Solid-State Potentiometric Microneedle Patch for Intradermal Potassium Detection. Analytical Chemistry, vol. 91, 1578-1586 (2019).
Rawson, T. et al. Towards a minimally invasive device for beta-lactam monitoring in humans. Electrochem commun. 1-12 (2017).
Tu, J. et al. The Era of Digital Health: A Review of Portable and Wearable Affinity Biosensors. Advanced Functional Materials. 1-30 (2019).
Valdés-Ramírez, G et al. Microneedle-based self-powered glucose sensor. Electrochemistry Communications, vol. 47, 58-62 (2014).
Vargas, E. et al. Enzymatic/Immunoassay Dual-Biomarker Sensing Chip: Towards Decentralized Insulin/Glucose Detection. Angew. Chem. Int. Ed. 6376-6379 (2019).
Ventrelli, L. et al. Microneedles for Transdermal Biosensing: Current Picture and Future Direction. Advanced Healthcare Materials. 2606-2640 (2015).
Venugopal, M. et al. Clinical Evaluation of a Novel Interstitial Fluid Sensor System for Remote Continuous Alcohol Monitoring. IEEE Sensors Journal, vol. 8, No. 1, 71-80 (2008).
Wang, J. Electrochemical Glucose Biosensors. Chem. Rev. vol. 108, 814-825 (2008).
Wang, F. et al. Living Bacterial Microneedles for Fungal Infection Treatment. Research Article, vol. 2020, 1-9 (2020).
Wang, M. et al. Recent advances in the design of polymeric microneedles for transdermal drug delivery and biosensing. Lab on a Chip, vol. 17, 1373-1387 (2017).
Wang, Z. et al. Microneedle patch for the ultrasensitive quantification of protein biomarkers in interstitial fluid. Nature Biomedical Engineering, vol. 5, 64-76 (2021).
Windmiller J.R. et al. Bicomponent Microneedle Array Biosensor for Minimally-Invasive Glutamate Monitoring. Electroanalysis, vol. 23, 2302-2309 (2011).
Windmiller, J.R. et al. Microneedle array-based carbon paste amperometric sensors and biosensors. Analyst, vol. 136, 1846-1851 (2011).
Xie, L. et al. Engineering Microneedles for Therapy and Diagnosis: A Survey. Micromachines. 1-28 (2020).
Yáñez-Sedeño, P. et al. Multiplexed Electrochemical Immunosensors for Clinical Biomarkers. Sensors, vol. 17, 1-30 (2017).
Yang, B. et al. In Situ Sampling and Monitoring Cell-Free DNA of the Epstein-Barr Virus from Dermal Interstitial Fluid Using Wearable Microneedle Patches. ACS Applied Materials & Interfaces, vol. 11, 38448-38458 (2019).
Zhang, B.L. et al. Microneedle-assisted technology for minimally invasive medical sensing. Microchemical Journal, vol. 162, 1-12 (2021).
Zhang, X. et al. Encoded Microneedle Arrays for Detection of Skin Interstitial Fluid Biomarkers. Advanced Materials, vol. 31, 1-8 (2019).
Zhang, X. et al. Bio-inspired clamping microneedle arrays from flexible ferrofluid-configured moldings. Science Bulletin, vol. 64, 1110-1117 (2019).
Tran, B. Q. et al. Proteomic Characterization of Dermal Interstitial Fluid Extracted Using a Novel Microneedle-Assisted Technique. Journal of Proteome Research, vol. 17, 479-485 (2018).
Teymourian, H. et al. Electrochemical glucose sensors in diabetes management: an updated review (2010-2020). Royal Society of Chemistry, Chem. Soc. Rev., vol. 49, 7671-7709 (2020).
Teymourian, H. et al. Microneedle-Based Detection of Ketone Bodies along with Glucose and Lactate: Toward Real-Time Continuous Interstitial Fluid Monitoring of Diabetic Ketosis and Ketoacidosis. Anal. Chem., vol. 92, 2291-2300 (2020).
ISA, International Search Report and Written Opinion for PCT Application No. PCT/US2020/036424. Mail Date: Oct. 14, 2022. 13 pages.
Bandodkar, A. J. et al. Non-invasive wearable electrochemical sensors: a review. Trends Biotechnol. 32, 363-371 (2014).
Bandodkar, A. J. et al. Battery-free, skin-interfaced microfluidic/electronic systems for simultaneous electrochemical, colorimetric, and volumetric analysis of sweat. Sci. Adv. 5, eaav3294 (2019).
Bandodkar, A. J. et al. Tattoo-Based Noninvasive Glucose Monitoring: A Proof-of-Concept Study. Anal. Chem. 87, 394-398 (2015).

(56) References Cited

OTHER PUBLICATIONS

Brothers, M. C. et al. Achievements and Challenges for Real-Time Sensing of Analytes in Sweat within Wearable Platforms. Acc. Chem. Res. 52, 297-306 (2019).
Burge, M. R., et al. Continuous Glucose Monitoring: The Future of Diabetes Management. Diabetes Spectr. 21, 112 LP-119 (2008).
Choi, .J et al. Bio-Integrated Wearable Systems: A Comprehensive Review. Chem. Rev. 119, 5461-5533 (2019).
Dunn, J., et al. Wearables and the medical revolution. Per. Med. 15, 429-448 (2018).
Emaminejad, S. et al. Autonomous sweat extraction and analysis applied to cystic fibrosis and glucose monitoring using a fully integrated wearable platform. Proc. Natl. Acad. Sci. 114, 4625-4630 (2017).
Fairbairn, C. E. et al. Temporal Dynamics of Transdermal Alcohol Concentration Measured via New-Generation Wrist-Worn Biosensor. Alcohol. Clin. Exp. Res. 43, 2060-2069 (2019).
Gao, J., et al. Simultaneous detection of glucose, uric acid and cholesterol using flexible microneedle electrode array-based biosensor and multi-channel portable electrochemical analyzer. Sensors Actuators, B Chem. 287, 102-110 (2019).
Gao, W. et al. Fully integrated wearable sensor arrays for multiplexed in situ perspiration analysis. Nature 529, 509-514 (2016).
Heikenfeld, J. et al. Accessing analytes in biofluids for peripheral biochemical monitoring. Nat. Biotechnol. 37, 407-419 (2019).
Heikenfeld, J. et al. Wearable sensors: modalities, challenges, and prospects. Lab Chip 18, 217-248 (2018).
Imani, S. et al. A wearable chemical-electrophysiological hybrid biosensing system for real-time health and fitness monitoring. Nat. Commun. 7, 11650 (2016).
Jia, W. et al. Electrochemical Tattoo Biosensors for Real-Time Noninvasive Lactate Monitoring in Human Perspiration. Anal. Chem. 85, 6553-6560 (2013).
Jones, T. E. et al. Plasma lactate as a marker of metabolic health: Implications of elevated lactate for impairment of aerobic metabolism in the metabolic syndrome. Surgery 166, 861-866 (2019).
Kim, J., et al. Wearable biosensors for healthcare monitoring. Nature Biotechnology vol. 37 389-406 (2019).
Koppes, L. L. J., et al. Moderate Alcohol Consumption Lowers the Risk of Type 2 Diabetes. Diabetes Care 28, 719 LP-725 (2005).
Lee, H. et al. A graphene-based electrochemical device with thermoresponsive microneedles for diabetes monitoring and therapy. Nat. Nanotechnol. 11, 566-572 (2016).
Lee, I., et al. Continuous glucose monitoring systems—Current status and future perspectives of the flagship technologies in biosensor research—. Biosens. Bioelectron. 113054 (2021) doi:https://doi.org/10.1016/j.bios.2021.113054.
Lipani, L. et al. Non-invasive, transdermal, path-selective and specific glucose monitoring via a graphene-based platform. Nat. Nanotechnol. 13, 504-511 (2018).
Mishra, T. et al. Pre-symptomatic detection of COVID-19 from smartwatch data. Nat. Biomed. Eng. 4, 1208-1220 (2020).
Nyein, H. Y. Y. et al. Regional and correlative sweat analysis using high-throughput microfluidic sensing patches toward decoding sweat. Sci. Adv. (2019) doi:10.1126/sciadv.aaw9906.
Rawson, T. M. et al. Microneedle biosensors for real-time, minimally invasive drug monitoring of phenoxymethylpenicillin: a first-in-human evaluation in healthy volunteers. Lancet Digit. Heal. 1, e335-e343 (2019).
Rose, D. P. et al. Adhesive RFID sensor patch for monitoring of sweat electrolytes. IEEE Trans. Biomed. Eng. (2015) doi:10.1109/TBME.2014.2369991.
Sakaguchi, K. et al. Glucose area under the curve during oral glucose tolerance test as an index of glucose intolerance. Diabetol. Int. 7, 53-58 (2016).
Sakai, J. T., et al. Validity of Transdermal Alcohol Monitoring: Fixed and Self-Regulated Dosing. Alcohol. Clin. Exp. Res. 30, 26-33 (2006).
Samant, P. P. et al. Sampling interstitial fluid from human skin using a microneedle patch. Sci. Transl. Med. 12, eaaw0285 (2020).
Sempionatto, J. R. et al. An epidermal patch for the simultaneous monitoring of haemodynamic and metabolic biomarkers. Nat. Biomed. Eng. (2021) doi:10.1038/s41551-021-00685-1.
Teymourian, H. et al. Microneedle-Based Detection of Ketone Bodies along with Glucose and Lactate: Toward Real-Time Continuous Interstitial Fluid Monitoring of Diabetic Ketosis and Ketoacidosis. Anal. Chem. 92, 2291-2300 (2020).
Teymourian, H., et al. Electrochemical glucose sensors in diabetes management: an updated review (2010-2020). Chem. Soc. Rev. 49, 7671-7709 (2020).
Teymourian, H., et al. Lab under the Skin: Microneedle Based Wearable Devices. Adv. Healthc. Mater. n/a, 2002255 (2021).
Topol, E. J. High-performance medicine: the convergence of human and artificial intelligence. Nat. Med. 25, 44-56 (2019).
Tran, B. Q. et al. Proteomic Characterization of Dermal Interstitial Fluid Extracted Using a Novel Microneedle-Assisted Technique. J. Proteome Res. 17, 479-485 (2018).
Waltz, E. Sweet sensation. Nat. Biotechnol. 37, 340-344 (2019).
Wiorek, A., et al. Epidermal Patch with Glucose Biosensor: pH and Temperature Correction toward More Accurate Sweat Analysis during Sport Practice. Anal. Chem. (2020) doi:10.1021/acs.analchem.0c02211.
Wolf, A. et al. Evaluation of Continuous Lactate Monitoring Systems within a Heparinized In Vivo Porcine Model Intravenously and Subcutaneously. Biosensors vol. 8 (2018).
Wolkowicz, K. L. et al. A review of biomarkers in the context of type 1 diabetes: Biological sensing for enhanced glucose control. Bioeng. Transl. Med. 6, e10201 (2021).
World Economic Forum. Top 10 Emerging Technologies of 2020. http://www3.weforum.org/docs/WEF_Top_10_Emerging_Technologies_2020.pdf.
Yang, Y. et al. A laser-engraved wearable sensor for sensitive detection of uric acid and tyrosine in sweat. Nat. Biotechnol. (2020) doi:10.1038/s41587-019-0321-x.
Yetisen, A. K., et al. Wearables in Medicine. Adv. Mater. 30, 1706910 (2018).
Yu, G. et al. Utility of the early lactate area score as a prognostic marker for septic shock patients in the emergency department. Acute Crit Care 34, 126-132 (2019).
Zeevi, D. et al. Personalized Nutrition by Prediction of Glycemic Responses. Cell 163, 1079-1094 (2015).
EPO, Extended Search Report mailed Oct. 25, 2024 for 22838439.2, 13 pages.

* cited by examiner

FIG. 24

Microneedles geometry

Microneedle Patch (Top View)
MN Diameter: 300 μm
MN Quantity: 25
WE: 20 | CE: 4 | RE: 1

Microneedle Patch (Side View)

MN Height: 900 μm
MN Pitch: 2.4 mm

Microneedle Patch (Backside)
Electronics Contact Holes
MN Diameter: 300 μm
MN Height: 900 μm
MN Quantity: 25

WEARABLE, NON-INTRUSIVE MICRONEEDLE SENSOR

CROSS-REFERENCE TO RELATED APPLICATIONS

This patent document is a continuation of U.S. application Ser. No. 18/313,168, filed on May 5, 2023, which is a continuation of U.S. application Ser. No. 17/860,070, filed on Jul. 7, 2022, now U.S. Pat. No. 11,684,298, which claims priorities and benefits of U.S. Provisional Application No. 63/219,325, titled "WEARABLE, NON-INTRUSIVE MICRONEEDLE SENSOR" and filed on Jul. 7, 2021. The entire content of the aforementioned patent applications is incorporated by reference as part of the disclosure of this patent document.

TECHNICAL FIELD

This patent document relates to biosensor devices, systems, and methods, and particularly to microneedle sensors.

BACKGROUND

Biosensors can provide real-time detection of physiological substances and processes in living things. A biosensor is an analytical tool that can detect a chemical, substance, or organism using a biologically sensitive component coupled with a transducing element to convert a detection event into a signal for processing and/or display. Biosensors can use biological materials as the biologically sensitive component, e.g., such as biomolecules including enzymes, antibodies, nucleic acids, etc., as well as living cells. For example, molecular biosensors can be configured to use specific chemical properties or molecular recognition mechanisms to identify target agents.

SUMMARY

Disclosed here are devices, systems, and methods for reliable, accurate and continuous monitoring of ISF biomarkers using a wearable, non-intrusive spiked microneedle sensor patch platform.

In some aspects, a wearable, non-intrusive microneedle sensor device includes a microneedle sensor unit couplable to an electronics unit, where the microneedle sensor unit comprises a substrate, an array of spiked microneedle structures that include sensor electrodes, an array of base structures that encase a lower portion of spiked microneedle structures, and electrical interconnections that electrically couple the sensor electrodes to the electronics unit for processing of detectable signals associated with one or multiple biomarkers in a biofluid. In some embodiments, for example, the microneedle sensor unit includes a substrate comprising an electrically insulative material; an array of spiked microneedle structures disposed on the substrate, wherein at least some of the spiked microneedle structures are configured as electrochemical sensor electrodes to detect an electrical signal from a reaction with a target analyte in a biofluid exposed to the array of spiked microneedle structures, wherein at least one electrochemical sensor electrode is functionalized by a chemical layer to interact with the target analyte in the biofluid and produce the electrical signal at the at least one electrochemical sensor electrode, and wherein each spiked microneedle structure of the array of spiked microneedle structures includes a body region and a tip region, the body region including a cylindrical shape having a spiral protrusion that winds around at least a portion of the body region, and the tip region including a conical shape; an array of base structures comprising an electrical insulator material, wherein each base structure encases a lower portion of the body region of a corresponding spiked microneedle structure; and a plurality of electrical interconnections disposed in or on the substrate, wherein each of the electrical interconnections is coupled to one or more of the spiked microneedle structures configured as the electrochemical sensor electrodes and to a contact terminus structure on the substrate. In some embodiments, for example, the electronics unit is configured in electrical communication with the plurality of electrical interconnections, wherein the electronics unit includes a circuit board, a signal processing circuit configured on the circuit board, a power source in electrical communication with the signal processing circuit, and a plurality of conductive pins that electrically couple the microneedle sensor unit to the electronics unit by allowing contact between an elongated region of a conductive pin to the terminus region of a corresponding electrical interconnection. In some embodiments of the spiked microneedle structures, for example, the tip region of a spiked microneedle structure includes a microporous tip region with a plurality of micropores (e.g., 0.5 μm to 20 μm sized micropores). In some embodiments of the spiked microneedle structures, for example, the body region includes a cylindrical shape having at least two segments, wherein a lower segment includes the lower portion of the body region that is encased by base structure and comprises a plurality of vertically aligned microfluidic channels, and wherein an upper segment includes an upper portion of the body region where the spiral protrusion is disposed.

In some aspects, a wearable, non-intrusive microneedle sensor device includes a microneedle sensor unit and an electronics unit in electrical communication with the microneedle sensor unit. The microneedle sensor unit comprises (i) a substrate comprising an electrically insulative material, (ii) an array of spiked microneedle structures disposed on the substrate, wherein at least some of the spiked microneedle structures are configured as electrochemical sensor electrodes to detect an electrical signal from a reaction with a target analyte in a biofluid exposed to the array of spiked microneedle structures, wherein at least one electrochemical sensor electrode is functionalized by a chemical layer to interact with the target analyte in the biofluid and produce the electrical signal at the at least one electrochemical sensor electrode, and wherein each spiked microneedle structure of the array of spiked microneedle structures includes a body region and a tip region, the body region including a cylindrical shape having a spiral protrusion that winds around at least a portion of the body region, and the tip region including a conical shape, (iii) an array of base structures comprising an electrical insulator material, wherein each base structure encases a lower portion of the body region of a corresponding spiked microneedle structure, and (iv) a plurality of electrical interconnections disposed in or on the substrate, wherein each of the electrical interconnections is coupled to one or more of the spiked microneedle structures configured as the electrochemical sensor electrodes and to a contact terminus structure on the substrate. The electronics unit is in electrical communication with the plurality of electrical interconnections, and the electronics unit comprises a circuit board, a signal processing circuit configured on the circuit board, a power source in electrical communication with the signal processing circuit, and a plurality of conductive pins that electrically couple the microneedle sensor unit to the electronics unit by allowing contact between an elongated region of a conductive pin to the terminus region of a corresponding electrical interconnection.

In some aspects, a wearable, non-intrusive microneedle sensor device includes a microneedle sensor unit and an electronics unit in electrical communication with the microneedle sensor unit. The microneedle sensor unit comprises (i) a substrate comprising an electrically insulative material, and (ii) an array of microneedle structures disposed on the substrate and comprising a body region and a tip region, wherein the body region includes a protrusion that winds around at least an upper portion of the body region, wherein at least some of the microneedle structures are configured as electrochemical sensor electrodes to detect an electrical signal from a reaction with a target analyte in a biofluid exposed to the array of microneedle structures, wherein at least one electrochemical sensor electrode is functionalized by a chemical layer to interact with the target analyte in the biofluid and produce the electrical signal at the at least one electrochemical sensor electrode. The electronics unit is in electrical communication with the microneedle sensor unit, and the electronics unit comprises a circuit board, and a plurality of conductive pins that electrically couple the microneedle sensor unit to the circuit board of the electronics unit by allowing contact between an elongated region of a conductive pin to an electrically conductive portion of the microneedle sensor unit.

In some aspects, a wearable, non-intrusive microneedle sensor patch device includes a substrate comprising an electrically insulative material, and an array of microneedle structures disposed on the substrate and comprising a body region and a tip region, wherein the body region includes a protrusion that winds around at least an upper portion of the body region, wherein at least some of the microneedle structures are configured as electrochemical sensor electrodes to detect an electrical signal from a reaction with a target analyte in a biofluid exposed to the array of microneedle structures, wherein at least one electrochemical sensor electrode is functionalized by a chemical layer to interact with the target analyte in the biofluid and produce the electrical signal at the at least one electrochemical sensor electrode.

In some aspects, a method for fabricating a wearable, non-intrusive microneedle sensor device includes creating or obtaining a computer-aided design of a microneedle sensor array comprising a plurality of microneedle structures arranged on a substrate, wherein the plurality of microneedle structures includes a body region, a tip region, a protrusion that winds around at least an upper portion of the body region; producing a physical rendition of the microneedle sensor array, wherein at least some of the plurality of microneedle structures of the produced physical rendition of the microneedle sensor array include an electrically-conductive region to form microelectrodes of the at least some of the plurality of microneedle structures; and attaching a cover to the physical rendition of the microneedle sensor array, the cover comprising an electrically insulative material having a plurality of openings configured to align with the plurality of microneedle structures on the substrate, such that the tip region and at least a distal portion of the body region of the microneedle structures pass through the openings of the cover.

The subject matter described in this patent document can be implemented in specific ways that provide one or more of the following features.

DETAILED DESCRIPTION

Figure 1A:
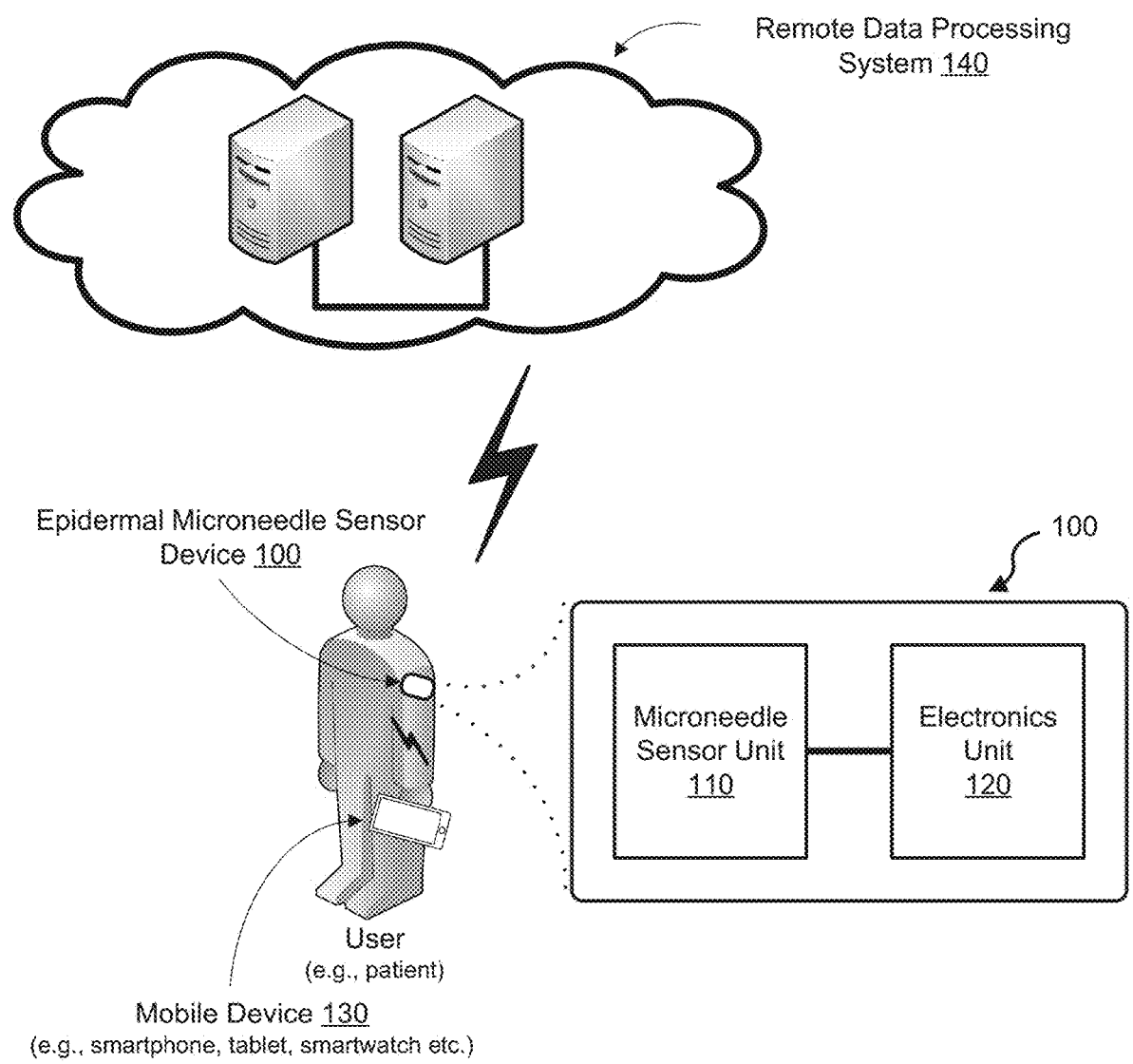
FIGS. 1A-1F show diagrams and images depicting an example embodiment of a wearable, non-intrusive epidermal microneedle array sensor platform, in accordance with the present technology.

The development of wearable chemical sensors has continued to advance over the past several years with the aim of providing users with real-time insight into the physiological state of biological system(s) at a molecular level. Notably, the class of wearable, semi-invasive chemical sensors, such as transdermal sensors for continuous glucose monitoring (CGM), has been tremendously successful in providing patients with critical information about their blood glucose levels in real-time. Yet, there has been great efforts toward the development of wearable, non-invasive epidermal sensors, which have the potential to provide the same level as accuracy in analyte sensing as invasive or semi-invasive sensors, but without the negative attributes of pain, restrictions, and other limits on patient users.

To date, wearable, non-invasive epidermal sensors have solely relied on extracted sweat and/or reverse iontophoresis induced Interstitial Fluid (ISF) as their sensing biofluids. However, in spite of the numerous proof-of-concept demonstrations throughout the past decade, non-invasive epidermal sensors still confront grand challenges to transcend from the benchtop to the body, as an approved medical device. Particularly, these challenges include the lack of spontaneous excretion (and thus accessibility) of the user's biofluid in a continuous manner and the reliability of the sensor's detectable signal (especially upon a fluctuating biofluid's flow rate). Yet, even further, conventional wearable non-invasive epidermal sensor devices lack effective techniques to mitigate problems that can commonly occur in real-world use of a continuous chemical sensor, such as users' varying skin parameters (e.g., such as pH and temperature), lack of natural biofluid replenishment, sample contamination of the analyzed biofluid, and dilution of the biofluid, as well as the unestablished analyte correlation between both biofluids and the blood among conventional sensor platforms. Consequently, the present state of non-intrusive, epidermal chemical sensors has been confined within the boundaries of mere conceptual demonstrations in the research community.

Disclosed here are devices, systems, and methods for reliable, accurate and continuous monitoring of ISF biomarkers using a wearable, non-intrusive spiked microneedle sensor patch platform. Example embodiments of a wearable, non-intrusive spiked microneedle sensor patch device, system, and method are shown and discussed, including through example implementations for continuous monitoring of glucose, lactate, alcohol, ketone bodies, and salt ions as model ISF biomarker analytes, both individually and simultaneously, with the results well correlated against standard meters for each analyte in a prolonged period of time.

The disclosed non-intrusive spiked microneedle sensor technology includes an array of microscale spiked needle structures disposed on a substrate that can be positioned on a user's skin such that the spiked microneedles of the array reach only a few microns beneath the skin surface, e.g., thus eliminating the experience of pain and/or discomfort for the wearer. Herein, a "spiked microneedle" is a protrusion structure having an extending body culminating at a tip at a terminal end, where the extending body may vary in shape and size (e.g., depending on a desired application), and the tip has a terminal apex and vary in shape and size. Various embodiments of a spiked microneedle disclosed herein include a projection structure that winds around at least a portion of the extending body, which can be configured as a spiral from the body-tip interface toward the base of the extending body. Various embodiments of a spiked microneedle disclosed herein include the extending body configured in a cylindrical shape and the tip configured in a conical shape, but it is understood that the extending body and/or the tip can be configured in other shapes; for example, the tip can be configured in various pyramidal shapes (e.g., triangular pyramidal, rectangular pyramidal, pentagonal pyramidal, etc.). Notably, the structural design of the disclosed spiked microneedle sensor technology eliminates the need for the conventional (invasive) centimeter-long needle sensor in existing CGM sensors (e.g., which typically can range from 5 mm to 11 mm, reaching the subcutaneous fat tissue). Moreover, the micron-scale nature of the disclosed spiked microneedle sensors allows for their application on multiple locations of the body, e.g., making it adaptable to different form factors such as a ring, earrings, or an epidermal patch. Furthermore, the disclosed spiked microneedle sensor technology provides physically isolated and independently operating multiplexed microneedle arrays on a single platform, overcoming the limiting single-analyte sensing capability of the current CGM devices.

While the disclosed embodiments and implementations are described herein primarily based on electrochemical monitoring of one or more analytes in Interstitial Fluid (such as glucose, lactate, alcohol, ketone bodies, and sodium) to facilitate understanding of the underlying concepts of the present technology, it is understood that the disclosed embodiments can also include monitoring of other analytes and/or biofluids associated with other tissues, organs and organ systems.

EXAMPLE EMBODIMENTS

FIGS. 1A-1F show diagrams and images depicting an example embodiment of a wearable, non-intrusive epidermal microneedle array sensor platform, in accordance with the present technology, for continuous, real-time measurements of one or multiple analyte(s) from the ISF of a user.

FIG. 1A shows a diagram illustrating a wearable, non-intrusive microneedle sensor patch device 100, in accordance with the present technology, which is in wireless communication with a mobile device 130, e.g., such as a smartphone, tablet, smartwatch, and/or other portable computing and/or communication device. The microneedle sensor patch device 100 includes a microneedle sensor contingent (unit) 110 in electrical communication with electronics contingent (unit) 120, discussed in further detail below. The mobile device 130 includes a software application ("app") in accordance with some embodiments of the present technology that is configured to manage data processing and/or display of analyte data acquired by the microneedle sensor patch device 100 and provide a user interface for a user (e.g., patient) wearing the microneedle sensor patch device 100. In some embodiments, the user interface of the app can display data, e.g., such as present and/or past analyte values detected by the microneedle sensor patch device 100, allow a user to input data associated with the user's health for time points of the analyte data, and/or implement a control or function of the sensor patch device 100.

Also, as illustrated in the diagram of FIG. 1A, in some optional embodiments, the microneedle sensor patch device 100 is in communication with a remote data processing system 140 including one or more computers in a network of computers (e.g., the cloud) that communicates with the mobile device 130 and/or the microneedle sensor patch device 100, where data from the microneedle sensor patch device 100 and/or mobile device 130 is transferred to the remote data processing system 140. Similarly, data from the remote data processing system 140 can transfer data to the mobile device 130 (e.g., for use by the app resident on the mobile device 130) and/or the microneedle sensor patch device 100. In some implementations, the remote data processing system 140 can remotely monitor data associated with the user obtained by the microneedle sensor patch device 100 and/or remotely operate aspects of the platform, e.g., such as modify sensing parameters or protocols of the device 100, data display or processing features of the app on the mobile device 130, or other. In various embodiments, for example, the remote data processing system 140 can include a personal computer such as a desktop or laptop computer, a mobile computing device such as a smartphone, tablet, smartwatch, etc., or other computing device.

Figure 1B:
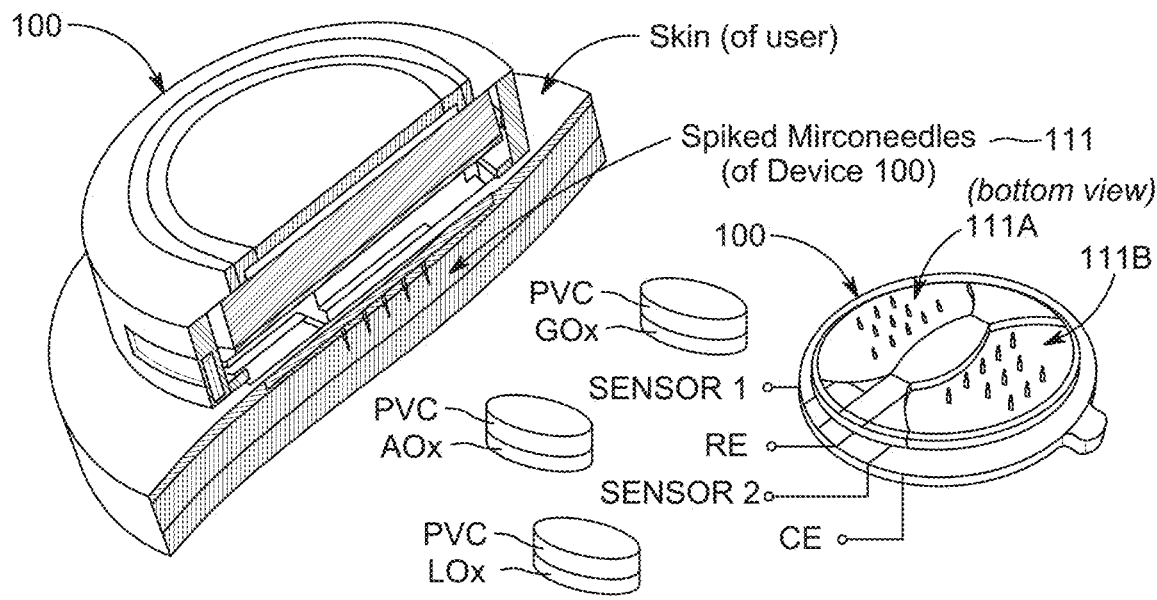
Figure 1B:
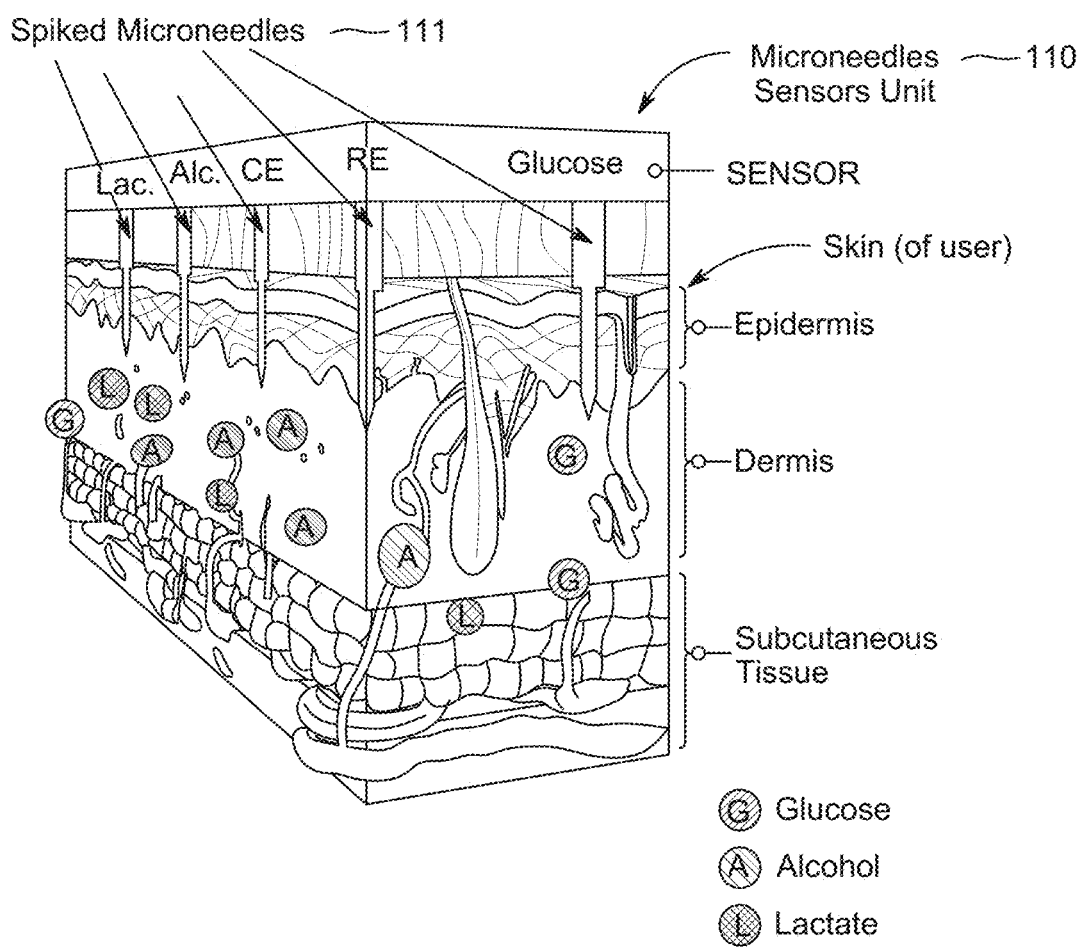

FIG. 1B shows diagrams illustrating an example embodiment of the wearable, non-intrusive microneedle sensor patch device 100 of FIG. 1A. The left diagram of FIG. 1B illustrates the example microneedle sensor patch device 100 including the electronics unit 120 coupled to the microneedle sensor unit 110, which includes an array of spiked microneedles 111 that protrude outward of the device 100 so as to minimally puncture the epidermis layer of skin of the patient user and operate as electrochemical or electrophysiological electrodes for various epidermal sensing applications. The right diagram of FIG. 1B illustrates a bottom view of the example microneedle sensor patch device 100, showing an example of the device 100 having (i) two sensors (sensor 1 and sensor 2) configured to sense two distinct analytes via two arrays of spiked microneedle sensors 111A and 111B providing working (detecting) electrodes, and (ii) one or more reference electrodes ("RE") and (iii) one or more counter electrodes ("CE"). In this example, sensor 1 is configured to detect glucose, and sensor 2 is configured to detect lactate. The lower diagram of FIG. 1B illustrates the example microneedle sensor patch device 100 in a cross-sectional illustration where the spiked microneedles 111 are shown penetrating the skin (image is not to scale). As shown, the spiked microneedles 111 extend through the epidermis layer of the skin, with the tips of the spiked microneedles 111 penetrating in a shallow region of the dermis layer and not into the subcutaneous tissue underneath.

Figure 1C:
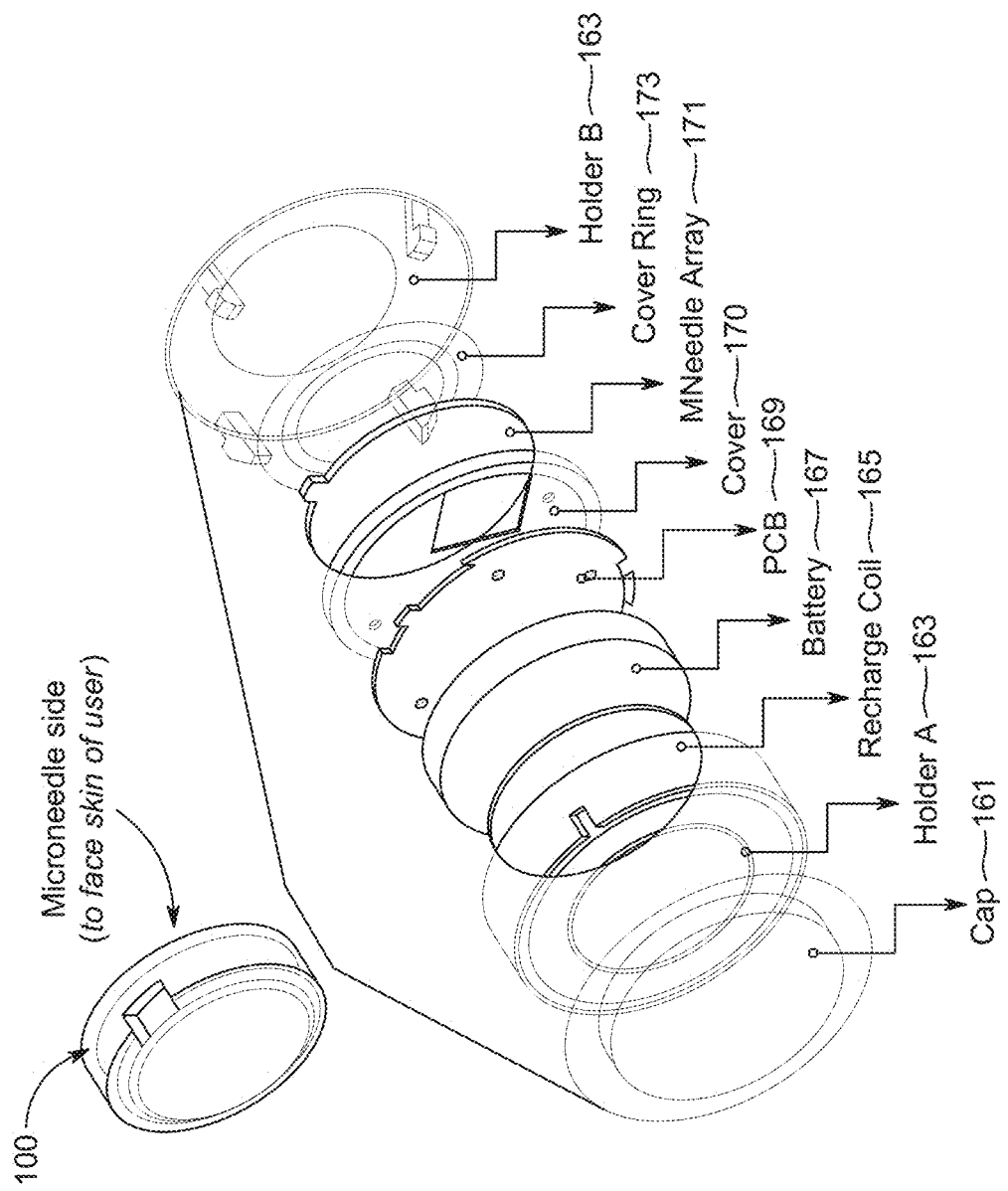

FIG. 1C shows a diagram illustrating an exploded view of the example embodiment of the wearable, non-intrusive microneedle sensor patch device 100 shown in FIG. 1B. In this example embodiment, the microneedle sensor patch device 100 can include distinct sub-components, including, which are assembled into two primary components, i.e., a disposable sensor component 110C and a reusable electronics unit 120C. Overall, these distinct sub-components of the microneedle sensor patch device 100 include an outer cap 161, a holder or encasement 163 (which can include one or more housing components, e.g., shown here as holder A and holder B), a recharge coil 165, a power supply 167 (e.g., a battery), an electronics interface board 169 (e.g., printed circuit board (PCB)), a substrate providing an array of spiked microneedles (e.g., "spiked microneedle array substrate" 171), a separation cover 170 to (optionally) sit between the electronics interface board 169 and the spiked microneedle array substrate 171, and a cover ring 173 for the spiked microneedle array substrate 171. This modular design of the microneedle sensor patch device 100 allows convenient replacement of the low-cost disposable sensor component, e.g., according to its functional life, while preserving and reusing the electronics unit 120. In example implementations of the microneedle sensor patch device 100 including the disposable sensor component 110C and the reusable electronics unit 120C, for example, after use, the holder B 163 can be separated from the holder A 163, such that the used spiked microneedle array substrate 171 can be removed from the device 100 and disposed and a new spiked microneedle array substrate 171 can be inserted into the device 100 and interfaced with the electronic interface board 169 of the reusable electronics unit 120C for the next use of the device 100. In some implementations, for example, the cover ring 173 is also disposable with the used spiked microneedle array substrate 171 (e.g., the cover ring 173 and the spiked microneedle array substrate 171 may be affixed in some embodiments), such that a new cover ring 173 is attached or comes affixed to a new spiked microneedle array substrate 171.

Figure 1D:
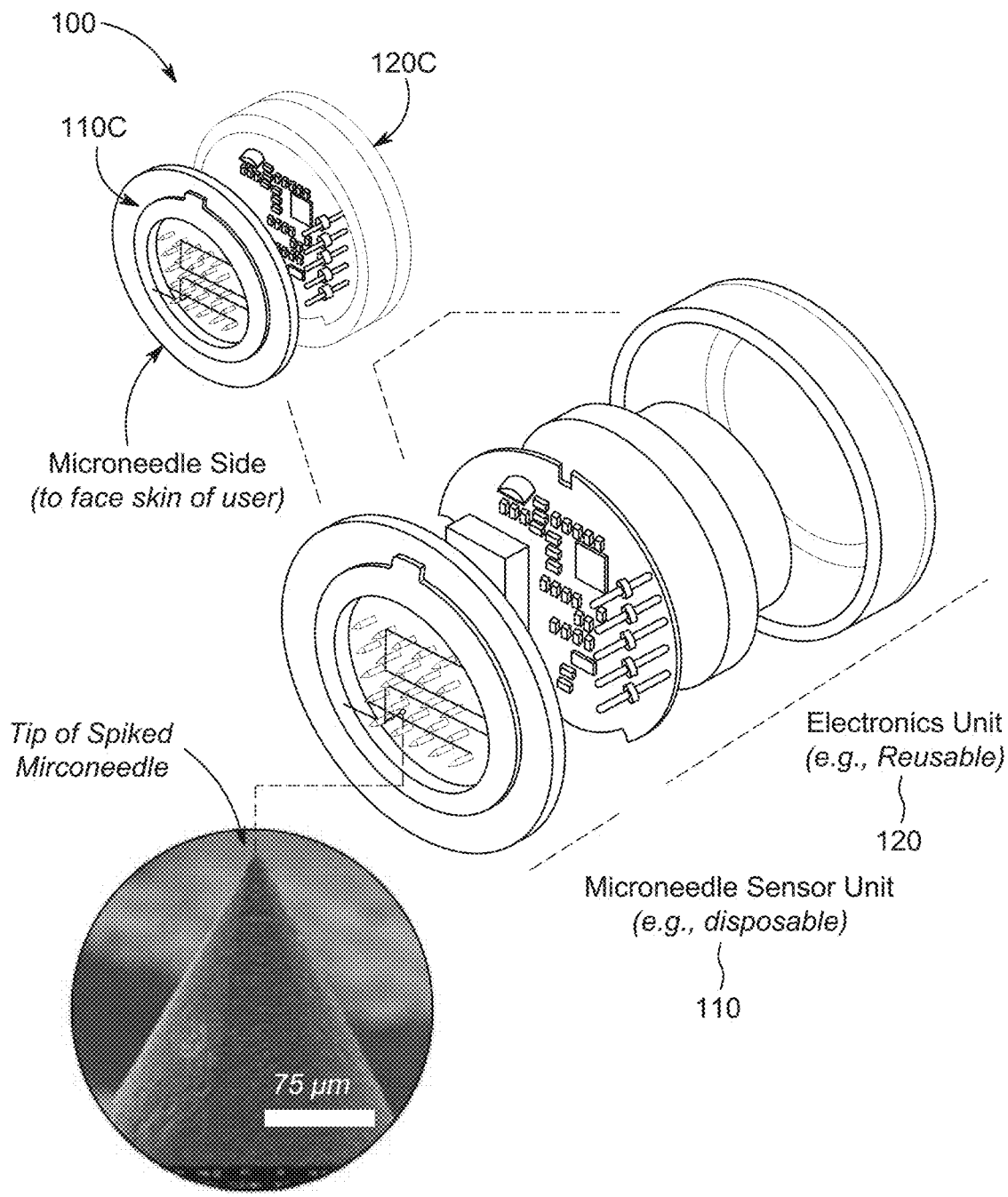

FIG. 1D shows a partially-exploded diagram illustrating the example embodiment of the wearable, non-intrusive microneedle sensor patch device 100 shown in FIG. 1C, depicting the both the microneedle sensor unit 110 that can be implemented as a disposable sensor component 110C and the electronics unit 120 that can be implemented as a reusable electronics unit 120C of the wearable, non-intrusive microneedle sensor patch device 100. In this example embodiment, the disposable portion of the microneedle sensor unit 110 can include the spiked microneedle array substrate coupled to a cover (e.g., cover ring) on the microneedle-side of the spiked microneedle array substrate. Also, in this example embodiment, the reusable electronics unit 120 can include electronic components encased (at least partially) in a holder (e.g., Holder A 163 in FIG. 1C) and an optional cover (e.g., Cover 170 in FIG. 1C).

Figure 1E:
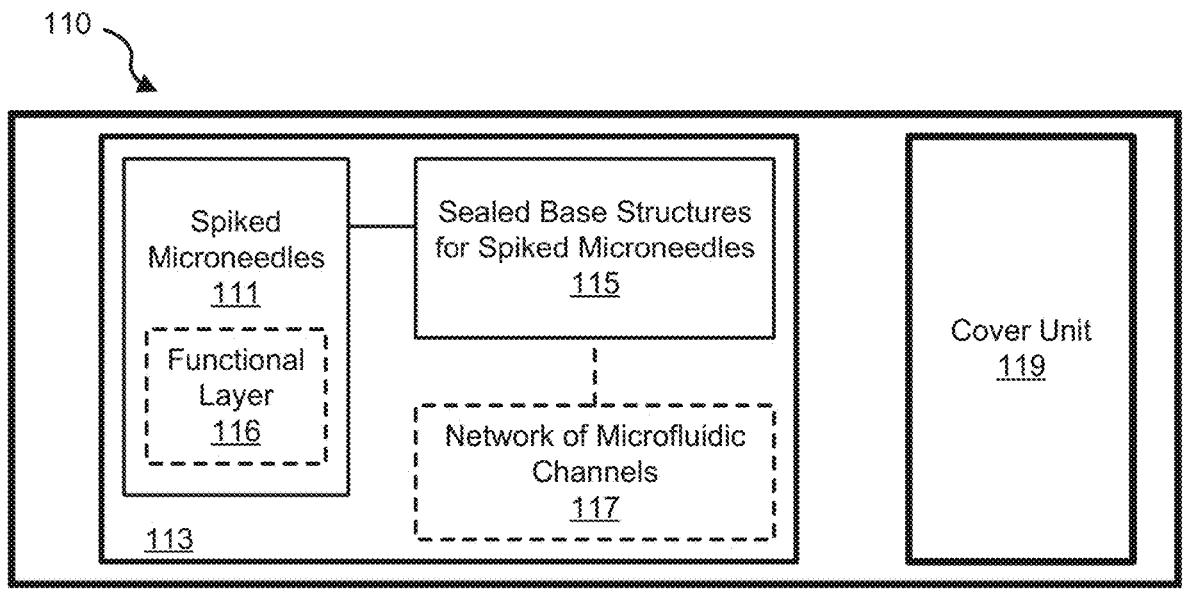

FIG. 1E shows a block diagram of an example embodiment of the microneedle sensor unit 110 of the wearable, non-intrusive microneedle sensor patch device 100. In this example, the microneedle sensor unit 110 includes a substrate 113, an array of spiked microneedles 111 are arranged on the substrate 113, and an array of sealed base structures 115 that couple to the lower region of a corresponding spiked microneedle 111. For example, a sealed base structure 115 provides support and stability to the respective spiked microneedle 111 to which it surrounds at the lower portion. In some embodiments, for example, at least some of the spiked microneedles 111 are configured as electrochemical sensor electrodes to detect an electrical signal from a reaction with a target analyte in a biofluid exposed to the array of spiked microneedle structures 111, e.g., where one or more of the electrochemical sensor electrodes can be functionalized by a chemical layer to interact with the target analyte in the biofluid in order to produce an electrical signal associated with the reaction that is detectable at the electrochemical sensor electrode(s).

In various implementations, for example, the target analyte can include a chemical substance that is associated with a biomarker. For example, the target analyte can include a metabolite, electrolyte, protein, amino acid, nucleic acid, lipid, liposome, nanoparticle, and/or therapeutic drug. In some examples of a metabolite, the target analyte can include a ketone body. In some examples of a protein target analyte, the target analyte can include an enzyme, peptide-based aptamer, antibody, or hormone. In some examples of a nucleic acid target analyte, the target analyte can include a nucleotide, oligonucleotide, oligonucleotide-based aptamer, deoxyribonucleic acid (DNA) or portion thereof, and/or ribonucleic acid (RNA) or portion thereof. In various implementations, for example, the biofluid containing the target analyte can include interstitial fluid, transdermal fluid, intraocular fluid, vitreous humor, cerebrospinal fluid, extracellular fluid, plasma, serum, lacrimal fluid, saliva, perspiration, mucus, and/or blood.

In some embodiments, the substrate 113 includes an electrically insulative material, which can be rigid or flexible in various embodiments, e.g., based on the desired application, such as location of the body where the wearable, non-intrusive microneedle sensor patch device 100 is to be placed. In some embodiments, for example, the substrate 113 can include polymethyl methacrylate (PMMA) or other electrically insulative polymer, e.g., including UV curable polymers; whereas in other embodiments, the substrate 113 can include an electrically insulative ceramic and/or metallic material, including a composite material, which may include a polymeric material. In some embodiments, the spiked microneedles 111 of the array include a total height (from bottom base to tip) ranging from 400 μm to 4,000 μm. In some embodiments, the spiked microneedle structure 111 of at least some of the spiked microneedles includes (i) a body region with one cylindrical exterior wall such that the spiked microneedle body is of a cylindrical shape, and (ii) a tip region with one conical exterior wall such that the spiked microneedle tip is of a conical shape. The lower portion of the body region of the spiked microneedle 111 is coupled to the substrate 113; and the lower portion of the body region can be encompassed, at least partially, by the sealed base structure 115. In some embodiments, for example, the spiked microneedle structures 111 are at least partially functionalized by a functional layer 116. For example, in some embodiments, the functional layer 116 can be deposited on just a portion of a spiked microneedle structure 111, e.g., such as the tip; or in other embodiments, the functional layer 116 can be coated on the tip and outer wall of the body of the spiked microneedle structure 111. In various embodiments, the functional layer 116 is configured to chemically facilitate an electrochemically detectable reaction with a target analyte.

In some embodiments, the microneedle sensor unit 110 includes a cover unit 119. The substrate 113, featuring the spiked microneedles 111, is couplable to the cover unit 119 comprising an array of openings arranged on a surface of the cover unit 119 to align with the array of spiked microneedles 111 on the substrate 113, such that the spiked microneedles 111 fit through the array of openings of the cover unit 119 when the cover unit 119 and substrate 113 are coupled together. In this manner, the cover unit 119 can both protect and seal the array of spiked microneedles 111 and underlying components from undesired substances from entering the device 100.

In some optional embodiments, for example, the microneedle sensor unit 110 includes a network of microfluidic channels 117 that are embedded in the substrate 113. In some implementations of such optional embodiments, the microfluidic channels 117 are responsible for flowing a custom resin material with optimal viscosity and capillary properties from one or more entry point(s) through the network of microfluidic channels to the interface where the substrate featuring the spiked microneedles 111 and cover unit 119 meet. For example, at this cover unit/spiked microneedle array interface, the resin material both (1) seals the two spiked microneedle 111-substrate 113 component and the cover unit 119 together and (2) insulates the spiked microneedles 111 to form the sealed base structures 115.

In some embodiments of the custom resin material, the resin material is formed of a polymer that is modified by a non-ionic surfactant and thermal treatment to render the desired viscosity and capillary properties. For example, the custom resin material can include a biomedical grade polymer composed of a mixture of acrylate and methacrylate based monomers and oligomers and a benzil ketal compound, e.g., Irgacur 651, as the photoinitiator, in which the polymer has an initial viscosity of 5 Pa·s. This polymer can be modified by adding the non-ionic surfactant (e.g., Triton X-100, 0.1-1% wt) that is thermally treated (e.g., thermal procuring at 65° C. for 20 min) to significantly decrease the viscosity, such that the final, custom resin material includes a viscosity within the range of 0.01 to 0.5 Pa·s. The low viscosity of the example custom resin material can considerably enhance the dynamic flowability of the overall polymer in the microfluidic channels 117. In implementations, for example, lowering the viscosity can result in more efficient crosslinking performance of the photoresin and thus create a highly chemically-resistant and biologically-resistant sealant material, which is an important factor during sensor modification, sterilization, and sensor use/application (e.g., in vivo and in vitro applications). In some embodiments of the custom resin material, the resin material can be configured to have resolution (size) lower than 500 nm.

Figure 1F:
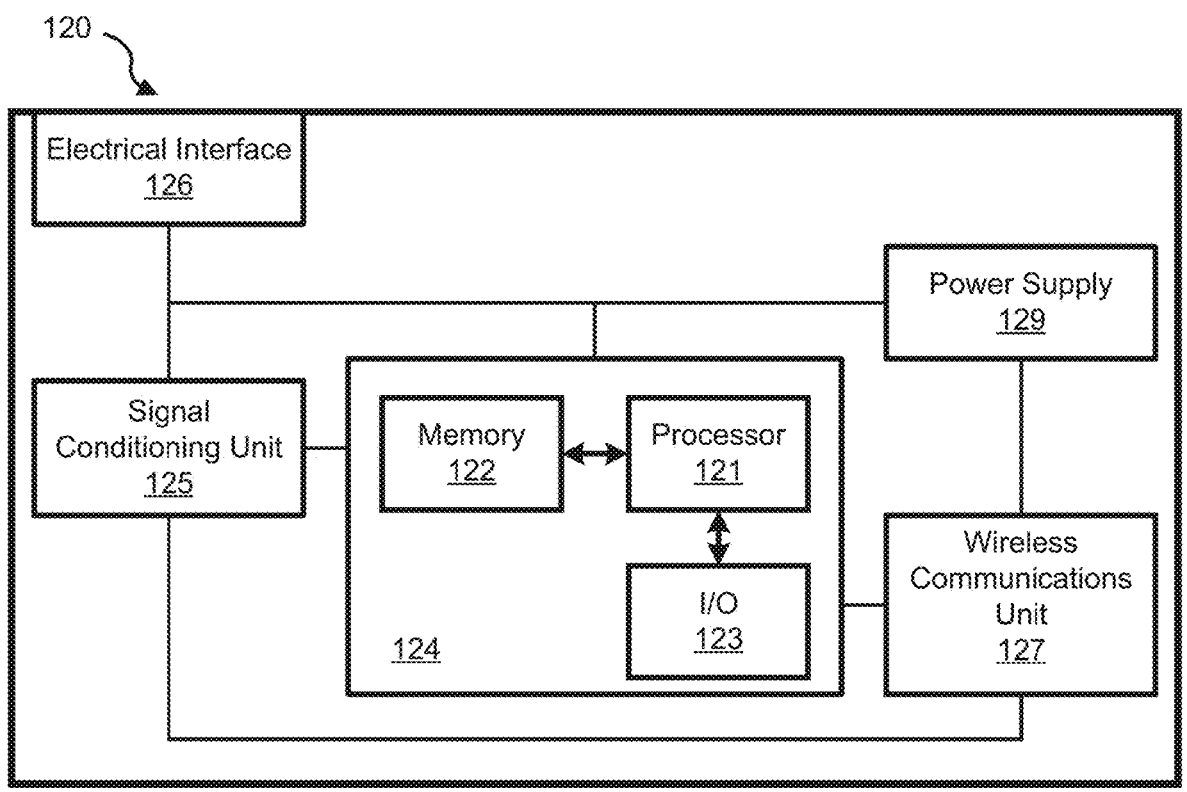

FIG. 1F shows a block diagram of an example embodiment of the electronics unit 120 of the wearable, non-intrusive microneedle sensor patch device 100. As shown in this example, the electronics unit 120 includes a signal conditioning unit 125, a power supply 129, an output unit (e.g., which can be embodied as a wireless communications unit 127), and an electrical interface (e.g., which can include one or more electrical interconnections, such as pins). The electronics unit 120 is configured to receive (e.g., at the electrical interface 126) and at least partially process electrical signals acquired from the sensor unit 110 (e.g., at the signal conditioning unit 125). In some embodiments, like that shown in FIG. 1F, the electronics unit 120 of the device 100 includes a data processing unit 124 to process the at least partially processed signals as data, e.g., in digital format. For example, in some implementations, the data processing unit 124 includes a microcontroller and multiplexer to manage data acquisition on data channels from the electrodes. The electronics unit 120 is configured to output the raw or partially processed electrical signals and/or processed data. In some embodiments, for example, the electrical interface 126 is configured to electrically couple to output ports of the microneedle sensor unit 110 that electrically connect to electrical conduits within the substrate 113 of the sensor unit 110; whereas, in some embodiments, for example, the electrical interface 126 can be configured as an array of electronic interface components, such as pins, that electrically couples to a corresponding array of electrical conduit terminus sites in connection with the array of electrodes (e.g., of the spiked microneedles 111) of the sensor unit 110, which electrically couples the array of electrodes to the signal conditioning unit 125 and/or other circuitry of the electronics unit 120.

In some embodiments of the electronics unit 120, for example, the signal conditioning unit 125 can include an electrical circuit including one or more amplifier(s) and filter(s) to condition the raw detected electrical signals from electrodes (e.g., spiked microneedles 111 and/or other electrodes) of the sensor unit 110, e.g., improving signal-to-noise ratio. In some implementations, the signal conditioning unit 125 can include drive circuitry for operating an electrochemical sensing technique performed at electrodes (e.g., the array of spiked microneedles 111) of the sensor unit 110 to implement the desired sensing mode for detecting the analyte from the biofluid.

In some embodiments of the electronics unit 120, for example, the output unit can include electrical contacts that electrically interface with an electrical conduit to provide the data to an external circuit or device. In some embodiments, for example, the output unit can include a wireless communications unit 127 that includes a wireless transmitter or transceiver device, e.g., such as an RF front-end (RFE), that is capable of communicating with an external device to provide raw, partially-processed, or fully-processed data from the data processing unit 124. For example, an RFE can manage the communication protocol of the wireless signal to be transmitted and/or received by an antenna of the output unit in such example embodiments. An example transceiver unit can include a BLE chipset to communicate with a BLE-enabled device, such as a smartphone. The power supply 129 can include a battery, fuel cell or other power source to supply power to the components of the electronics unit 120 and/or the sensor unit 110.

In some embodiments of the electronics unit 120, for example, the data processing unit 124 can include a processor 121 to process data, and memory 122 in communication with the processor 121 to store and/or buffer data. For example, the processor 121 can include a central processing unit (CPU) or a microcontroller unit (MCU). For example, the memory 122 can include and store processor-executable code, which when executed by the processor, configures the data processing unit 124 to perform various operations, e.g., such as receiving information, commands, and/or data, processing information and data, and transmitting or providing information/data to another device. To support various functions of the data processing unit 124, the memory 122 can store information and data, such as instructions, software, values, images, and other data processed or referenced by the processor 121. For example, various types of Random Access Memory (RAM) devices, Read Only Memory (ROM) devices, Flash Memory devices, and other suitable storage media can be used to implement storage functions of the memory 122. In some implementations, the data processing unit 124 includes an input/output (I/O) unit 123 to interface the processor 121 and/or memory 122 to other modules, units or devices, e.g., associated with the mobile device 130, the remote data processing system 140, and/or other external devices. In some embodiments, the processor 121, memory 122, and/or I/O unit 123 is in communication with the wireless communications unit 127, e.g., such as a transmitter (Tx) or a transmitter/receiver (Tx/Rx) unit. For example, in such embodiments, the I/O unit 123 can interface the processor 121 and memory 122 with the wireless communications unit 127, e.g., to utilize various types of wireless interfaces compatible with typical data communication standards, which can be used in communications of the data processing unit 124 with other devices, e.g., such as between the one or more computers in the cloud and the user device. The data communication standards include, but are not limited to, Bluetooth, Bluetooth low energy (BLE), Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces. In some implementations, the data processing unit 124 can interface with other devices using a wired connection via the I/O unit 123. The data processing unit 120 can also interface with other external interfaces, sources of data storage, and/or visual or audio display devices, etc. to retrieve and transfer data and information that can be processed by the processor 121, stored in the memory 122, or exhibited on an output unit of the mobile device 130 (e.g., smartphone) or an external device.

The wearable, non-intrusive microneedle sensor patch device 100 provides a two-component wearable sensor system (e.g., disposable sensor and reusable electronics) that addresses multiple, multi-faceted problems of current state-of-the-art microneedle sensor systems. For example, the specially-designed spiked microneedle structures of the wearable, non-intrusive microneedle sensor patch device 100 is configured to have a geometry, length and girth (e.g., aspect ratio), surface roughness, and material configured to not cause substantial pain to the user, while still having the necessary detection sensitivity of a conventional electrode to meet the requirements of an electrochemical electrode system, such as (i) allowing chemically-functionalization to facilitate redox or other chemical reactions with a target analyte in the host biofluid, (ii) conducting electrical signals produced from such reactions with the target analyte to detect parameters (e.g., concentration) of the target analyte in the biofluid, and (iii) reproducibility and reliability of the detectable electrical signals.

For example, the spiked microneedle structures 111, in contrast with conventional photolithography-based silicon microneedle structures and other existing microneedles, can be manufactured in a wide range of geometries made appropriate to specific skin penetrating applications and using a wide range of materials, e.g., including most polymers, metals such as aluminum and some classes of steels, and also some ceramics and semiconducting materials. Moreover, the spiked microneedle structures 111 can be structured to have a unique and high surface roughness (e.g., in a range of 50 nm to 400 nm peak roughness, such as for PMMA spiked microneedle structures fabricated by the disclosed micro-computer numerical control (CNC) or micro-molding techniques), which is highly desired for sensing applications enabling enhanced sensitivity as well as reagent protection and overall enhanced structural integrity of the reagent layers—each of which contributes to long term stability of the sensor.

Additionally, for some embodiments of the disclosed spiked microneedle structures 111 (discussed below), the body of the microneedle can include a unique spiral structure, in contrast with conventional flat microneedle body structure, which enhances the applied penetration stress by turning the single shear stress in a non-spiral structure to added shear and torsional stresses, e.g., resulting in reduction of the penetration force required to move through the skin, and thus reduction of potential pain as well as potential trauma to the skin of the wearer.

Moreover, for example, the wearable, non-intrusive microneedle sensor patch device 100 is configured to space the spiked microneedle structures on the substrate to mitigate or eliminate 'cross-talk' that typically plagues a multi-analyte detection sensor. For example, multi-analyte sensors for detecting oxidase-based enzymes, in particular, can suffer from chemical cross-talk that largely affects the detectable signal response and thus accuracy of the multiplexed sensors. The chemical cross-talk is a result of the diffusion of the hydrogen peroxide enzymatic product of an analyte sensor to a neighboring sensor for another analyte. In the example embodiments disclosed herein, the cross-talk issue can be addressed through a combination of optimizing the spacing between the microneedle sensors and mitigating the amount of chemical agents susceptible to cross-talk (i.e., mitigated sensitivity). In some example embodiments, the sensitivities can be reduced in multiplexed sensors via reducing the number of microneedles (i.e., reducing the active surface areas) to below 10 $nA \cdot mM^{-1}$, and/or the spacing can be kept above 5 mm to remove any chemical cross-talk possibility.

Further advantages of the disclosed microneedle sensor technology include robustness of the overall sensor patch device. For example, the wearable, non-intrusive microneedle sensor patch device 100 can be structured to safely secure the spiked microneedle structures 111 to the sensor substrate 113 by providing a sealed base structure 115 that surrounds the lower portion of the spiked microneedles 111, which can be fabricated by a new fabrication technique in accordance with the disclosed technology that is scalable, mask-free, and reproducible to create this stabilizing, insulation layer for the array of spiked microneedles 111.

Figure 2A:
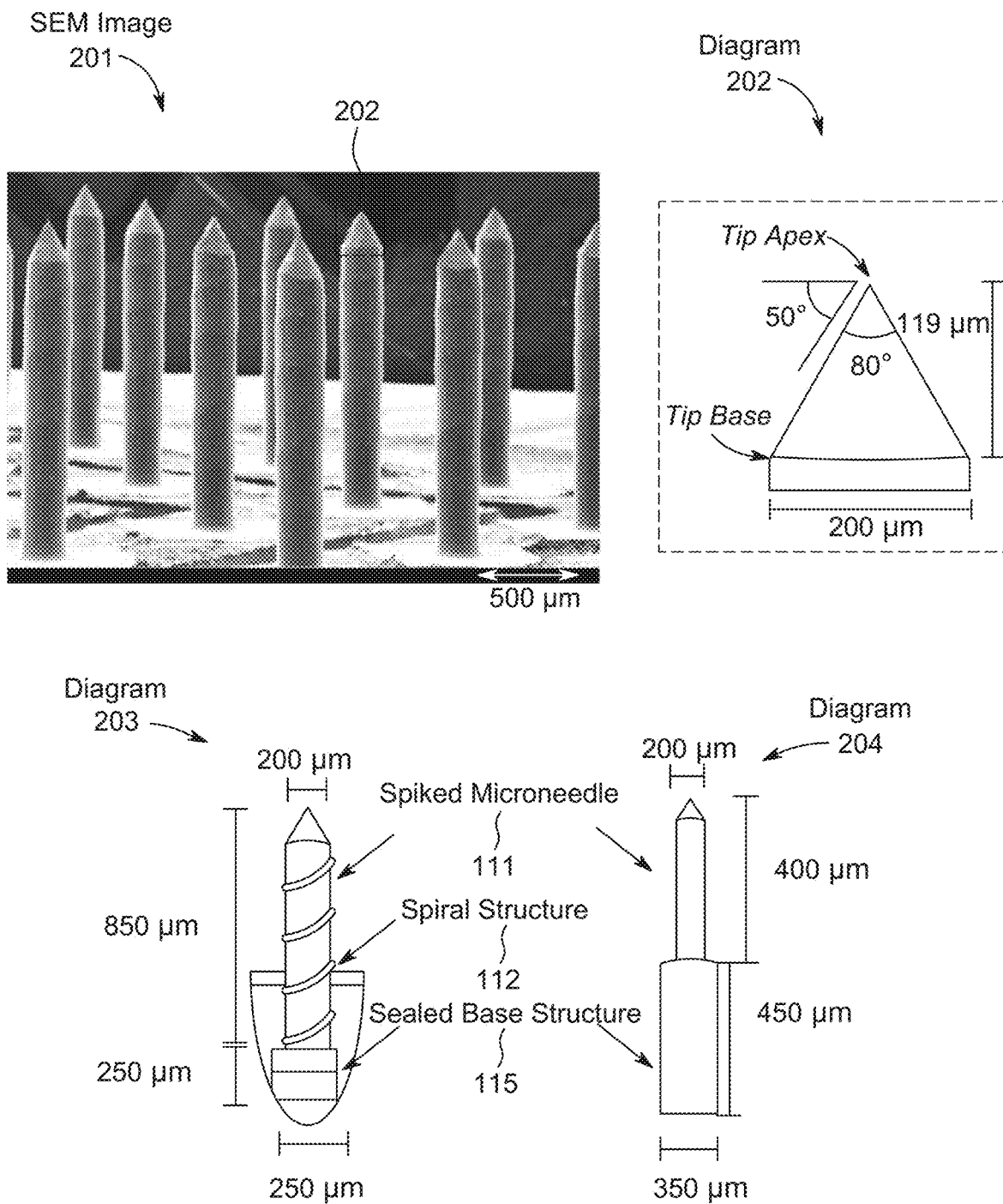
FIGS. 2A and 2B show images and diagrams showing an example embodiment of spiked microneedle structures in accordance with the present technology.
Figure 2B:
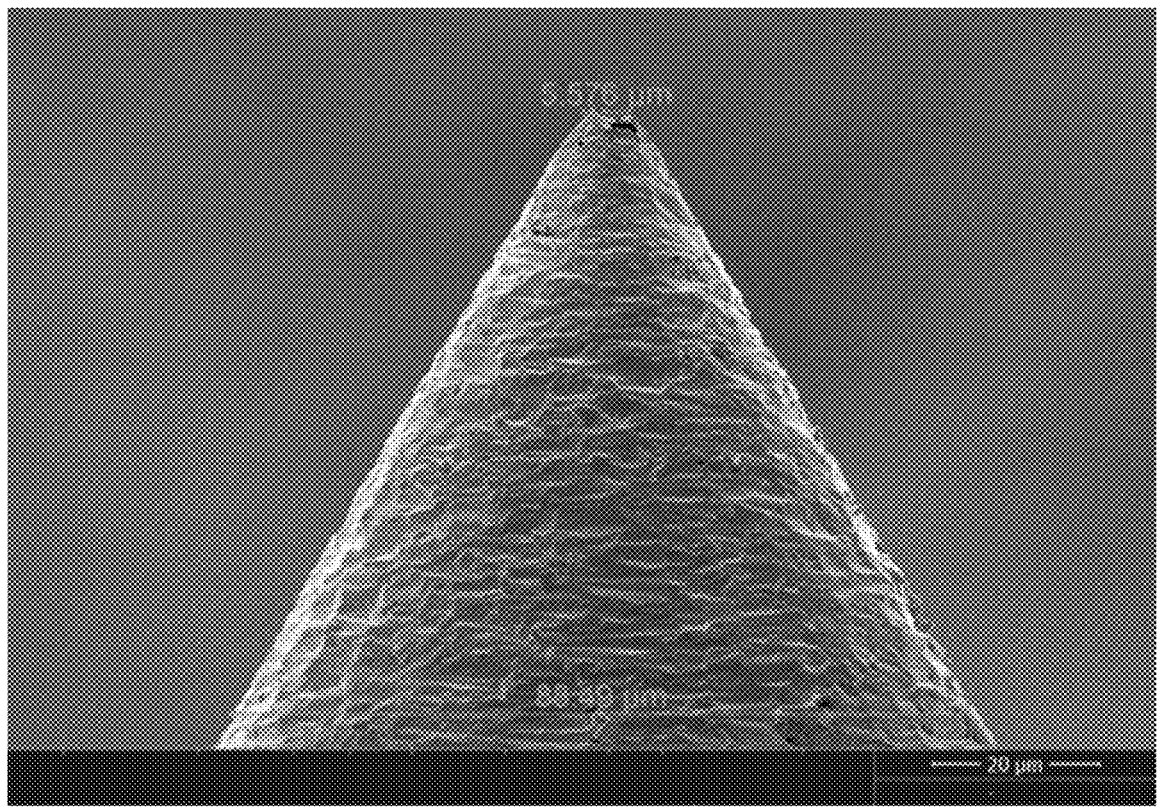
Figure 2B:
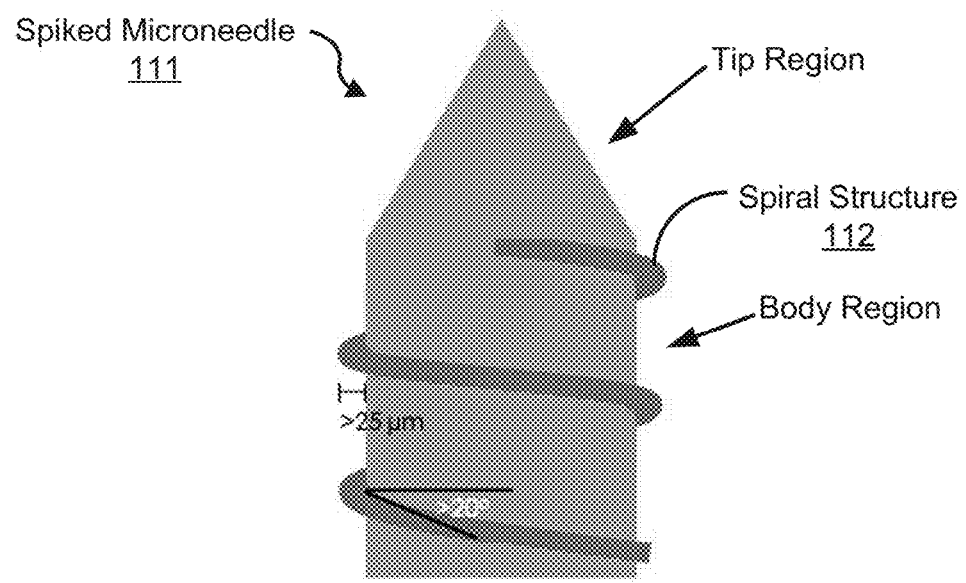

FIGS. 2A and 2B show images and diagrams showing various aspects of an example embodiment of the spiked microneedles 111. The images and diagrams in FIG. 2A demonstrate the geometry of the spiked microneedle structures 111 and their securement to the substrate 113 via the sealed base structures 115. SEM image 201 shows example spiked microneedles 111 on substrate 113 prior to the sealed base structure 115 added; diagram 202 shows an example spiked microneedle tip depicting an example of the tip dimensions (e.g., tip angle of 80°, tip height of 119 μm, and tip base of 200 µm diameter length, with tip aspect ratio of ≅0.6, height:base); and diagrams 203 and 204 show example embodiments of a spiked microneedle 111 with a sealed base structure 115 of different heights (e.g., 250 µm height and 250 µm diameter length in diagram 203, and 450 µm height and 350 µm diameter length in diagram 204).

In some embodiments of the wearable, non-intrusive microneedle sensor patch device 100, for example, the spiked microneedle structures 111 can be configured to have a height (from body base to tip apex) in a range of 800 µm to 4,000 µm (0.8 mm to 4 mm). In some embodiments, for example, the tip of the spiked microneedle structures 111 can be configured to have: (i) tip height in a range of 100 µm to 200 µm, (ii) tip base diameter or thickness in a range of 50 µm to 450 µm, and (iii) tip angle (at apex to tip base) in a range of 40° to 85°. In some embodiments, for example, the body of the spiked microneedle structures 111 can be configured to have a diameter or thickness (e.g., horizontal length or girth) in a range of 50 µm to 450 µm. In some embodiments, for example, the spiked microneedle structures 111 can be configured to have an overall height-to-thickness aspect ratio in a range of 4:1 to 20:1.

Also, as shown in FIG. 2A, the spiked microneedle structures 111 are designed in a specialized non-intrusive, pain-free skin-penetrating geometry, also referred to as "reproducibly randomized spiral (RRS)," which includes a circular cross-section having a thin, winding spiral protrusion (spiral structure 112) that is extruded from a solid surface base to a desired height at the tip of the spiked microneedle. The spiked microneedle structures 111 are configured to have their circular body spirally span from the microneedle structure base (bottom) to a point along the body that defines a base of the tip, from which the microneedle structure converges to a sharp point at the apex.

FIG. 2B shows another SEM image depicting an example tip region of an example spiked microneedle structure 111 and an illustration of an example spiked microneedle structure 111 having the spiral structure 112. As depicted in the SEM diagram 201 shown in FIG. 2A and the illustration shown in FIG. 2B, the body (and outer wall) of the spiked microneedle structure 111 is configured to be spiral-like with a spiral structure 112, which can have at least 20° of spiral angle and at least 25 µm of valley-to-spike height. This structure, for example, can enhance the skin penetration by introducing added torsional stresses of the spiked microneedles 111 at a constant pressure, e.g., as compared to the flat, non-spiral surface of a microneedle body, while pressing the microneedle patch to the skin, which result in a smoother skin penetration. Additionally, the spiral structure 112 of the body (and outer wall) of the spiked microneedle structure 111 reduces the surface contact (friction between the two bodies) at the microneedle/skin interface, e.g., thus reducing the insertion force required. This reduction in surface force not only reduces the potential for pain to the user, but also reduces deleterious forces that can damage the microneedles and/or the skin tissue with consequent traumatic bodily reactions, thereby providing the overall sensor unit 110 with more robust, stable spiked microneedle structures 111, and sensing capability.

This disclosure provides example comparative data of example embodiments of the wearable, non-intrusive microneedle sensor patch device 100 and conventional microneedle sensors, demonstrating how end users of the example spiked microneedle sensor device 100 experienced little or no pain (e.g., pain level of 0, 1 or 2 on a scale of 1-10), whereas end users of conventional microneedle sensor devices experienced significant pain (e.g., pain level of 4 to 8 on the scale of 1-10).

Table 1 shows example data from a qualitative pain study using an example embodiment of the disclosed spiked microneedle sensor patch device, e.g., including the spiral-winding projection on the extending body of the microneedle, e.g., in comparison with different conventional microneedle sensor devices on human subjects with different ages, ethnicity, and gender.

TABLE 1

| | Pain Level (in a scale of 0-10) | | |
|---|---|---|---|
| Human Subject | Spiked Microstructure Array (e.g., manufactured by Micro-Casting or Micromachining) | High Resolution 3D printed Micro-needle Device | Nano Pen Stainless Steel Microneedle Device |
| 1 | 1/10 | 5/10 | 6/10 |
| 2 | 0/10 | 7/10 | 8/10 |
| 3 | 2/10 | 6/10 | 7/10 |
| 4 | 1/10 | 5/10 | 6/10 |
| 5 | 0/10 | 4/10 | 6/10 |
| 6 | 0/10 | 5/10 | 6/10 |
| 7 | 0/10 | 4/10 | 6/10 |

In some embodiments, for example, on the sensor substrate 113, the spacing among spiked microneedle structures 111 can be configured to be at least 1.3 mm apart from each other. Also, for example, in cases for multiple (multiplexed) analyte sensors, the spacing between different sensing electrode regions (e.g., glucose, lactate, alcohol etc.) can be configured to be at a least 5 mm.

In some embodiments, for example, the spiked microneedles 111 are structured to include a rigid, insulative material core that is coated by an electrically conductive material, such that a detectable electrical signal at the tip of the spiked microneedle (operating as an electrode) is conducted along the electrically conductive outer coating to an electrical conduit disposed in or on the substrate 113. For example, in some embodiments, the core or interior material of a spiked microneedle structure 111 includes one or more polymeric materials, e.g., including but not limited to poly (methyl methacrylate) (PMMA) polyether ether ketone (PEEK), polycarbonate (PC), ultra-high-molecular-weight polyethylene (UHMW), and/or photocurable copolymer(s), which can be obtained from urethane dimethacrylate, bis-phenylglycidyl dimethacrylate, and triethylene glycol dimethacrylate; and in some embodiments, for example, the electrically conductive outer coating includes, but is not limited to, one or more of gold, platinum, silver, chromium, a carbon material (e.g., graphite, boron-doped diamond, highly oriented pyrolytic graphite, graphene, carbon nanotubes (CNTs), or other carbon material) and/or other conductive metal or alloy. For example, a first set of spiked microneedle structures can be configured to include a first electrically-conductive outer coating (e.g., platinum, gold, silver, etc.) for the detection of a first target analyte, and a second set of spiked microneedle structures can be configured to include a second electrically-conductive outer coating (e.g., graphite carbon, B-doped diamond, etc.) for the detection of a second (other) target analyte present in the biofluid. In some embodiments, for example, a thin-film deposition of the electrically conductive material includes sputtering Cr/Pt/Ag, followed by etching of Ag from all at least one or some of the spiked microneedles 111 of the array (e.g., etching of Ag on the spiked microneedles configured to be working and counter microneedle microelectrodes), and then followed by chloritization of the Ag to Ag—AgCl on at least one or some of the spiked microneedles 111 of the array (e.g., configured to be the reference microneedle microelectrode(s)). The reference microneedle electrodes can be further coated by a first reference electrode coating (e.g., a NaCl-saturated solid polymer matrix), which can be subsequently coated by a second reference electrode coating (e.g., an outer PVC polymer containing Triton X-100 surfactant).

Figure 3:
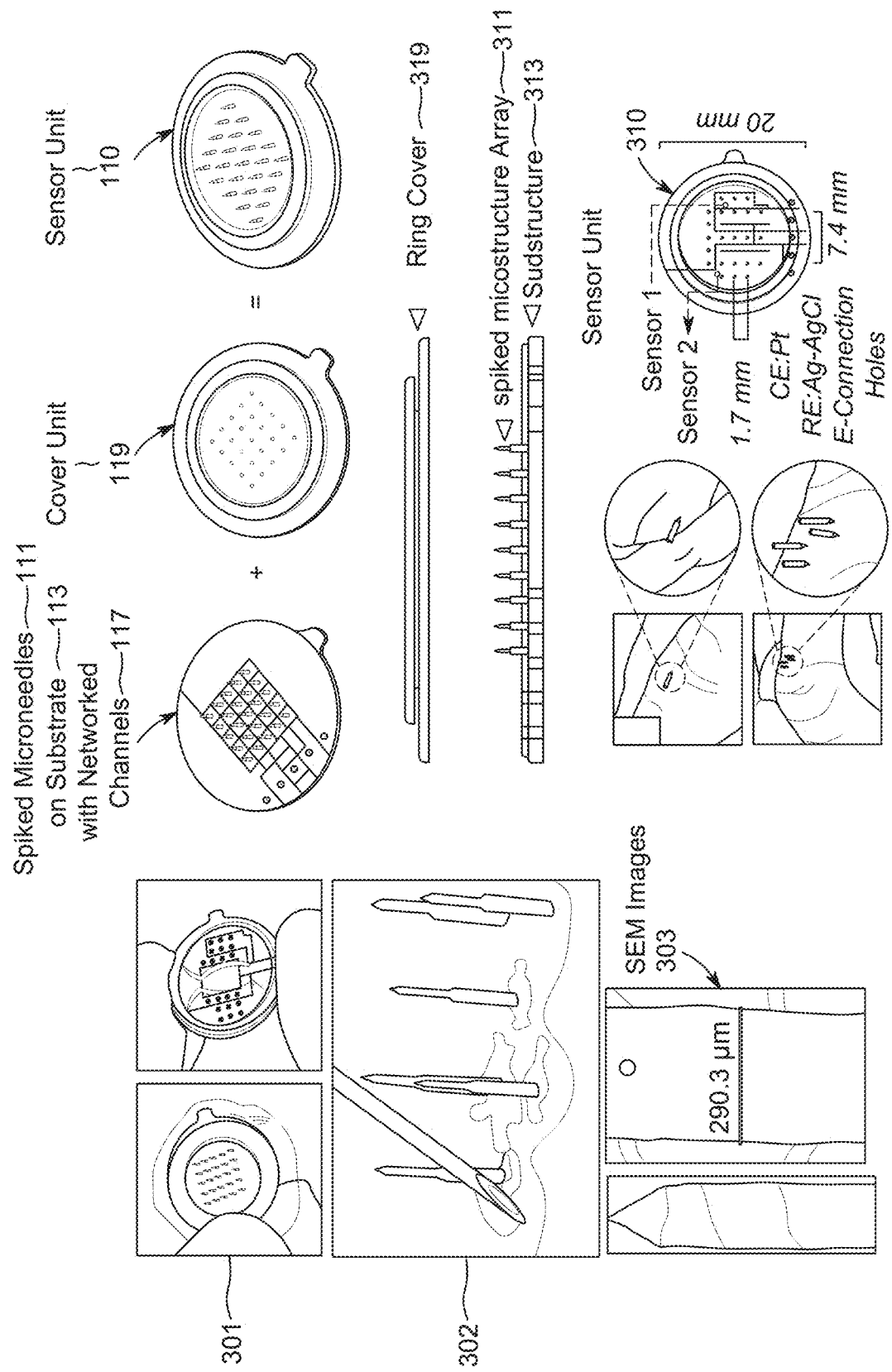
FIG. 3 shows panels of images and diagrams showing various examples of a microneedle sensor unit, including an example arrangement of the spiked microneedles on a substrate and an example substructure of the substrate.

FIG. 3 shows panels of images and diagrams showing the microneedle sensor unit 110, including an example arrangement of the spiked microneedles 111 on the substrate 113 and substructure of the substrate 113. On the left side of FIG. 3, image 301 shows an example single (left) and multiple (right) analyte sensor unit, respectively; image 302 shows an optical micrograph of an example spiked microneedle array with 150 μm diameter next to a stainless-steel insulin injection nano-pen (34 gauge); and SEM images 303 show zoomed views of an example spiral spiked microneedle 111. On the right side of FIG. 3, a top series of diagrams illustrates an example array of spiked microneedles 111 on the substrate 113 with an example network of microfluidic channels 117 (which can be used to flow insulative material to seal the spiked microneedles 111 and form a sealed base 115), as well as show how this combines with an example cover unit 119 to form an example sensor unit 110. A middle series of diagrams illustrates a side view of the example cover unit 119, configured as a ring cover 319. The lower series of diagrams illustrate an example embodiment of a spiked microneedle sensor unit 310 for multi-analyte simultaneous detection, which includes two sensor regions of spiked microneedles (each with 1.7 mm spacing between spiked microneedles), a reference electrode (e.g., Ag—AgCl), a counter electrode (e.g., Pt), and electronic-connection holes. The lower series of diagrams also includes images showing individual spiked microneedles on a single strand of hair and their penetration to the skin (e.g., on a finger).

Figure 4A:
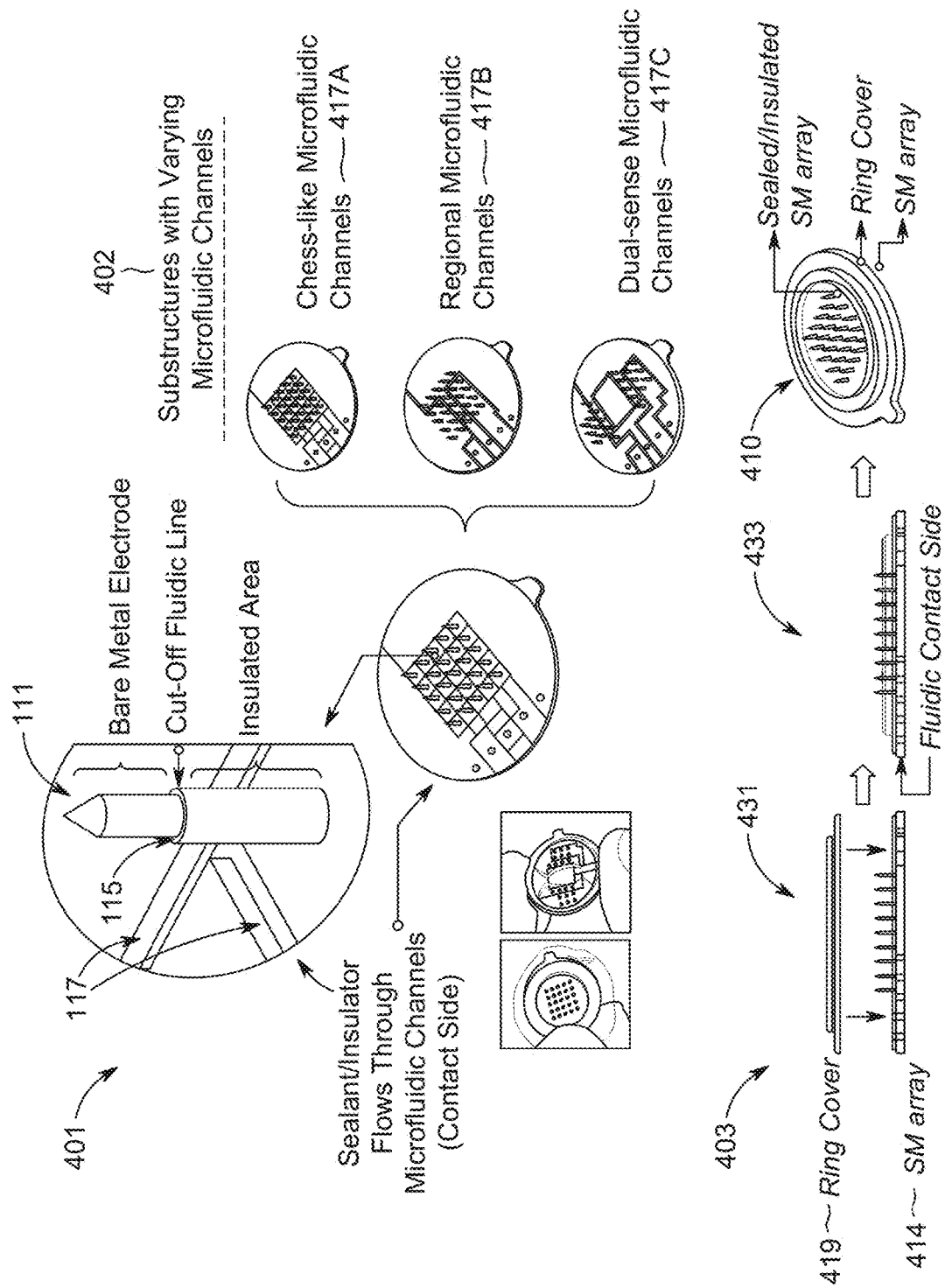
FIG. 4A shows illustrative diagrams showing various aspects of an example spiked microneedle sensor unit in accordance with the present technology, including example spiked microneedle structures and base structures and array configurations.

FIG. 4A shows illustrative diagrams showing various aspects of an example spiked microneedle sensor unit 110, including example spiked microneedle structures 111 and base structures 115 and example array configurations. On the left side of FIG. 4A, a diagram 401 shows an example embodiment of a spiked microneedle 111 with an insulated sealed base structure 115 and network of microfluidic channels 117, within which a sealant/insulator material can flow through to create the sealed base structure 115. Diagram 402 of FIG. 4A shows example 5×5 array of spiked microneedle structures 111 on a substrate 113 featuring various substructures of differing networks of microfluidic channels 117, e.g., including a "chess-like" microfluidic channel structure 417A that encompasses each spiked microneedle structure 111, a "regional" microfluidic channel structure 417B that encompasses sensor regions, and a "multi-sense" or "dual-sense" microfluidic channel structure 417C that encompasses particular sensor regions associated with multiple (or dual) analyte sensing. Diagram 403 illustrates an example assembly process to insert an example cover unit 119 (e.g., ring cover 419) on an example spiked microneedle sensor array-substrate (e.g., spiked microneedle array substrate 414) to produce an example embodiment of the microneedle sensor unit 410. Notably, in this example, the sealed base structures that surround and support the base region of the spiked microneedles to the substrate are produced after insertion of the ring cover 419 to the spiked microneedle array substrate 414, e.g., by microfluidic transfer and sealing of a resin material, as discussed below.

For example, in some implementations, the spiked microneedle array-substrate (e.g., spiked microneedle array substrate 414) and the cover unit (e.g., ring cover 419) are sealed together using a new technique that utilizes a network of microfluidic channels that are engraved in the substructure of the sensor substrate. The network of microfluidic channels are responsible for flowing a custom-made resin with optimal viscosity and capillary properties from a single-entry point through the entire network of microchannels to the cover unit/microneedle array-substrate interface, which can flow up to a cut-off fluidic line that is designed to stop the capillary flow of the resin-based sealant/insulator at the line. This technique is referred to as an autonomous capillary sealing/insulating method, which both seals the two components (i.e., the spiked microneedle array-substrate and the cover unit) and insulates each of the spiked microneedles in a highly reproducible manner at the cut-off fluidic line stopper. The method can fabricate the sealed base structures at, at least, tens of microns to hundreds of microns high (e.g., 250 μm or 450 μm as shown in FIG. 2A), during which a reproducibility/capillary cutoff line of the substructure of the substrate 113 can stop capillary motion of the resin-based sealant/insulating fluidic polymer that seals the two components (cover unit and spiked microstructure components) together creates the insulating structure of the base structure 115 surrounding the desired lower portion of the bare spiked microneedle electrodes surface area.

Figure 4B:
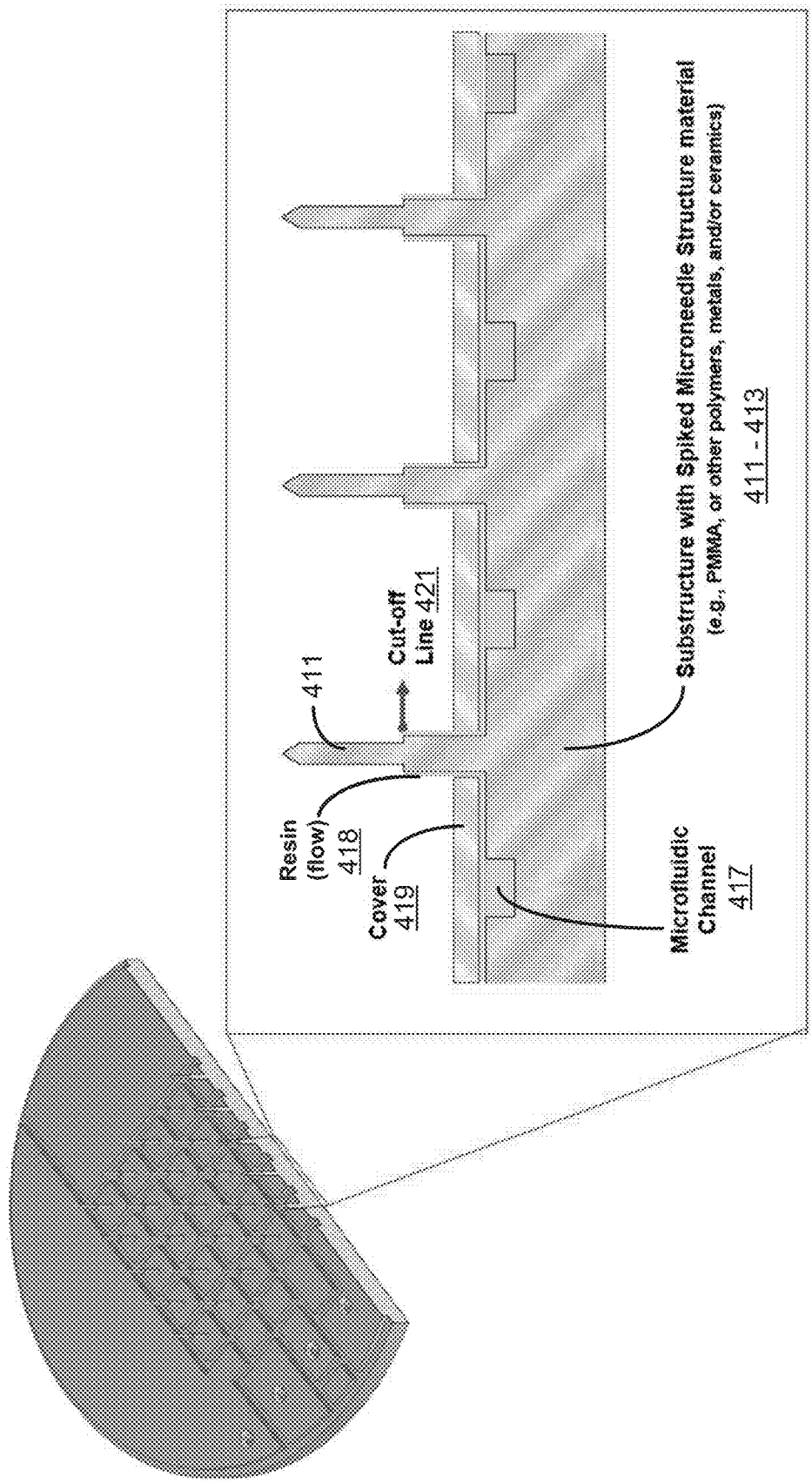
FIG. 4B shows a cross-sectional diagram illustrating an example process of an autonomous capillary sealing/insulating method for producing base support structures of spiked microneedle structures, in accordance with the present technology.

FIG. 4B shows a cross-sectional view diagram 407 illustrating an example embodiment of spiked microneedle structures 411 and substructure of substrate 413 (e.g., of PMMA material, or other polymer, metal and/or ceramic material) with an example network of microfluidic channels 417 and covered by an example ring cover 419, which facilitate the autonomous capillary sealing/insulating method that can flow the custom resin material 418 through the microfluidic channels 417 and through gaps between the substructure 413 and cover 419 and outward to the cut-off line 421, which can create sealed base structures (e.g., via photocuring the resin 418). In example implementations of the method, for example, the cut-off line 421 or area of the spiked microneedle structure 411 can (i) provide a location where the autonomous flow of the microfluidic sealant stops flowing, and (ii) serve as a structure responsible for where the spiked microneedle structures are to be reproducibly insulated.

Figure 4C:
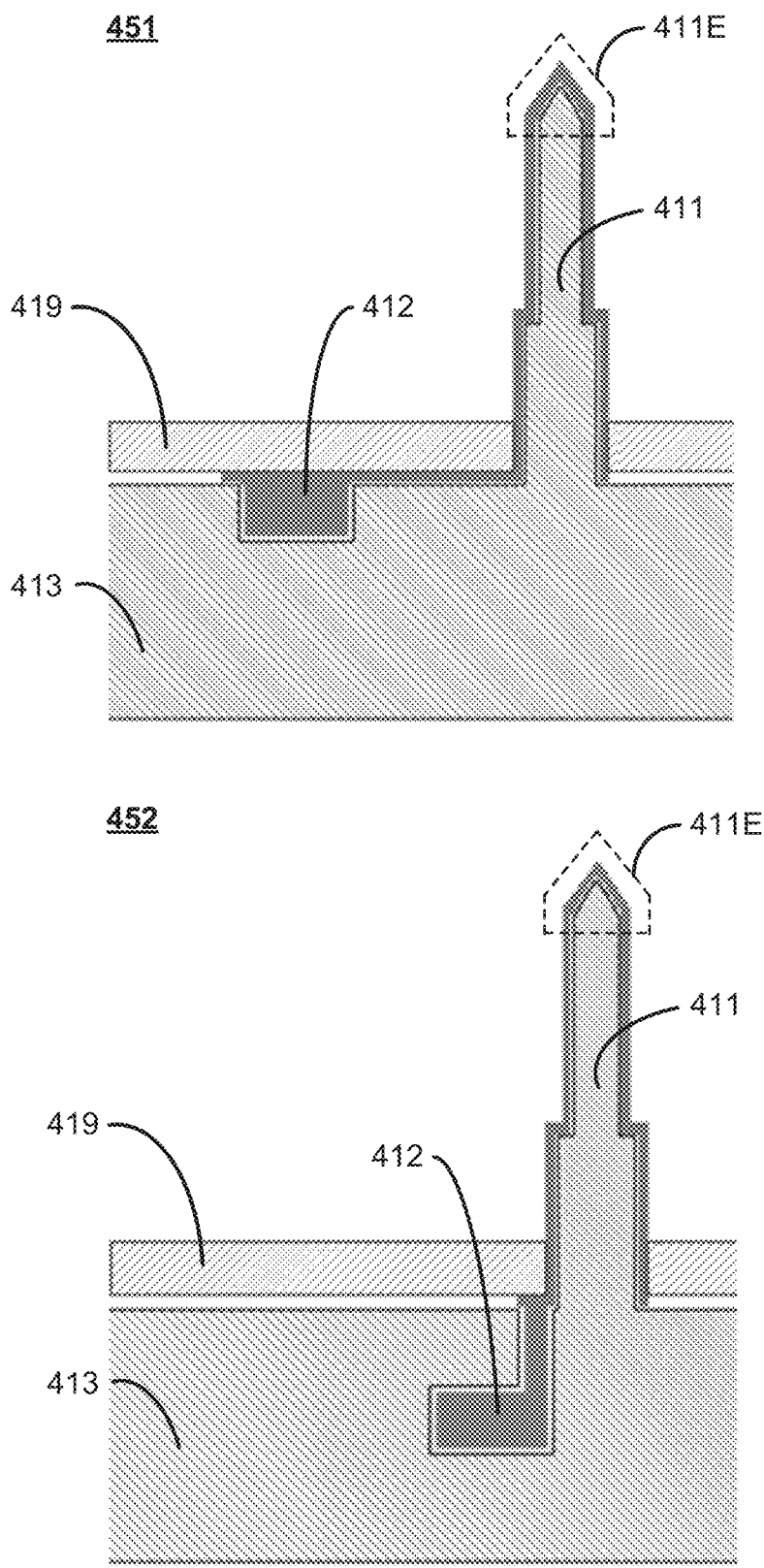
FIG. 4C shows cross-sectional diagrams illustrating example embodiments of spiked microneedle structures and substrate substructure with examples electrical conduit interconnections, in accordance with the present technology.

FIG. 4C shows cross-sectional view diagrams 451 and 452 illustrating example embodiments of spiked microneedle structures 411 and substructure of substrate 413 with an example electrical conduit 412 that is configured to electrically couple the electrode 411E of the spiked microneedle structure 411 to a terminus or contact region of the electrical conduit 412 on the substrate 413 (not shown). The diagram 451 depicts an example embodiment where the electrical conduit 412 is configured on or at least partially in the substrate 413; and the diagram 452 depicts an example embodiment where the electrical conduit 412 is configured within the substrate 413. In these examples, the s substrate 413 is covered by the example cover 419.

Referring back to diagram 403 in FIG. 4A, the autonomous capillary sealing/insulating method is a spontaneously autonomous process that includes (1) a process 431 to assemble the cover unit and microneedle array-substrate, followed by multiple processes 433 involving (2a) contact and inflow of the custom-designed photocurable resin from the contact side of the assembled sensor patch through the network of microfluidic channels, (2b) followed by heat treatment (e.g., at 70° C. for 5 minutes), (2c) followed by UV curing (e.g., at 90° C. for 1 hour). The resulting device, e.g., spiked microneedle sensor unit 410, is a single component sensor array fully sealed and reproducibly insulated. Notably, the resulting sensor unit (e.g., single piece) becomes significantly tough with greatly enhanced mechanical robustness, which can be attributed, for example, due to the specialized resin filling the vacant microfluidic channels and/or inner micro-gaps between the cover unit (e.g., cover ring 419) and the substructure, and around the holes of the cover ring 419 and the individual spiked microneedles, e.g., based on the mechanically tough properties of the resin material.

Also, for example, the microfluidic channels (e.g., which can have a depth and/or width ranging from 100-400 µm) that are created on and/or in the substructure can also serve as electrical isolation channels (e.g., when masked or engraved to individually addressable electrical regions) for an electrical isolation process step of the fabrication method, which can include (i) guiding the mechanical scraping of the metal sputtered inside the channels (that can leave the rest of the substrate into electrically isolated islands/regions), or (ii) holding solid or liquid-based masks that can be fit inside the channels before any metal deposition and removed after the metal thin film deposition. This can be implemented by laser engraving, micro-CNC machining, or manual scraping of the metal inside of the channel according to the final design of the spiked microneedle regions, as illustrated by the examples in diagram 402, which can leave certain regions to be electrically connected or electrically isolated from each other. Further details about the fabrication method are described later in this patent document.

Figure 5:
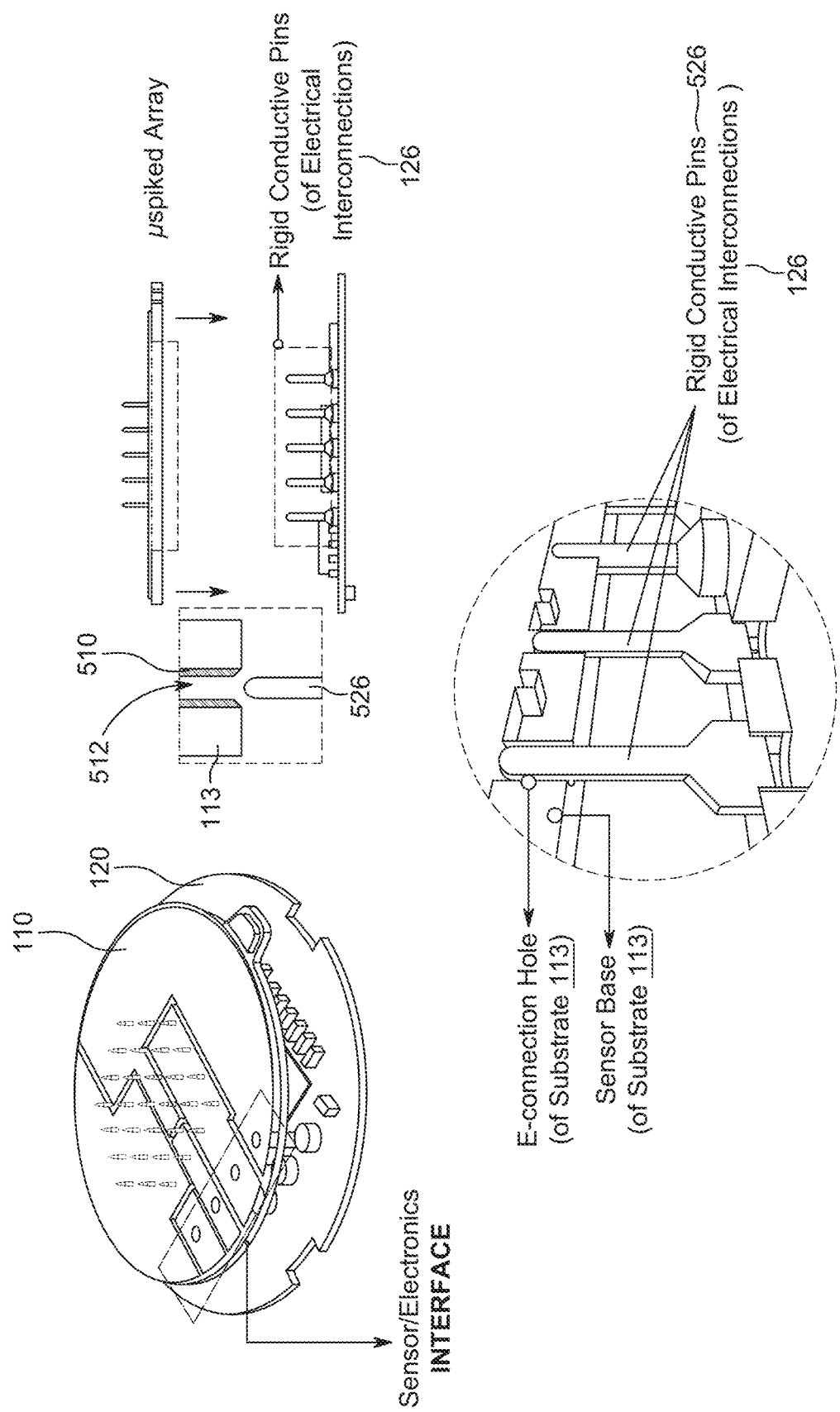
FIG. 5 shows diagrams depicting example embodiments of a substructure of a microneedle sensor unit and electrical interconnections of the electronics unit, in accordance with the present technology.

FIG. 5 shows diagrams depicting example embodiments of the substructure of the microneedle sensor unit 110 and electrical interface 126 of the electronics unit 120, showing how the electronic interface contact is designed for reliability of electrical signal transfer across electrical contacts from the sensor unit 110 (e.g., disposable component) to the electronics unit 120 (e.g., signal conditioning unit, which can provide a potentiostat). The substrate 113 includes a plurality of electrically-conductive, friction-based contacts 510 (e.g., less than 100 nm thickness) that are disposed within openings 512 of the substructure of the substrate 113. The example electrically-conductive, friction-based contacts 510 are coupled to electrically-conductive conduits (e.g., interconnects or vias) that couple to the array of electrodes of spiked microneedle structures 111. The example openings 512 of the substructure of the substrate 113, combined with the electrically-conductive, fiction-based contacts 510, are sized to receive the elongated region of rigid electrically-conductive pin structures 526 of the electrical interface 126.

For example, an advantage of the sensor/electronics electrical interface design is related to the single-step sputtering/metal film deposition process of the microneedle sensor unit 110, which allows for top-down sputtering that fills the openings 512 with electrically conductive material to form the contacts 510, where the rigid conductive pins 526 of the electronics unit 120 (or an intermediate interface) inserts. The resulting electrically-conductive, friction-based contact 510 provides an electrical-noise-free and reliable interface, even during high intensity body motions (by the user), which is a challenging objective to achieve (e.g., particularly for nano-ampere sensitivity systems for epidermal analyte-based electrochemical sensing applications). The rigid, electrically-conductive pin structures 526 are configured on the PCB layer of the electronic unit 120 to mechanically align with corresponding openings 512. Such pin structures 526 can be fabricated using an orientation aligner design and configured to have a round tip at the apex of the pin structure 526 for smooth insertion to the openings 512 of the sensor unit 110. Also, for example, the bottom side of the contacts 510 within the openings 512 can be designed and fabricated to be beveled to provide a wider entrance zone for easier guiding of the rigid pins 526 into the openings 512.

Figure 6:
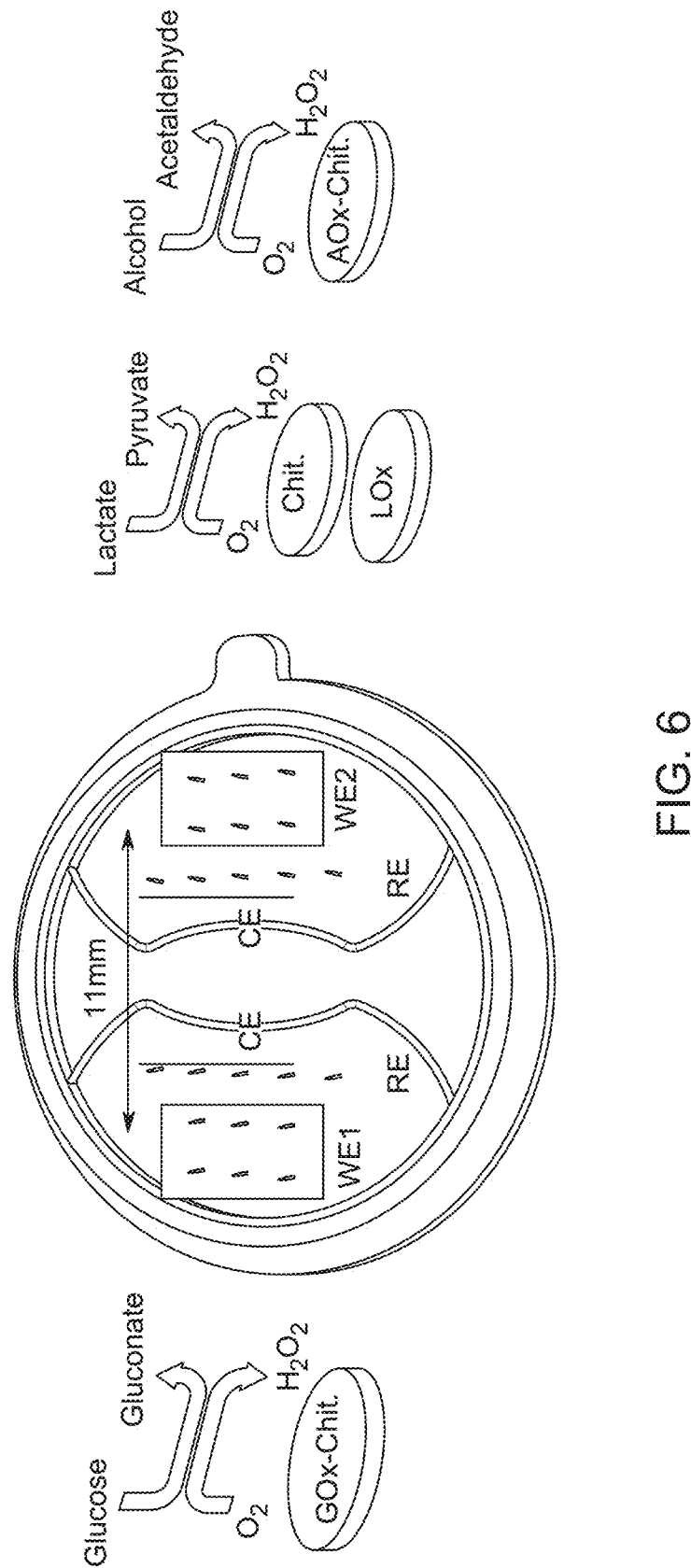
FIG. 6 shows a diagram depicting a multiplexed sensor design for measuring specific analyte parameters in continuous monitoring of glucose/lactate and glucose/alcohol.

FIG. 6 shows a diagram depicting a multiplexed sensor design for measuring specific analyte parameters in continuous monitoring of glucose/lactate and glucose/alcohol. Example implementations were performed using an example sensor like that in FIG. 6, which demonstrated a cross-talk-free wearable microneedle sensor patch device capable of simultaneous, multiplexed sensing of multiple subdermal analytes with spiked microneedle structures on a substructure with spacing (between target analyte 1 and target analyte 2 sensor regions) of at least 5 mm. For example, the example spiked microneedle sensor patch device as configured to provide two working electrode sensor regions with identical detection mechanisms, such as oxidase-based sensors (which rely on $H_2O_2$ as the sensing molecule). The sensor patch device was able to provide a mitigated sensor sensitivity range of at most 10 nA/mM for each sensing region. The sensor patch device was also configured for use of common or an individually addressable auxiliary/counter electrode(s), and for use of common or an individually addressable reference electrode(s). Also, in these example implementations, a sealing cover with at least two embedded non-intrusive skin insertion enhancing rings or ring-like elevated surfaces was used. Glucose-Lactate continuous measurements were demonstrated, along with Glucose-Alcohol continuous monitoring. Example results and techniques in these example implementations are discussed later in this patent document, in detail. It is notable that this example multiplexed design/strategy can be readily generalized and expanded for more than two target analytes and to any type of biomarkers such as metabolites, electrolytes, drugs, hormones, proteins, and oligonucleotides.

Figure 7:
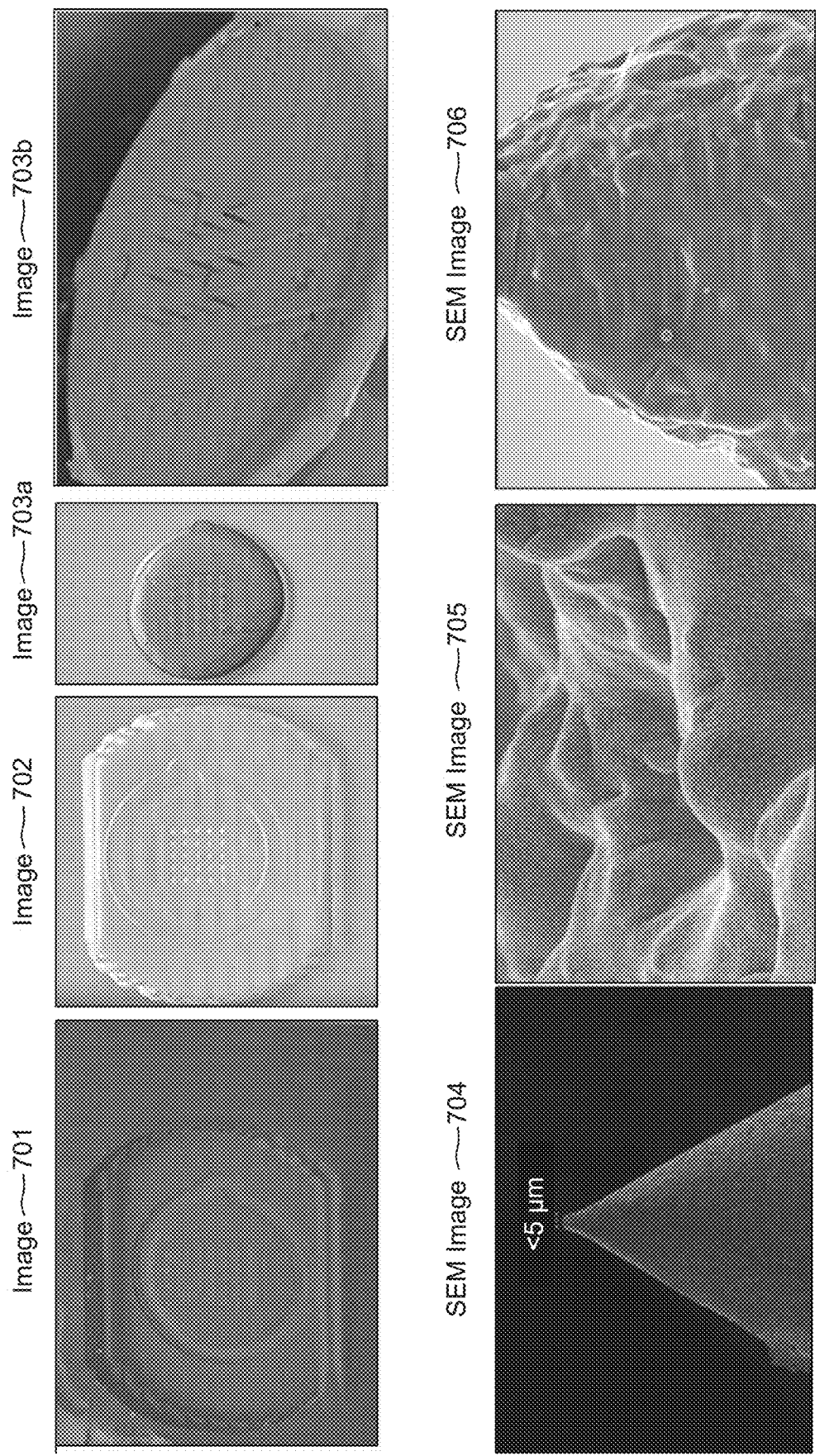
FIG. 7 shows images illustrating interim and final components produced by an example implementation of a micro-CNC fabrication method in accordance with the present technology.

FIG. 7 shows images illustrating interim and final components produced by an example implementation of a micro-CNC fabrication method in accordance with the present technology. Image 701 shows a CNC-fabricated array of spiked microneedle structures on a substrate. Image 702 shows a polydimethylsiloxane (PDMS) negative of the array in image 701. Images 703a and 703b show a replica of the spiked microneedle array in image 701, which was fabricated using micro-casting. SEM image 704 shows a zoomed view of the tip of a spiked microneedle structure in images 703a, 703b, and SEM images 705 and 706 show ultra-zoomed views of the spiked microneedle structure, which demonstrates the nanoscale or microscale roughness (e.g., 500 nm-5 µm) of the CNC-fabricated spiked microneedle structure surface, as well as the nanoscale precision of the method.

The example spiked microneedle arrays shown in FIG. 7 were implemented by non-adhesive, micro-casting, micro-machining, injection molding, ultra-high resolution 3D printing, and/or precision drawing microneedle fabrication method using polymer-based materials, in accordance with the present technology. The fabrication method is a highly scalable, inexpensive, and highly reproducible micro-casting technique for manufacturing spiked microstructure arrays. In this method, a non-adhesive polydimethylsiloxane (PDMS) negative of a spiked microstructure array is prepared utilizing a micro-computer numerical control (micro-CNC) method to create a PMMA block, e.g., using the developed strategy, tooling and machining sequence. Next, a custom-developed, biocompatible, FDA grade, photo-curable resin is poured into the PDMS negative to form the final spiked microstructure array, followed with multiple post processing steps.

Notably, in the course of refining this technique, there were a few key parameters regarding the post-processing of the photo-curable resin polymer that were found to solve the common problems of low-temperature casting methods. For example, these problems include the incomplete filling of the resin, low resolution and lack of forming a nanoscale surface roughness, usual adhesion problems between the mold and the final microstructure, lack of tip sharpness, gas bubble formation and other issues-all of which are successfully addressed by the use of the newly developed polymeric photocurable resin with optimal characteristic, as well as manufacturing process parameters tailored to the custom-made resin.

In some embodiments of the polymeric photocurable resin material, for example, the resin was prepared to an optimal viscosity by addition of nonionic surfactant (e.g., Triton X-100, in a concentration range of 0.1-1 wt %) to a biocompatible polymer, which included a biomedical-grade photocurable polymer resin. The surfactant additive, along with thermal treatment of the polymer mixture (e.g., at 65° C. for 20 min), resulted in enhancing the flowability (e.g., by reducing viscosity and enhancing surface energy) of the resin and led to nanoscale resolution of the method, without affecting the photo-crosslinking process and mechanical robustness of the finished material.

Notably, using the polymeric photocurable resin material in the fabrication method, the final manufactured spiked microneedle structures showed excellent solvent compatibility against both organic and inorganic harsh solutions, such as acetone, isooctane, ethanol, bleach, concentrated NaOH and HCl solution, hydrogen peroxide (3%) and saline water (3.5% NaCl), even up to 24 hours. Furthermore, manufactured spiked microneedle structures have demonstrated a remarkable compatibility to sterilization methods (e.g., Gamma radiation, ethylene oxide, autoclave treatments up to 125° C. for an hour, or UVc treatment). The disclosed fabrication method identified manufacturing process parameters that mitigate various problems, like incomplete filling, bubble formation, and low resolution, by combined use of the customized low-viscosity resin material, vacuumed pouring of the custom resin at an elevated temperature (e.g., 70° C. for 6 hours) followed by UV curing (e.g., 90° C. UV curing for 90 minutes). The example results produced a Nanometer-precision replica with superior mechanical fracture toughness, e.g., with <5 microns of tip sharpness as shown in FIG. 7.

Several example implementations are described below that demonstrate example embodiments of the wearable, non-intrusive microneedle sensor technology providing unique advantages based on the structural design, functional achievements, and unique methods and materials for fabrication and functionalization layer immobilization, while keeping the highest level of biocompatibility, mechanical robustness, reproducibility requirements, sensor sensitivity and selectivity requirements, and longevity for continuous analyte (or multi-analyte) on-body sensing.

Example Implementations with Continuous, Real-Time Monitoring of Single and Multiple Analytes Including Glucose, Lactate, and Alcohol Via a Fully Integrated Wearable Microneedle Platform Wearable sensors capable of monitoring biochemical markers are poised to help enable a new revolution in personalized healthcare, telehealth, and early disease diagnosis. Among potential biomolecular sampling biofluids accessible via wearable sensors, interstitial fluid (ISF) has the closest composition to the blood, with temporal profiles of most analytes approaching those observed in blood. In addition, direct ISF measurements are not affected by major issues common to other biofluids such as long lag times, variable secretion rates, sample contamination and dilution, and most importantly limited correlation, all of which greatly limit the sensor's clinical utility. Microneedle (MN)-based sensing technologies provide pain-free, and non-intrusive continuous access to constantly revitalizing ISF.

In the discussion below, presented are example embodiments of a fully-integrated, non-intrusive, and wearable microneedle sensor platform that includes reusable and disposable contingents and utilizes a biocompatible array of microneedles fabricated via an advanced micro-machining technique. The disclosed microneedle sensor platform is optimized for real-time, continuous, and multiplexed biomolecular measurements on freely behaving human subjects. This platform addresses multifaceted challenges in the areas of system integration, fabrication, packaging, biocompatibility and sterilization, skin penetration, sensitivity and stability, and low-power yet real-time biosensing in an inexpensive manner.

In example implementations of some embodiments of a fully-integrated, non-intrusive, wearable microneedle sensor array device, which includes two components of a reusable electronics and a disposable sensor, the device showed remarkable ability in tracking the dynamic profiles of key metabolites (e.g., lactate, glucose, and alcohol) during common daily activities via a small, wireless-enabled wearable, with results well correlated to gold-standard metrics. The multiplexed sensing potential of the platform is also demonstrated through simultaneous on-body monitoring of lactate-glucose and alcohol-glucose, along with the demonstration of a custom designed smartphone app for data capture and visualization. The example system is believed to mark a major new milestone for continuous, real-time, and accurate monitoring of clinically relevant biomolecules, and presents a major leap forward for next-generation wearable health monitors.

By nature of being attached to the body, wearable sensors offer the ability to continuously monitor physiological parameters in real-time on freely behaving subjects, providing interesting new insights into human health and wellness not offered by spot measurements taken in the clinic or by point-of-care devices. Merging wearable sensors with rapidly growing "omics" technologies, internet of things (IoT) devices, and artificial intelligence (AI), can potentially offer revolutionary advances in personalized healthcare, early disease detection, telemedicine/remote monitoring, personalized nutrition or wellness, or even detection of symptoms associated with COVID-19 or other viral infections.

Yet, most commercial wearables monitor only a handful of physical parameters, such as heart rate and motion, which offer only generic physiological insights. To address this issue, recent efforts have shifted to wearable devices that can detect in real time molecular markers on the skin surface through electrochemical analysis. State-of-the-art, non-invasive chemical sensor research has mainly revolved around epidermal sensors utilizing stimulated sweat or extracted interstitial fluid (ISF). However, both these skin-worn sensors still face significant challenges, including how to continuously access to the biofluid (e.g., via exercise or electrical stimulation), fluctuating flow rates, varying parameters (e.g., sweat pH, salinity, and temperature), sample mixing, carry-over, dilution, or contamination. These challenges, along with the limited correlation of some sweat biomarkers to gold-standard blood assays, and significant lag time, require considerable research efforts towards making these epidermal platforms clinically viable.

Instead of analyzing biochemical markers on the surface of the skin, analysis under the skin—directly in ISF—provides a well-established, high degree of correlation with blood for many biomarkers of interest. In fact, continuous glucose monitors (CGMs), approved for use by the US Food and Drug Administration (FDA) for diabetes management, sense glucose in ISF with excellent correlation to blood. However, current CGMs presently rely on invasive needle-based sensors, and are limited to measuring only a single analyte.

In contrast, microneedle (MN) technology, hailed recently by Scientific American and the World Economic Forum as the top emerging technology for shaping the future of healthcare, utilizes micron-sized needles that penetrate the skin by only a few hundred microns to offer a pain- and discomfort-free way of accessing ISF, obviating the need for 5-11 mm long needles common to CGMs. In addition, the limited single-analyte sensing capability of current CGM devices is readily addressable in MN platforms by utilizing multiple individually-addressable spatially-isolated sensing electrodes on a single platform, which allows for significant new detection opportunities. The micron-scale nature of the MN sensors allows for their application on multiple locations on the body, making it adaptable to different form factors such as rings, and epidermal patches. Despite the tremendous opportunities offered by MNs, the realization of their full potential for practical wearable chemical sensing has remained an unmet challenge, reflecting primarily the multidisciplinary nature of these challenges that calls for a holistic approach in reliably addressing them.

As described below, an example of a fully integrated, wirelessly-operated spiked microneedle platform for continuous monitoring of ISF biomarkers is demonstrated on human subjects. Example embodiments and implementations are described illustrating the present example of the disclosed microneedle sensor device technology.

Figure 8:
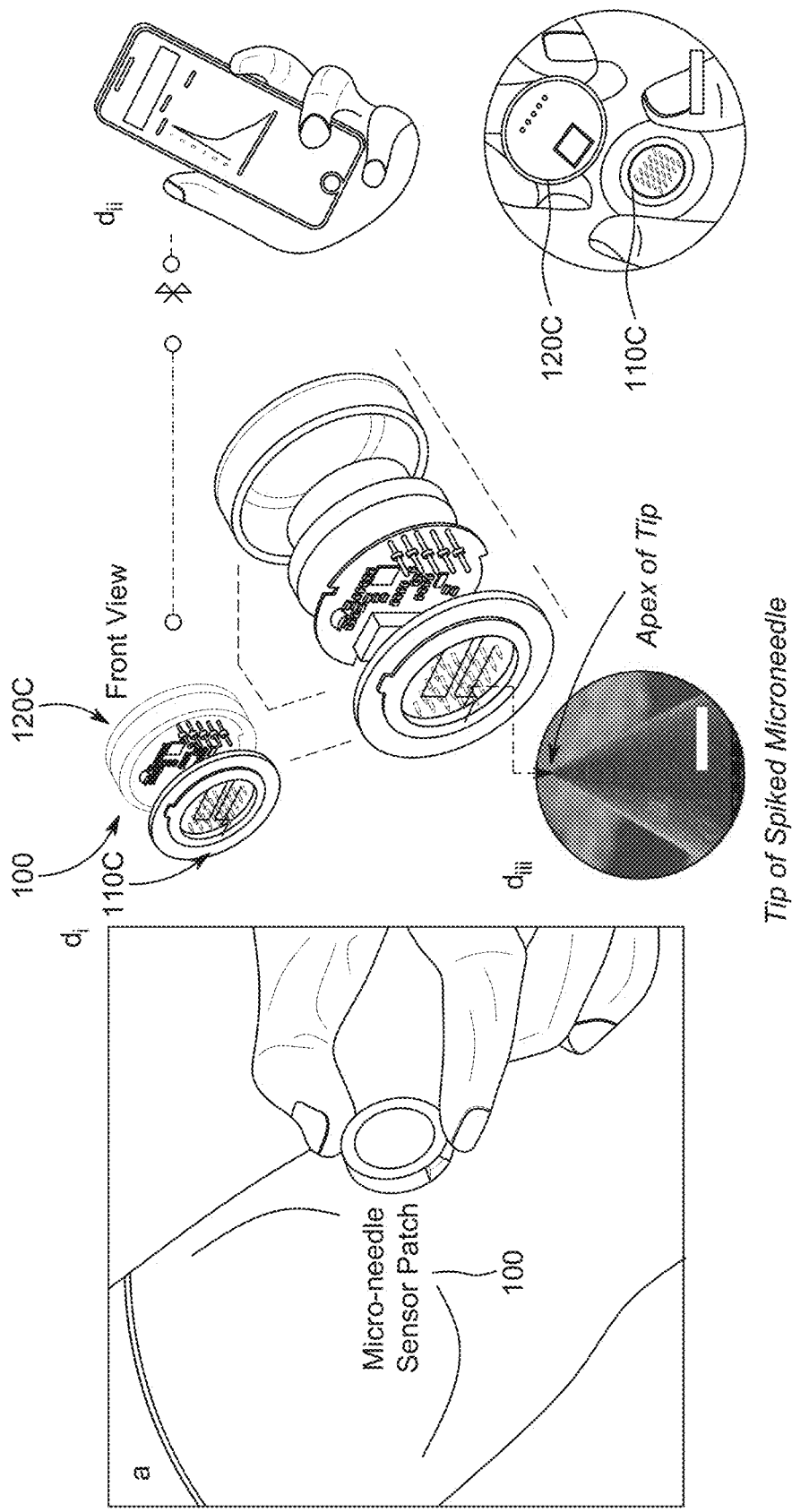
FIG. 8 shows a diagram of an example embodiment of a fully-integrated, non-intrusive, wirelessly-operated, wearable microneedle sensor patch device shown in FIGS. 1B-1D.

FIG. 8 shows a diagram of an example embodiment of a fully-integrated, non-intrusive, wirelessly-operated, wearable microneedle sensor platform in accordance with the example embodiment of the wearable, non-intrusive microneedle sensor patch device 100 shown in FIGS. 1B-1D. As shown in FIG. 8 (left panel (a)), a skin-wearable sensor system can include the wearable, non-intrusive microneedle sensor patch device 100 that continuously collects rich molecular data to facilitate greater understanding of the body's response to daily activities. Real-time monitoring of ISF biomarkers (e.g., glucose, lactate, alcohol, ketone bodies, sodium, and other analytes) is achievable, with glucose, lactate, and alcohol demonstrated in example implementations for both individually (single analyte) and simultaneously (multiplexed), with results well correlated to those of the corresponding gold standard (blood or breath) measurements over a prolonged duration. To achieve this, multifaceted challenges in the areas of system integration (e.g., sensor, electronics, firmware, and mobile app development), fabrication, skin penetration, and stable, accurate, and cross-talk-free biosensing, are successfully addressed through a holistic approach which is elaborated below.

As illustrated in FIG. 8, a fully integrated spiked microneedle sensor system, which can include an array of multiple sensors and custom electronics, was designed, fabricated, developed, and tested. The integrated system can include distinct sub-components (e.g., shown previously in FIG. 1C), which are assembled into two primary components-disposable sensor component 110C and reusable electronics unit 120C. Right-side panel (d) of FIG. 8 shows multiple schematics and images depicting how the example device 100 allows for convenient replacement of the low-cost disposable sensor component 110C according to its functional life. Molecular level electrochemical signals from the wearer's ISF are continuously and selectively gathered by the epidermis-inserted spiked microneedle tips (FIG. 8, panel ($d_{iii}$), showing an SEM (scale bar: 75 µm) of a tip structure of a spiked microneedle), which the signals are carried through the low-noise, reusable sensor-electronics (reusable electronics unit 120C) through a physical interface between disposable sensor component 110C and reusable electronics unit 120C, and which can be wirelessly transmitted to the mobile device 130 for remote data processing, e.g., via a software application (app) executable on the mobile device 130 (FIG. 1A and FIG. 8, panel ($d_{ii}$)), e.g., for visualization and analysis of the real-time monitoring of analytes. The entire operation can be wirelessly controlled by the accompanying app.

Figure 9:
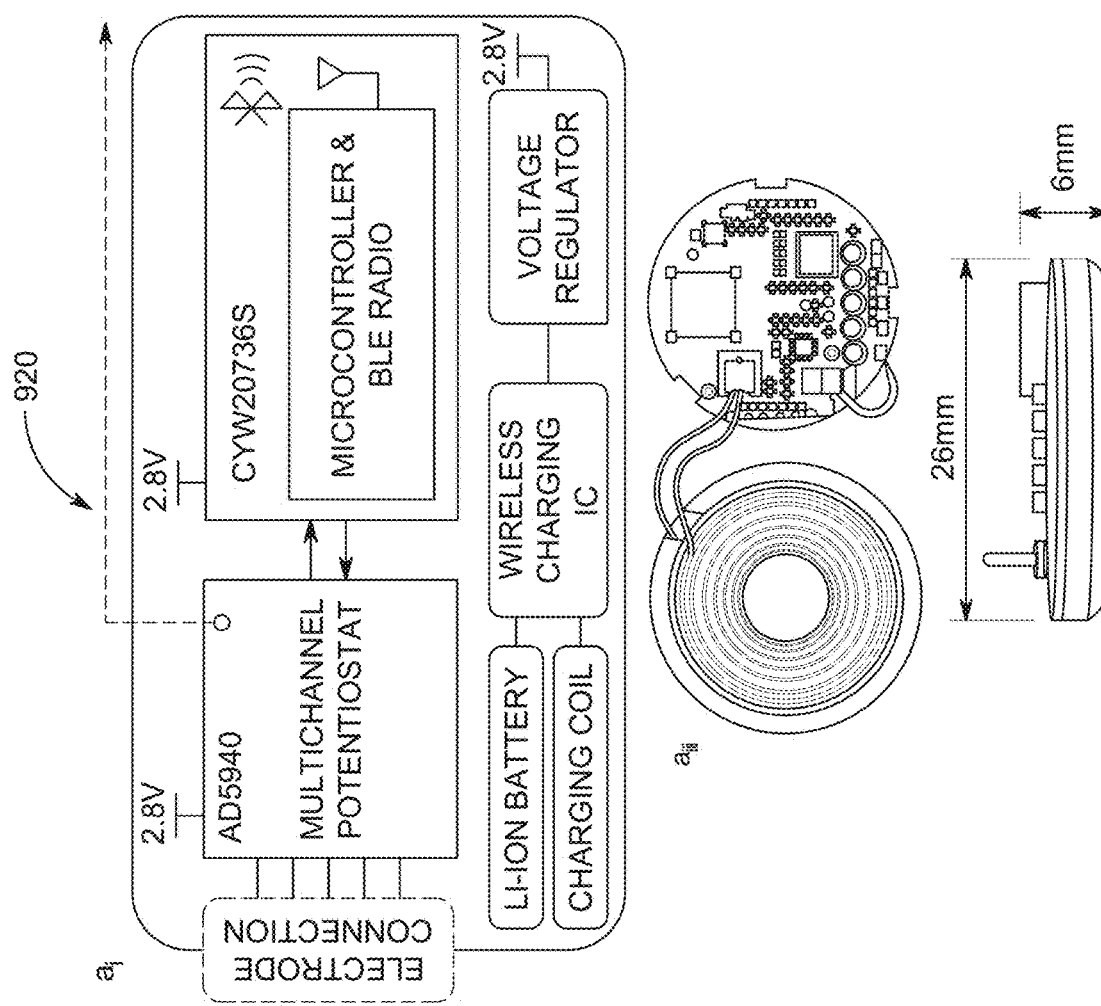
FIGS. 9-11 show schematics and images depicting an example embodiment of a disposable sensor component and a reusable electronics unit of the example wearable microneedle sensor patch device shown in FIG. 8.
Figure 9:
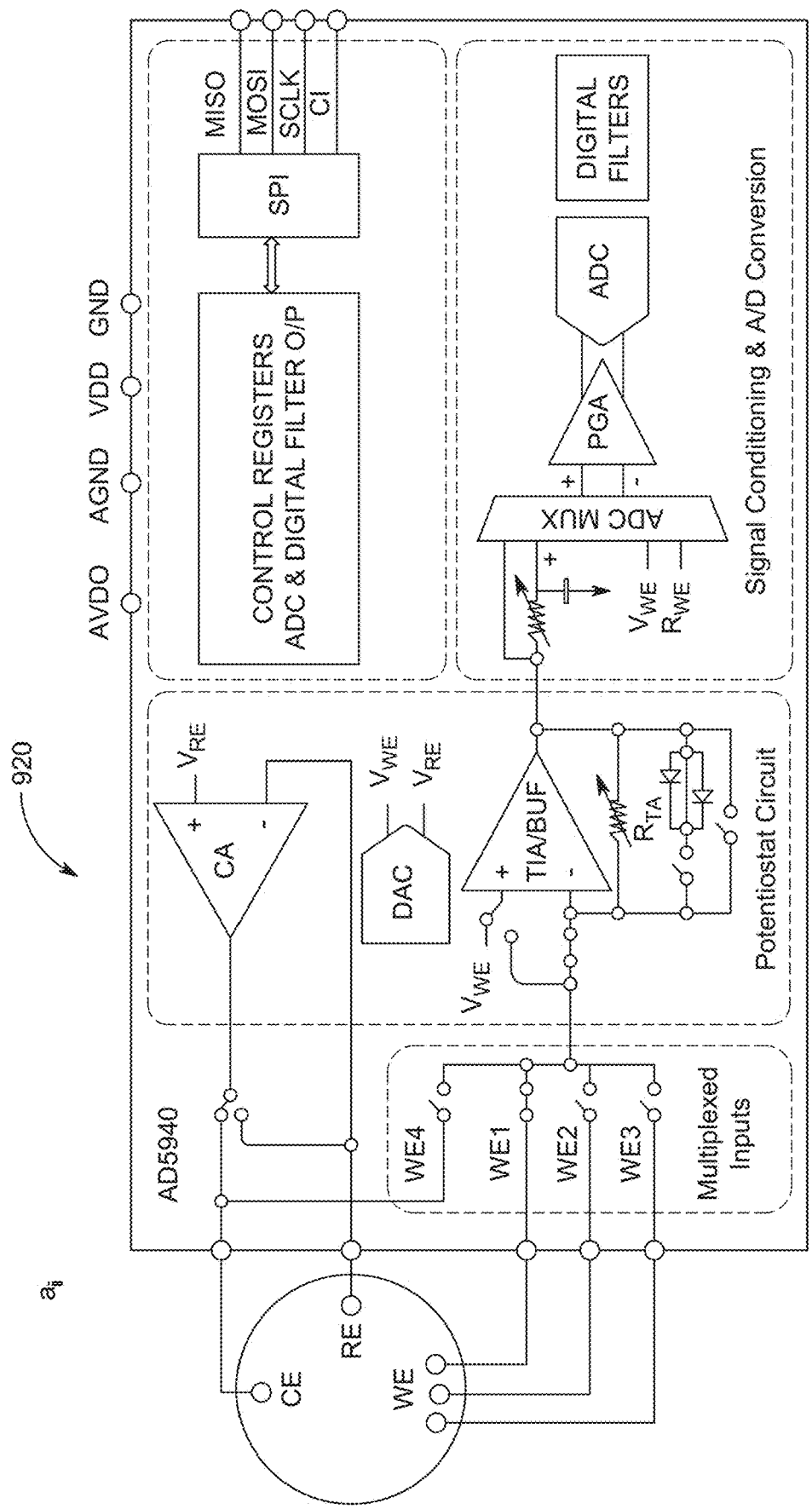
Figure 9:
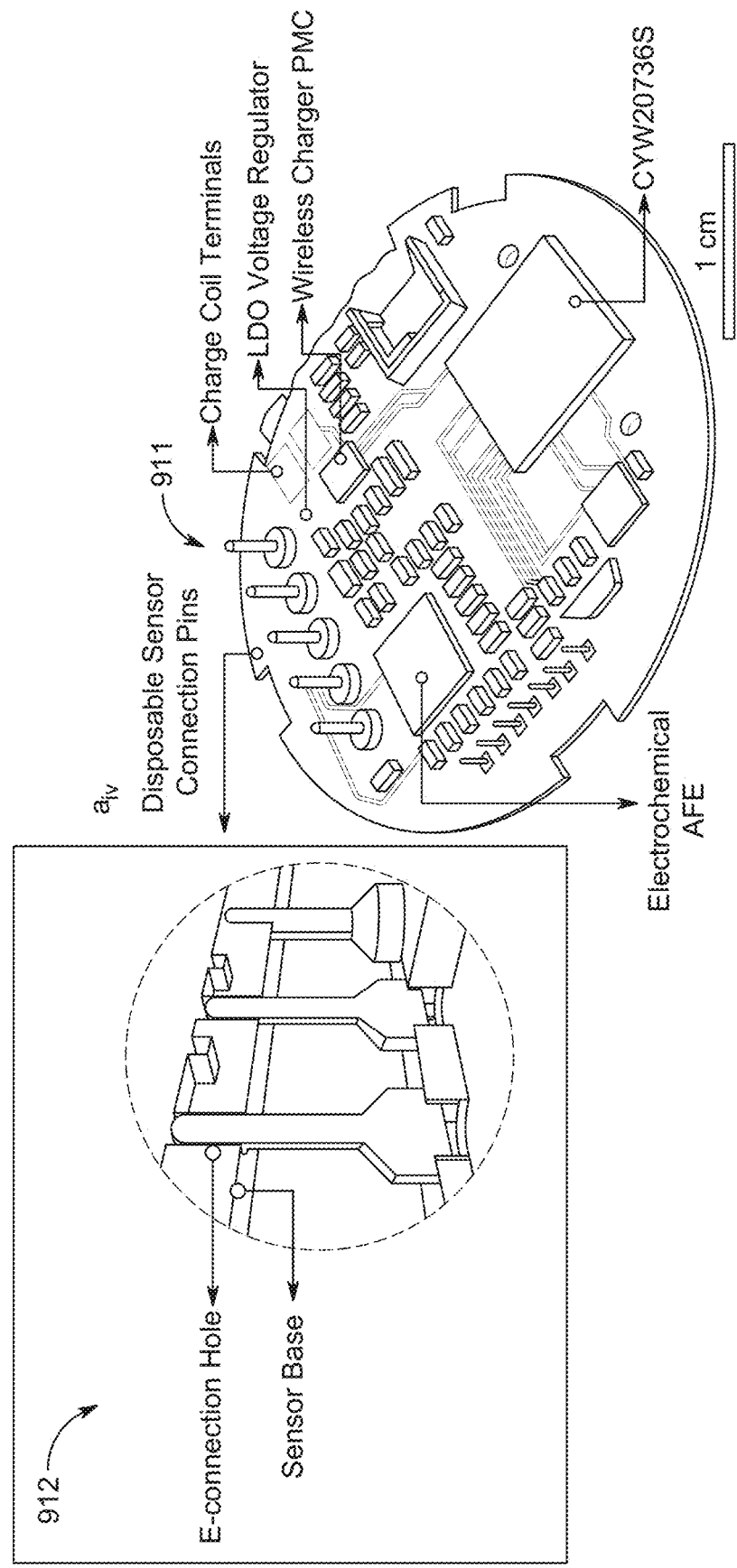
Figure 10:
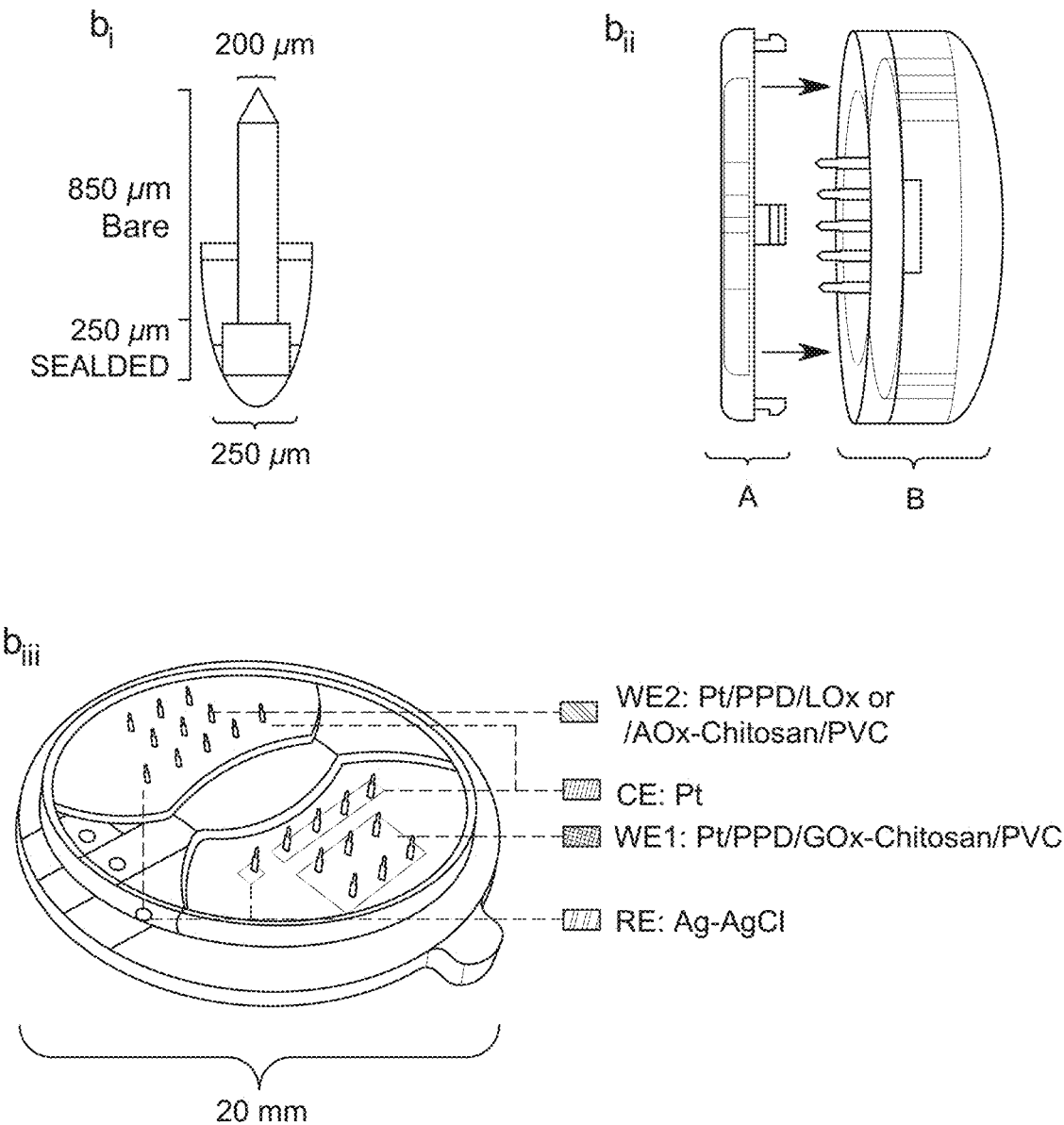
Figure 11:
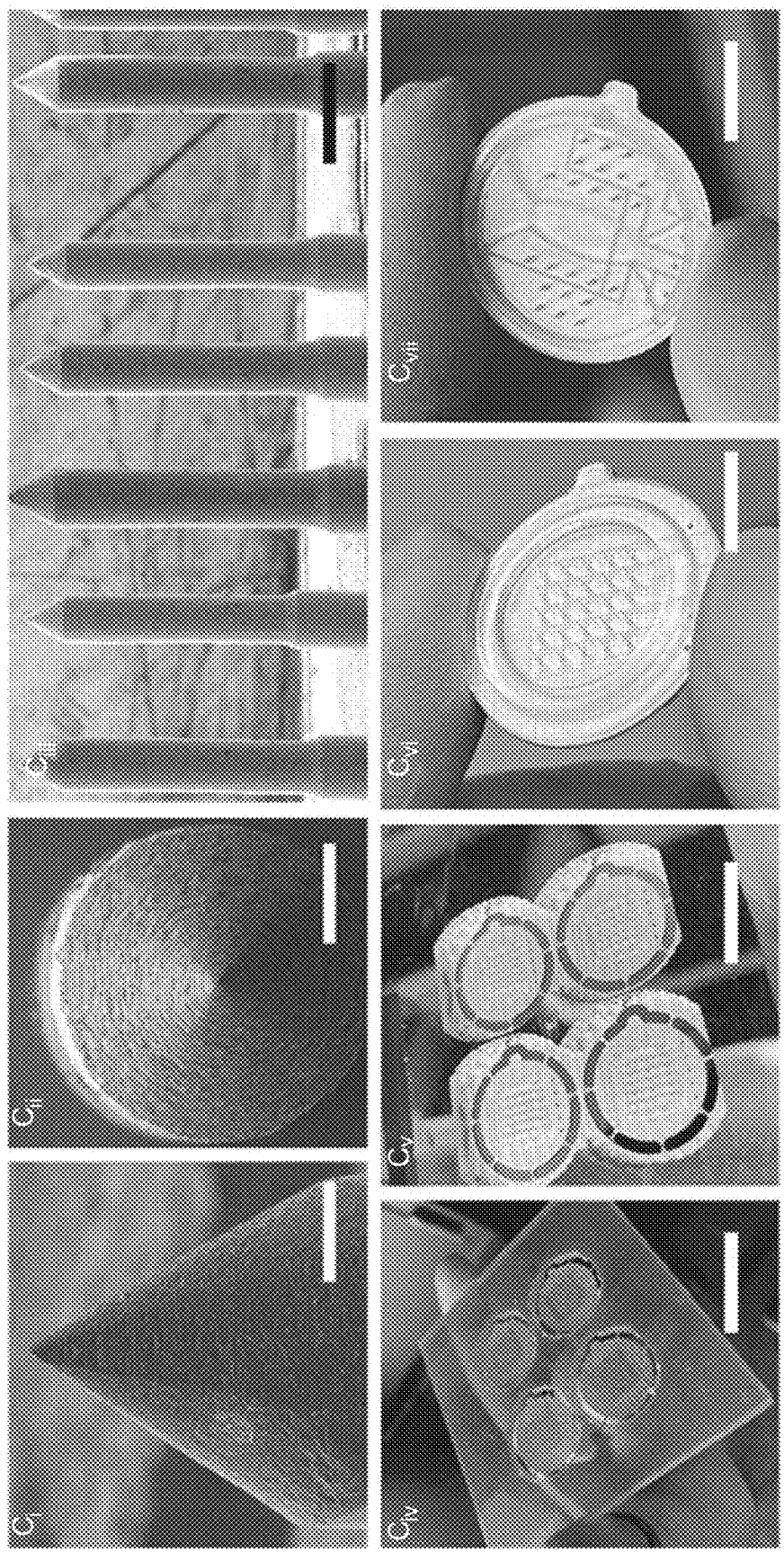

FIGS. 9-11 show schematics and images depicting an example embodiment of the disposable sensor component 110C and the reusable electronics unit 120C shown in FIG. 8, e.g., used in the example implementations. FIG. 9 shows schematic diagrams illustrating the example electronics and sensor architecture for the disposable sensor component 110C and the reusable electronics unit 120C, labeled 920C in FIG. 9, where panel ($a_i$) shows a functional block diagram of example components in an architectural configuration of the reusable electronics unit 120C; panel ($a_{ii}$) shows an abridged functional block diagram of an example AD5940 electrochemical AFE (recreated from the component's datasheet); panel ($a_{iii}$) shows an image depicting an example of the electronic system PCB connection to a battery (e.g., through a low-profile connector) and to the charging coil (e.g., through large solder pads); and panel ($a_{iv}$) shows a diagram showing example components of the reusable electronics unit 120C, including example electronic interface connection pins 911 and a break-out diagram 912 demonstrating how the disposable electronic unit 120C interfaces to the disposable sensor component 110C (i.e., spiked microneedle array 171) via the connection pins 911—which, in this example, insert into conductive holes ("E-connection Hole" in the diagram 912) on the sensor base (e.g., where such holes can be made conductive by sputter deposited metal within CNC milled holes), and where mechanical guides at the base of the conductive pins 911 provide mechanical retention to the example electronic system PCB. FIG. 10 shows illustrations of an example individual microneedle (with corresponding dimensions for the particular example) in panel ($b_i$), a side-view depiction of an example embodiment of the disposable sensor component 110C and reusable electronics unit 120C in panel ($b_{ii}$), and a perspective-view depiction of an example multiplexed spiked microneedle sensor with microneedle groups configured as two separated working electrode arrays with corresponding counter and reference electrodes, in panel ($b_{iii}$). The example shown in FIG. 10 panel ($b_i$) shows a spiked microneedle with a bare extending body; whereas in other examples (such as FIG. 2A), the spiked microneedle can include a winding protrusion (also referred to as a winding projection), such as the example winding spiral protrusion 112 in FIG. 2A. FIG. 11 shows SEM images showing side- and top-view of an individual microneedle tip (scale bar of 100 µm) in panels ($c_i$) and ($c_{ii}$), a SEM image of multiple microneedles (scale bar of 500 µm) in panels (c$_{iii}$), images of a batch of four micromachined spiked microneedle arrays before after sputtering of thin film metals (scale bar: 2.5 cm and 2 cm, respectively) in panels (c$_{iv}$) and (c$_i$), and images of an assembled microneedle-cover ring for single and multiple sensing, respectively (scale bar of 1 cm) in in panels (c$_{vi}$) and (c$_{vii}$).

The schematics and images in FIGS. 9-11 demonstrate an example embodiment of the disclosed wearable, non-intrusive microneedle sensor patch device 100, designed for functionality, compactness, and low power operation. For example, to acquire electrochemical signal data and subsequently transmit it, the example reusable electronic unit 920 of the device in FIGS. 9-11 utilizes two integrated circuits: an electrochemical analog front end (AFE) and a Bluetooth Low Energy (BLE) system-in-package (SiP). In this example, the AFE provides the circuitry for multiplexing between up to four independent working electrodes, signal conditioning (amplification and filtering), and signal digitization, while the BLE SiP provides a low power microcontroller for processing the digitized signals, as well as a BLE radio and embedded antenna for data transmission. Powering these components, in this example, is accomplished by a lithium-polymer battery (through a voltage regulator), which is inductively charged through a wireless charging IC and charging coil (e.g., see FIG. 15). Additionally, power optimizations for the AFE and BLE SiP enable ~30 days of battery life while maintaining a relatively small battery size (e.g., see FIG. 16). Minimizing the number of necessary ICs to only four (2 for signal acquisition/transmission and 2 for voltage regulation/recharging), in addition to the power optimizations, allow for a compact design (e.g., see FIG. 9, panel (a$_{iv}$)). Manufacturing the electronics can be intrinsically scalable, e.g., demonstrated in FIGS. 15-18.

Figure 19:
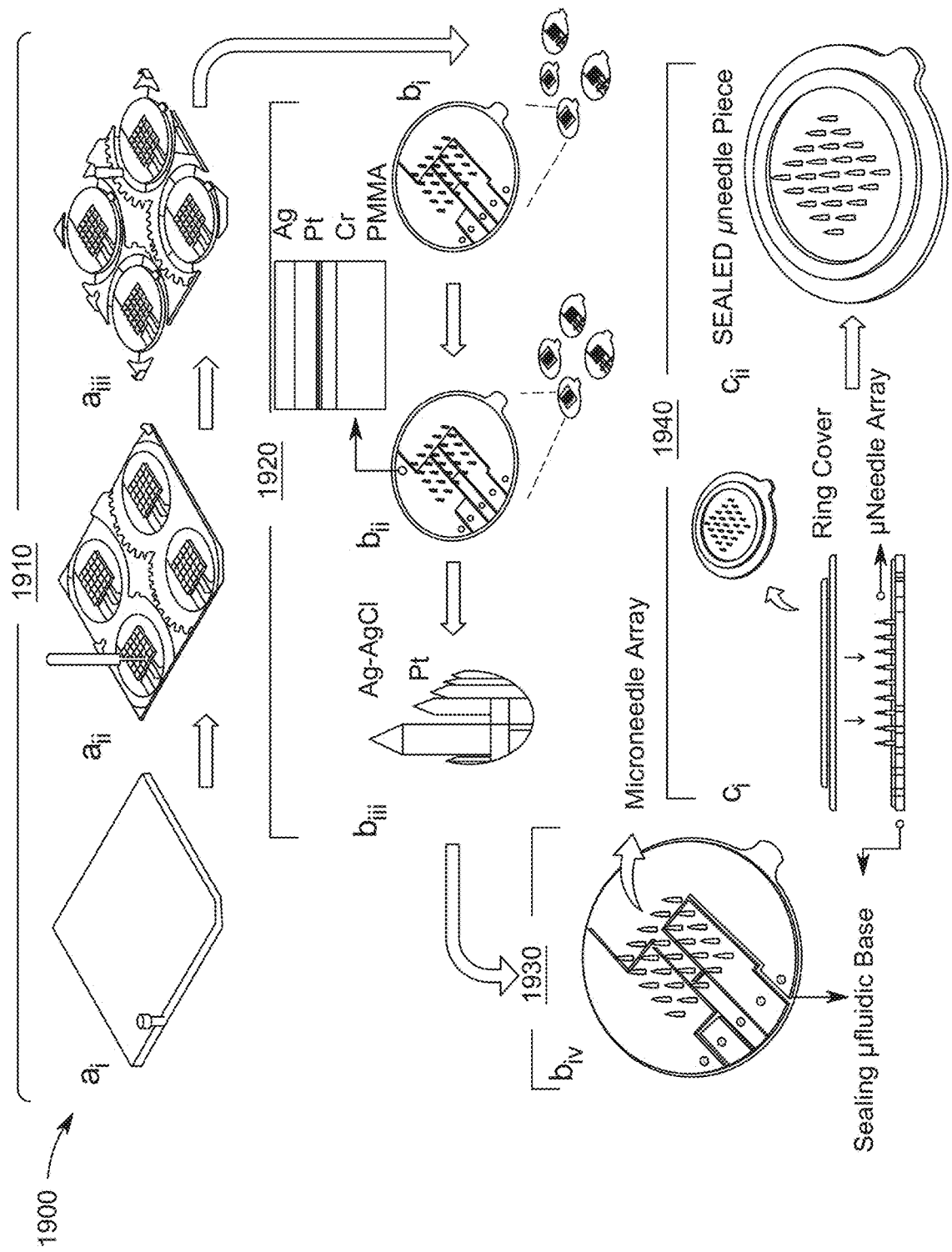
FIG. 19 shows an illustrated flow diagram of an example embodiment of a fabrication method for a spiked microneedle sensor array in accordance with the present technology.

In the example implementations, the example microneedle microelectrodes were fabricated by a scalable, tremendously cost-effective, and highly reproducible micromachining method, also disclosed herein, through transferring the 3D Computer-Aided Design (CAD) model of the optimized geometrical design to a Computer-Aided Manufacturing (CAD) file used for micro-computer numerical control (CNC) machining of the MN microelectrodes from a poly (methyl methacrylate) stock material (e.g., see the process flow diagram of FIG. 19). For the example embodiment shown in FIGS. 8-11, for example, the dimensions, geometrical shape, and configuration of the microelectrodes as well as the working-counter-reference electrode ratio (e.g., see FIG. 20) were judiciously optimized to achieve reliable mechanical robustness and maximized analytical performance while bio compatibly providing a pain-free skin penetration with a microneedle tip diameter smaller than 5 µm (e.g., see FIG. 2B and FIG. 11), where in some embodiments the spiked microneedle tip can be configured to be between 2 µm to 5 µm (e.g., see FIG. 34D), and in some embodiments the spiked microneedle tip can be configured to be smaller than 2 µm (e.g., in a range of 100 nm to 2 µm). In some embodiments, such as in FIG. 11, for example, the body region of the spiked microneedle structure having a microneedle tip diameter between 100 nm to 5 µm may not include the protrusion structure (e.g., spiral protrusion); whereas in some embodiments, such as in FIGS. 2B-3 and FIG. 34D, for example, the body region of the spiked microneedle structure having a microneedle tip diameter between 100 nm to 5 µm may include the protrusion structure, such as a spiral protrusion. Additionally, time lapse images of the human subject's arm, taken after wearing the example spiked microneedle sensor patch for five hours, showed no skin irritation or inflammation in the applied area (e.g., see FIG. 21). For the example biocompatible PMMA-based spiked microneedle array along with an example two-step sterilization protocol ensured the safe deployment of the assembled spiked microneedle sensor patch for in vivo trials on human subjects (e.g., see FIG. 22).

The example fully-integrated, wearable sensor system was utilized in example implementations for continuous monitoring of lactate, glucose, and alcohol, each of which can potentially provide unprecedented insights into the (patho)physiology of the body with multiple applications including early diagnosis, prognosis, and management of diseases. For instance, blood lactate level is the most reliable predictor of morbidity and mortality in various groups of critically ill patients with sepsis, organ failure, trauma, and/or acute inflammatory response syndrome. Continuous lactate sensing offers a significant direct benefit in guiding of early resuscitation therapies in patients with emergency health conditions, and the way these patients are treated. For example, continuous lactate sensing can also be a valuable tool for athletes to reach their maximum body performance and reduce risk of injuries (e.g., by identifying and monitoring their lactate threshold, obtained by plotting the rapidly changing lactate levels during the course of an incrementally intensifying exercise until the point of failure). Additionally, continuous monitoring of glucose is an essential part of managing diabetes for ever increasing number of people with diabetes worldwide. Furthermore, the prevalence of alcohol consumption is linked to a bevy of health complications and therefore, continuous real-time alcohol monitoring could provide functional information to early treatment of alcohol-related health complications including prevalent alcohol use disorders.

The continuous monitoring of biomolecules using the example embodiments of the spiked microneedle sensor device can be coupled with continuous monitoring of physical parameters and vital signs enabled on the same device, e.g., where the electronics unit 120 is interfaced to work with the spiked microneedle sensor unit 110 and a secondary monitoring device for continuous or intermittent monitoring of physical parameters, vital signs, or other health related information. For example, integration of lactate monitoring with heart rate on the same sensor device can enable real time monitoring of lactate threshold for athletes who are interested in optimizing their training performance. Another example includes an integrated alcohol monitoring sensor with heart rate and skin temperature sensor to understand the real time relationships among these different parameters for different groups of people during a drinking episode. Furthermore, for example, monitoring of therapeutic drugs such as levodopa along with motion sensors will enable people with Parkinson disease to accurately adjust their drug dose intake and therefore, avoiding frequent drug related on and off periods.

In the example implementations, lactate, alcohol, and glucose biosensing contingents (e.g., sensing layers) were developed on the tip of the spiked microneedles. To create the biosensing contingents on the spiked microneedles, the protocol utilized electrodepositing an innermost interference-rejecting polymer layer, poly-o-phenylenediamine (PPD), followed by immobilizing the respective oxidase enzyme intermingled in chitosan polyelectrolyte layer and finally, forming non-ionic surfactant-containing polyvinyl chloride (PVC) as the diffusion-limiting outer film. Enzyme loadings and the thickness of each polymer layer were carefully optimized to enable accurate continuous monitoring for each biomarker with excellent selectivity and stability while mitigating biofouling and 'oxygen-deficiency'. Prior to in vivo testing on human subjects, the in vitro analytical performance of each biosensor was investigated in an artificial ISF solution, and results verified their excellent performance in detecting each target biomarker within physiologically relevant concentration ranges, stably and selectively (e.g., see FIG. 23B).

Figure 12A:
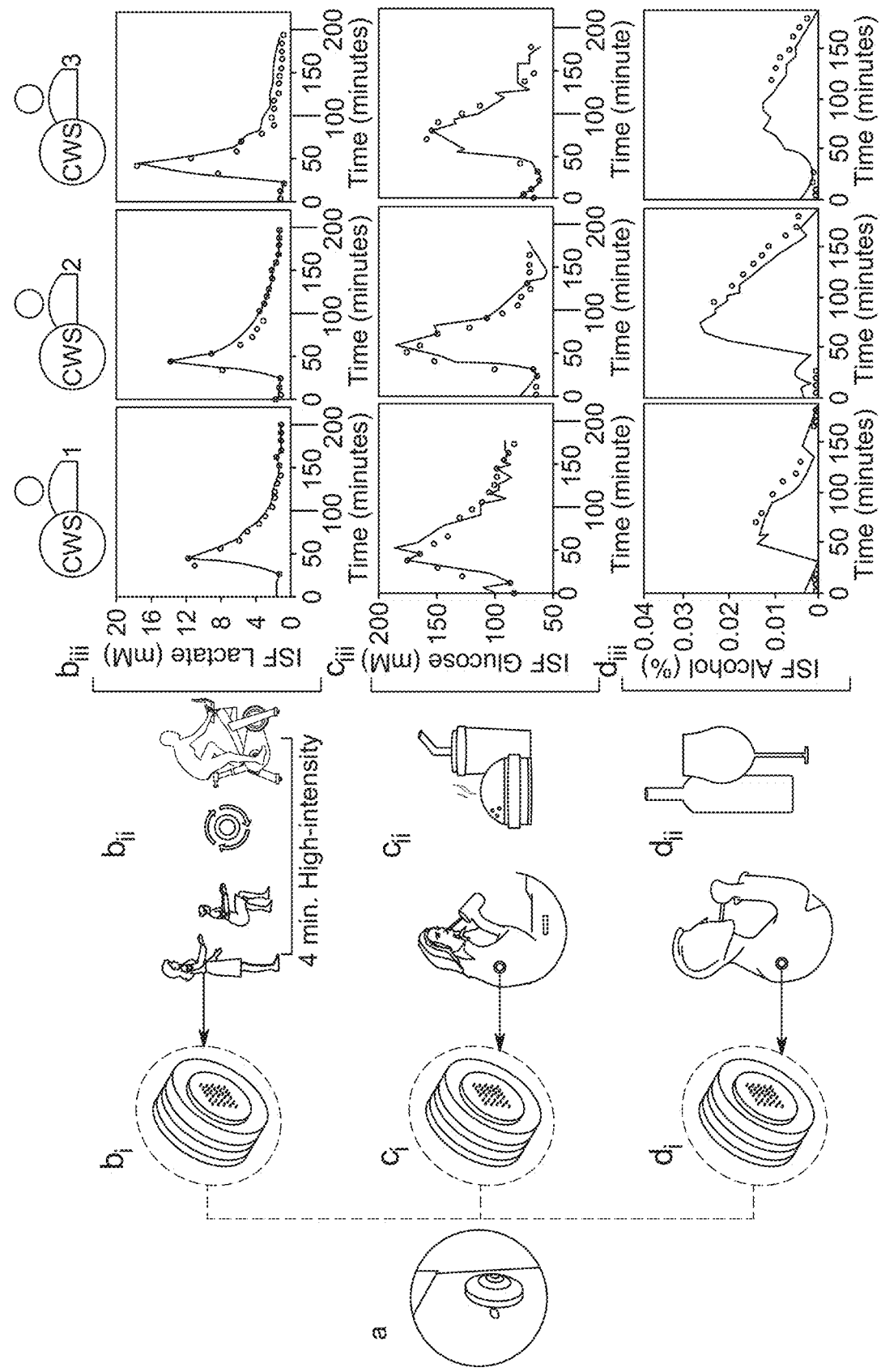
FIGS. 12A and 12B show diagrams and data plots from example on-body performance implementations of an example spiked microneedle array biosensor device with a single analyte sensor in accordance with the example embodiments shown in FIGS. 8-11.
Figure 12A:
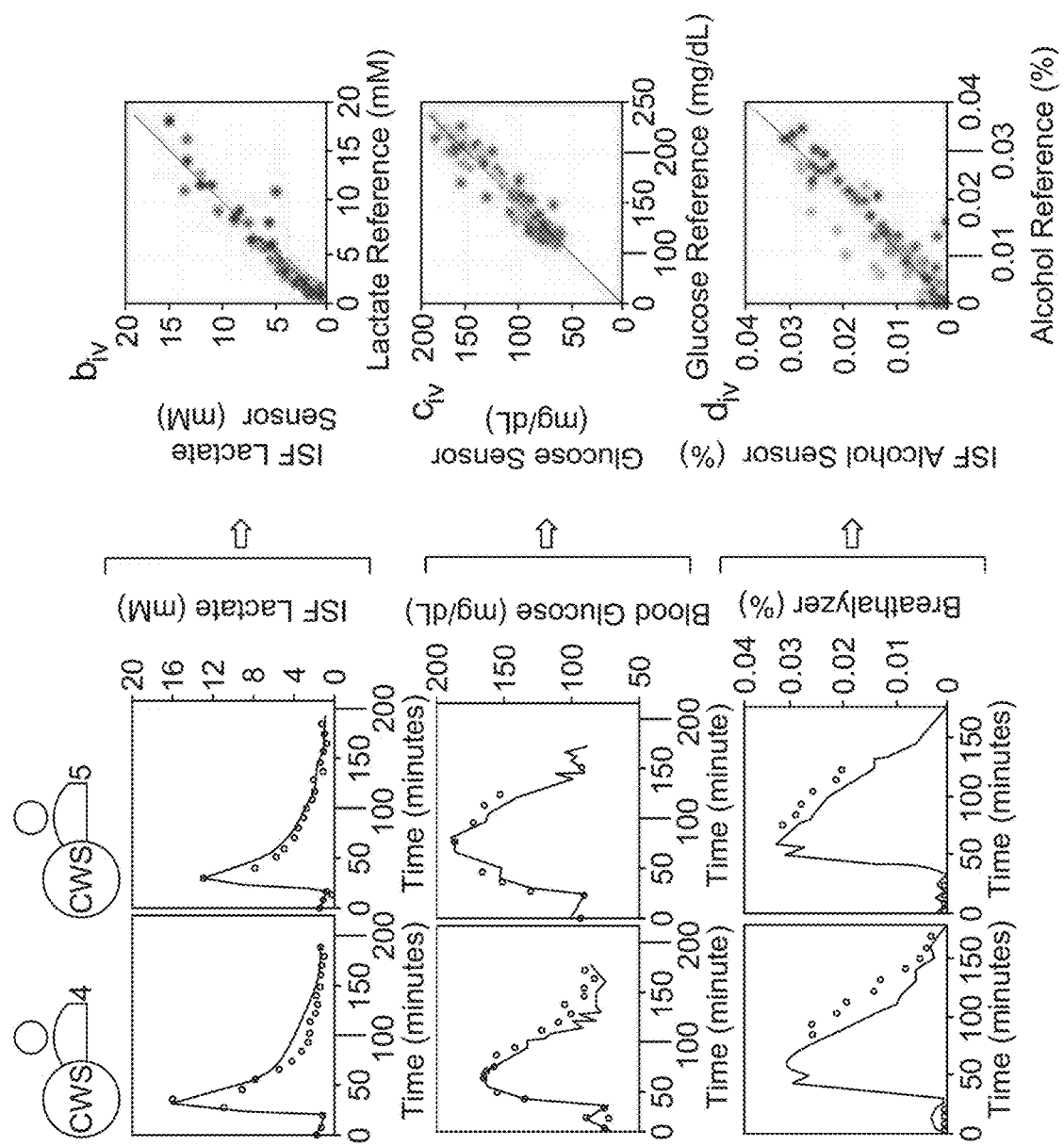
Figure 12B:
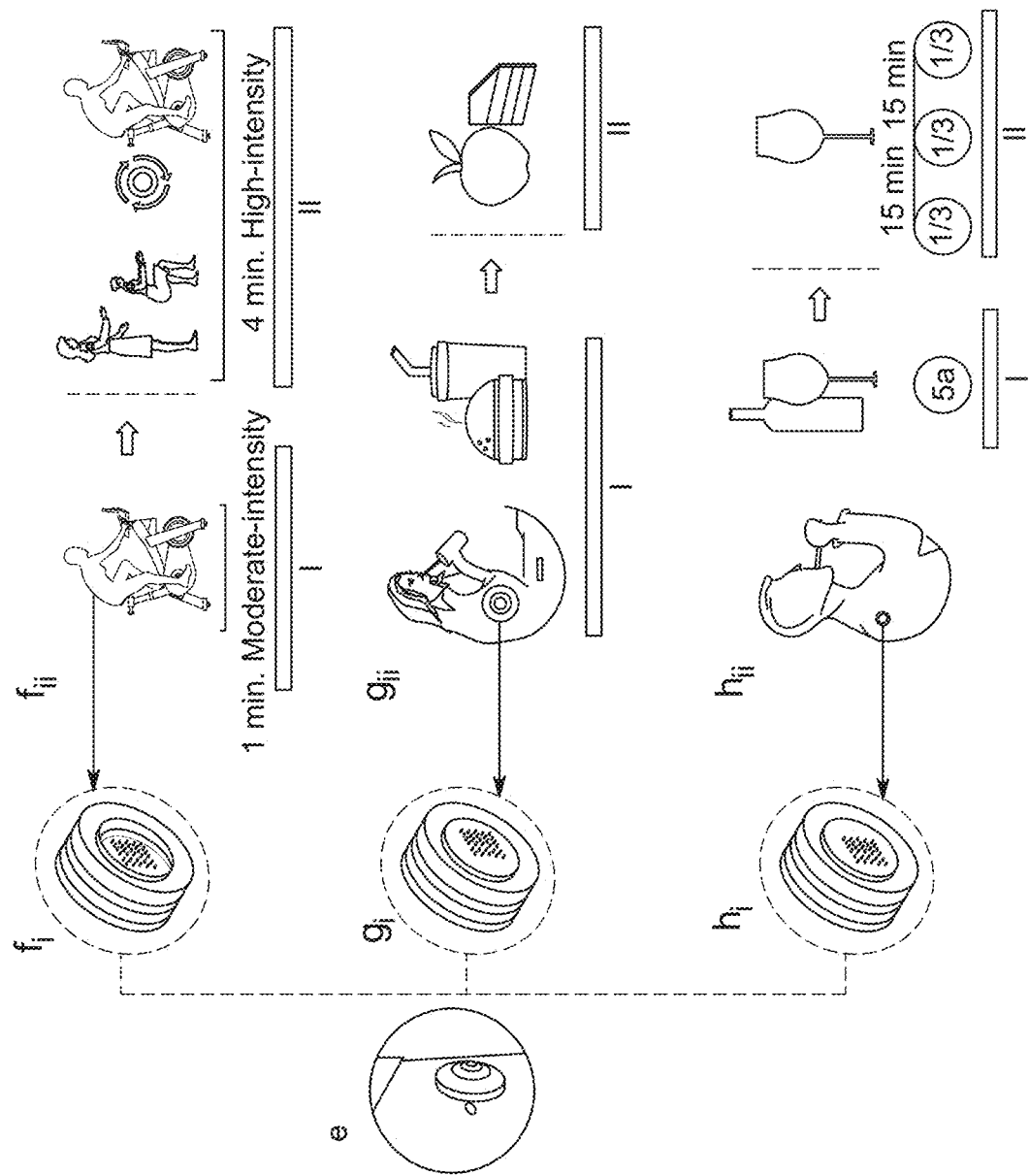
Figure 12B:
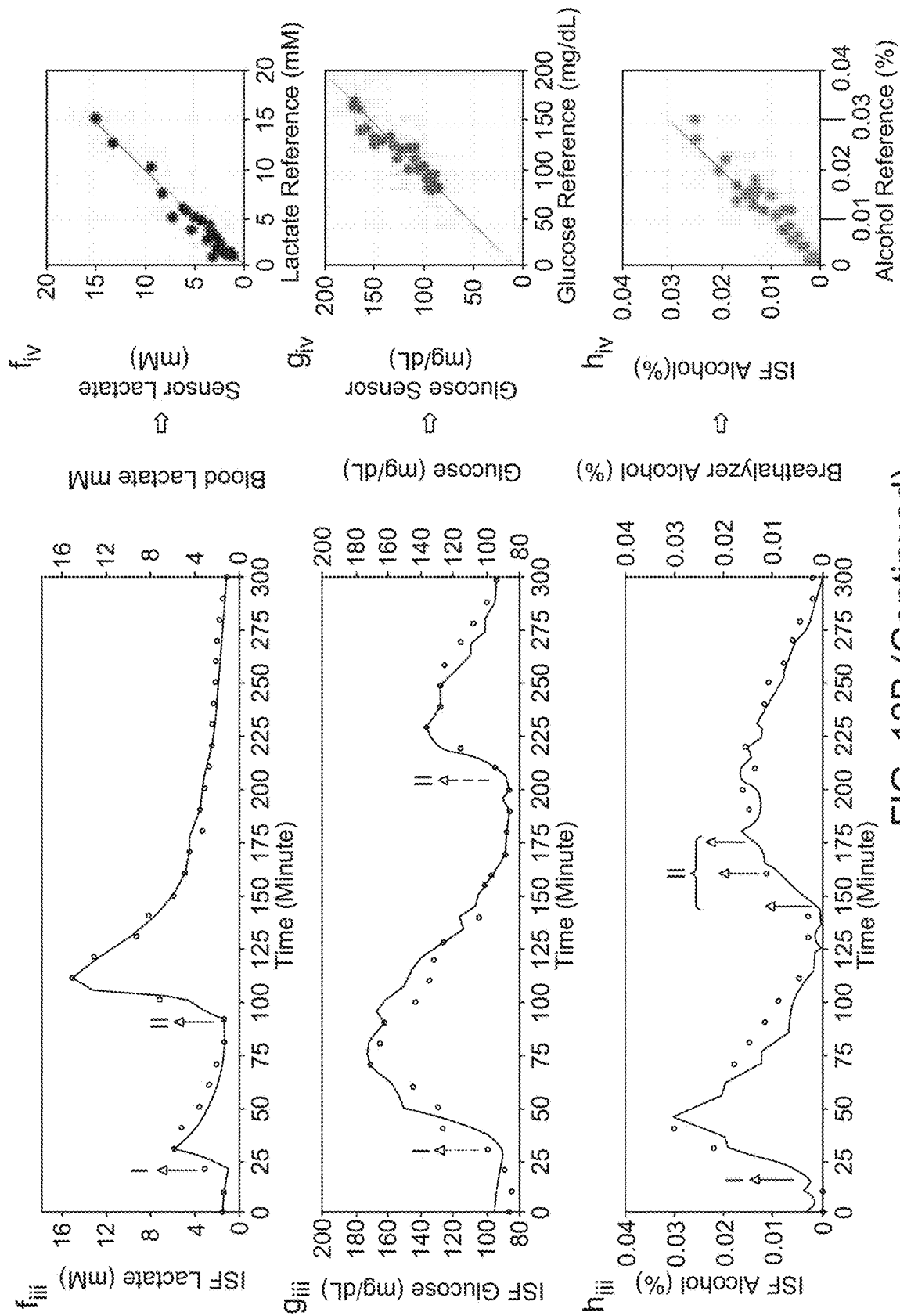

The on-body performance of the example spiked microneedle array biosensor device used in in vivo implementations is depicted in FIGS. 12A and 12B. The testing protocol included an unchanging single-event performed for each target analyte biosensor on five different human subjects (FIG. 12A, panels (a)-(d)) and varying multi-event activities performed for each biosensor on a single human subject (FIG. 12B, panels (e)-(h)). The unchanging single-event activities involved asking all the participants to follow an identical exercise protocol, consume identical meal, and an equal amount of wine, serving as triggers to induce concentration fluctuations of lactate, glucose, and alcohol, respectively, and to test the performance of the sensors. The varying multi-event activities demonstrate each sensor's performance on a human subject in response to a varying activity (e.g., from a low intensity exercise to a high intensity exercise, consuming a full meal to a dessert, and consuming a glass of wine rapidly and then gradually, respectively). The assembly of the integrated wearable sensor components and attaching it to the wearer's arm can be displayed via a software application associated with the example spiked microneedle array biosensor device, e.g., custom-designed mobile application used in the example implementations. Setup of the custom designed mobile app, alongside a signal test of a sensor on body, are presented in FIG. 24 and in FIG. 25, respectively.

FIGS. 12A-12B show diagrams and data plots depicting an example on-body performance implementation of an example spiked microneedle array biosensor device with a single analyte sensor in accordance with the example embodiments shown in FIGS. 8-11. FIG. 12A panel (a) shows a photograph of an example spiked microneedle sensor device placed on a subject's arm; FIG. 12A panels $(b_i)$-$(b_{ii})$-$(b_{iii})$ illustrate the lactate sensor performance study protocol and example data on five human subjects throughout a 4-min high-intensity exercise followed by a resting session, with corresponding lactate blood validation; FIG. 12A panel $(b_{iv})$ shows a plot of ISF lactate data measurements by the sensors vs. blood lactate reference measurements; FIG. 12A panels $(c_i)$-$(c_{ii})$-$(c_{iii})$ illustrate the glucose sensor performance study protocol and example on five human subjects following an identical meal consumption event with corresponding blood glucose validation; FIG. 12A panel $(c_{iv})$ shows a plot of ISF glucose data points by the sensors vs. blood glucose reference measurements; FIG. 12A panels $(d_i)$-$(d_{ii})$-$(d_{iii})$ illustrate the alcohol sensor performance study protocol and example data on five different human subjects throughout a wine consumption event with breathalyzer alcohol measurement validation; and FIG. 12A panel $(d_{iv})$ shows a plot of ISF alcohol data points by the sensors vs. alcohol breathalyzer reference measurements. FIG. 12B panel (e) shows a photograph of an example spiked microneedle sensor device placed on a subject's arm; FIG. 12B panels $(f_i)$-$(f_{ii})$-$(f_{iii})$ illustrate diagrams of the multi-event study of the lactate sensor throughout varying exercise session beginning with a 1 min of moderate-intensity biking $(f_{i-I})$ followed by a 4 min high-intensity squat-biking combination session $(f_{ii-II})$, along with the corresponding plot of ISF lactate measurements by the sensor vs. lactate blood strip reference measurements shown in panel $(f_i)$; FIG. 12B panels $(g_i)$-$(g_{ii})$-$(g_{iii})$ show diagrams of the multi-event study of the glucose sensor involving varying food consumption events beginning with consumption of a meal $(g_{ii-I})$, then an interval of fasting, and finally consumption of a dessert $(g_{ii-II})$, along with the corresponding plot of ISF glucose measurements by the sensor vs. blood lactate strip reference measurements shown in panel $(g_{iv})$; FIG. 12B panels $(h_i)$-$(h_{ii})$-$(h_{ii})$ show diagrams of the multi-event alcohol sensor study involving varying wine consumption events beginning with rapid consumption of a glass of wine $(h_{ii-I})$, followed by gradual consumption of the same amount of wine spread out between 15 minutes intervals $(h_{i-II})$, with the corresponding plot of ISF alcohol measurements by the sensor vs. breathalyzer reference measurements in panel $(h_{iv})$.

As shown in 12A, ISF lactate levels, monitored for each subject in 5 min intervals, rapidly rises from the background value (1-2 mM under resting) after 4 min of a high-intensity exercise, then peaks, and thereafter declines gradually to the original base value. For all subjects, the calibrated ISF lactate levels closely track blood lactate measurements (taken every 10 min) with negligible lag time (<5 min). The Pearson correlation coefficient (Pearson's r) for the two data sets was found to be 0.94 (105 paired data points), highlighting the strong performance of the wearable spiked microneedle sensor patch in accurately and continuously tracking the dynamic lactate fluctuations in the body. Highly personalized responses were observed in terms of lactate peak intensities (11.8-18.1 mM), lactate production rate (15-25 min), and its elimination rate (85-130 min). The area under the curve (AUC) for lactate was found to range from 11.27 to 14.82 mM-h. The lactate AUC can provide vital insights into severity and duration of hyperlactatemia in of critically ill patients, and it has been shown as a reliable prognostic marker of septic shock in emergency rooms. The example spiked microneedle sensor can thus potentially have a life-saving impact on septic shock patients and substantially reduce the mortality rate among these patients by enabling early diagnosis and timely feedbacks on the undergoing interventions.

Similarly, a high performance was obtained for glucose sensing for all five subjects (FIG. 12A, panel (c) series), with a mean absolute relative difference (MARD) of 8.83% (95 paired data points). Personalized responses (i.e., each subject having a unique base glucose level, peaking and decline rates) in terms of the rates of glucose uptake and glycolysis were observed. AUC analyses for glucose data produce values ranging from 220 to 304 mg-h/dL. AUC for glucose has been shown to be a more sensitive predictor than HbA1c and fasting plasma glucose levels for detecting diabetes, and impaired glucose tolerance, and identifying people at increased risk of diabetes. Accordingly, AUC analysis of the spiked microneedle sensor data suggests that subject #5 can be at an increased risk of developing diabetes.

Instantaneous response to alcohol consumption (FIG. 12A, panel (d) series) was found with the spiked microneedle sensor for alcohol sensing, beginning from the expected sober values of 0% and thereafter tracking measurements from the gold-standard breathalyzer unit with a Pearson's r of 0.94 (95 paired points). The obtained data showed a large inter-subject variability with peak values ranging from 0.012% (2.6 mM) to 0.034% (7.4 mM) and AUC values from 3.29 to 9.25 mM-h, reflecting sex-, weight-, metabolism-, and age-related differences, as well as genetic parameters among participants. Notably, for example, existing transdermal alcohol monitors, which are mainly approved for research applications, are only able to provide semi-quantitative measures of alcohol consumption. Besides, these conventional sensors suffer from major problems such as considerable lag time (up to several hours), unestablished correlation to blood/breath alcohol content, and thus unreliable detection performances. In contrast, the disclosed spiked microneedle sensor technology presents a successful demonstration of truly continuous, real-time alcohol monitoring with tremendous clinical and personalized utility.

The sensor response to varying multi-event activity/stimuli expected during daily activity is shown in FIG. 12B. Here, the sensor response reflects the differences in intensity between events for each sensor type. For instance, the lactate levels showed a peak intensity of only 5.8 mM with a shorter ~50 min return-to-baseline time corresponding to a one-minute low intensity exercise, but a 15 mM lactate peak with a longer ~160 min return-to-baseline time in the case of the 4 min high intensity exercise. Similarly, the glucose results reflect closely the meal consumed, FIG. 12B panel (g). In the case of the alcohol levels, the effect of varying the alcohol consumption rate on the subject was captured with a rapid alcohol consumption leading to a higher, sharper peak, whereas a slower one resulted in a lower, wider peak. AUC values were very similar (5.1 vs. 5.3 mM-h), reflecting the identical amounts of alcohol consumed for both events. The multi-event profiles obtained for the three target analytes (lactate, glucose, alcohol) with the example spiked microneedle sensors are in excellent agreement with the results of the corresponding reference method (i.e., blood, breathalyzer). Of considerable note is the subjects' indication of pain and discomfort associated with the validation experiments using conventional finger pricking blood meters, as each of single- and multi-event trials required over 30 capillary blood samplings.

Figure 13:
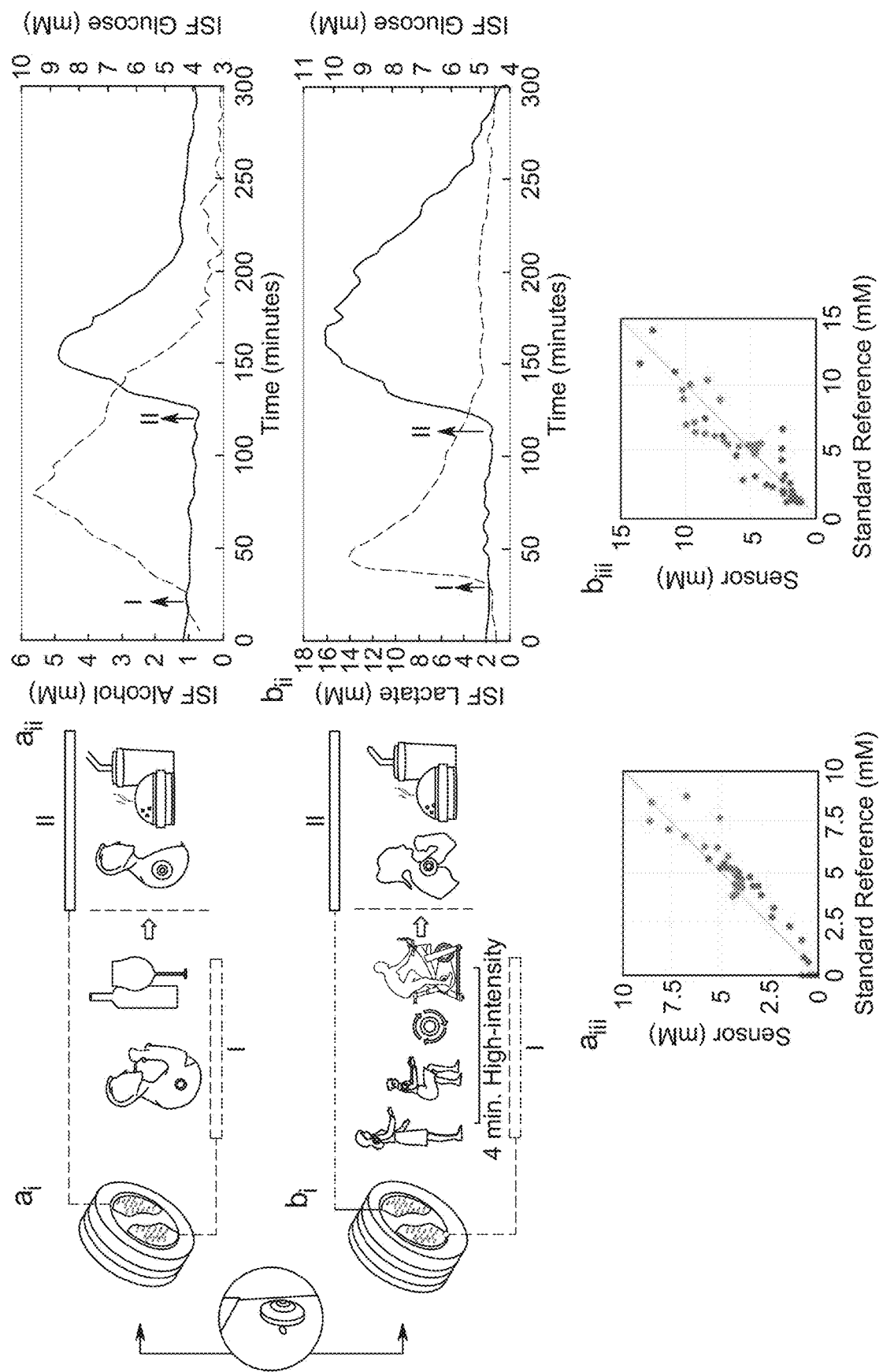
FIG. 13 show diagrams and data plots from example on-body performance implementations of an example spiked microneedle array biosensor device with multiple analyte sensors in accordance with the example embodiments shown in FIGS. 8-11.

FIG. 13 shows diagrams and data plots depicting an example in vivo performance implementation of an example spiked microneedle array biosensor device with multiple analyte sensors in accordance with the example embodiments shown in FIGS. 8-11. FIG. 13 panel (a) series shows diagrams and data plots of an example spiked microneedle sensor device placed on a subject's arm for a multi-analyte sensing study using an alcohol-glucose multiplexed spiked microneedle sensor during ($a_i$) a wine-consumption event followed by ($a_i$) a meal-consumption event with ($a_{ii}$) the corresponding plot of ISF alcohol and glucose measurements by the sensor vs. blood alcohol breathalyzer and blood glucose strip reference measurements; and FIG. 13 panel (b) series shows diagrams and data plots of an example spiked microneedle sensor device placed on a subject's arm for a multi-analyte sensing study using a lactate-glucose multiplexed spiked microneedle sensor during a 4-minute high-intensity workout followed by consumption of a full meal with ($b_{iii}$) the corresponding plot of ISF lactate and glucose measurements by the sensor vs. the blood lactate and glucose strip reference measurements.

The multiplexed monitoring ability of the spiked microneedle sensor is demonstrated for simultaneous alcohol-glucose and lactate-glucose sensing. Given the influence of alcohol consumption on glucose homeostasis, alcohol monitoring along with glucose can provide invaluable personalized information for individuals toward reducing their risk of developing type 2 diabetes. The ability of multiplexed alcohol-glucose monitoring in real-time can also help people with diabetes avoid delayed hypoglycemia which usually occurs following alcohol intake due to the reduced gluconeogenesis and depleting the glycogen stores. On the other hand, monitoring lactate along with glucose can offer a more comprehensive pro-diagnostic information regarding the risk of metabolic syndrome. Additionally, given different glycemic response of the people with diabetes to exercise, lactate monitoring can help more precise insulin delivery adjustment in these patients. Despite the high demands for such multiplexed monitoring of metabolites, to date there is no device capable of continuously and simultaneously measuring glucose-lactate in real-time.

FIG. 13 panel (a) illustrates the response of the alcohol-glucose sensing for alcohol consumption followed by consumption of a glucose-rich meal. The lag-free temporal biomarker profiles (panel ($a_{ii}$)) of the sensor corresponds to the breath- and blood-based validation measurements (taken in parallel) without any evidence of chemical or electronic crosstalk between the individual sensors. The chemical crosstalk, which can occur due to the migration of hydrogen peroxide between sensors of different analytes, is especially a major concern when designing an oxidase-based multi-sensor for in vivo applications. Molecular crosstalk was addressed through both a judicious design via spatially separating the dual sensing regions (e.g., 11 mm) and an optimized mitigated sensitivity achieved via utilizing a smaller number of working electrodes for each analyte. Accordingly, the Pearson's r for alcohol and glucose were found to be 0.98 and 0.86, respectively, highlighting the high accuracy of the multiplexed spiked microneedle monitoring of the two markers. Moreover, simultaneous monitoring of lactate and glucose resulted in successful tracking of each metabolite in response to their respective stimuli without any crosstalk between the two sensing systems, panel (b) (Pearson's r of 0.92 and 0.81 for lactate and glucose, respectively).

As discussed above, the example implementations have successfully demonstrated a fully integrated wearable microneedle platform for painless, continuous, real-time simultaneous measurements of multiple biomolecules from interstitial fluid in a tremendously low-cost manner. Measurement data was acquired through custom designed electronics, and wirelessly transmitted to an accompanying smartphone app for capture and visualization. By relying on the ISF as a rich source of biochemical information, the wearable microneedle platform collects, in real-time, rich molecular data continuously during diverse daily activities that currently can be obtained only as a single measurement by centralized laboratory tests. The performance of the wearable microneedle platform was thus demonstrated by monitoring fluctuating ISF levels of key biochemical markers lactate, alcohol, and glucose—in single and multiplexed configurations—in response to stimuli associated with common daily routines, namely exercise, food consumption, and alcohol consumption. Example implementations were performed on human subjects, where each human subject was validated by parallel measurements using standard reference methods. The disclosed wearable microneedle platform addresses the fundamental practicality issues of epidermal sweat measuring wearables, as well as the invasiveness and limited single-analyte capability of CGMs, thereby enabling pain-free, non-intrusive, multiplexed monitoring of biomarkers from the body. Furthermore, the platform can readily be reconfigured for detection of additional biomarkers, facilitating the continuous collection of clinically relevant data not previously accessible and therefore potentially providing a more comprehensive view into the body's physiology. By filling the current gaps between research and commercialization, the example embodiments of the wearable microneedle platform presents a significant leap forward in the field and can accelerate the emergence of next generation, patient-centered remote monitoring wearable sensors, thereby offering a pathway to transform the current state of digital healthcare.

Example Methods of Manufacture and Implementation of the Disclosed Fully Integrated Wearable Microneedle Platform Example Materials Used.

Glucose oxidase (GOx, EC 1.1.3.4, from *Aspergillus niger*), D-(+)-glucose anhydrous, alcohol oxidase (AOx, from *Pichia pastoris*, 10-40 units/mg), chitosan (medium molecular weight), bovine serum albumin (BSA), γ-globulins from bovine blood, L-lactic acid, ascorbic acid (AA), calcium chloride anhydrous ($CaCl_2$)), glacial acetic acid (HOAc), poly(ethylene glycol) diglycidyl ether (PEGDE), hydrochloric acid (HCl), polyvinyl chloride (PVC), Triton X-100, o-phenylene diamine (oPD), acetaminophen, and uric acid (UA), sodium sulphate ($Na_2SO_4$), iron (III) chloride ($FeCl_3$), magnesium sulfate anhydrous ($MgSO_4$), phosphate buffer solution (PBS) (1.0 M, pH 7.4), potassium chloride (KCl), sodium dihydrogen phosphate ($NaH_2PO_4$), sodium bicarbonate ($NaHCO_3$), sodium chloride (NaCl), sodium gluconate, and sucrose were obtained from Sigma-Aldrich. Lactate oxidase (LOx, EC 1.1.3.2, 106 U/mg) was obtained from Toyobo, USA. Ethanol was obtained from Decon Laboratories (Austin, USA). Tetrahydrofuran (THF) was provided by Millipore (Massachusetts, USA). Biocompatible BioMed photocurable resins were obtained from Formlabs (Berlin, Germany). For example, 3.2 mm thick poly (methyl methacrylate) (PMMA) sheets were obtained from McMaster-Carr (Chicago, USA). 3M™ Medical Tape was obtained from Tekra (New Berlin, USA).

Design and Fabrication of Example Disposable MN Component.

The spiked microneedle array with the capillary channels on the base for sealing, the microneedle covers, enclosure and holder components were designed using Fusion 360 software. 3D printing (Formlabs 3) was used to fabricate the cover ring; and a reproducibly high resolution (e.g., less than 100 μm resolution) micromachining process was used to fabricate the spiked microneedle array with the sealing microfluidic channels on the base of the spiked microneedle array (e.g., see FIG. 19) in a scalable and cost-effective manner. It is noted that ultra-high-resolution 3D printing can be used to fabricate, via computer-based design, the spiked microneedle array substrate and cover component, which can provide ultra-high resolution of structures with resolution of 5 μm or less (e.g., a hundred or hundreds of nanometers to 5 μm resolution range). The cover component and spiked microneedle array were then assembled with the photocurable resin being introduced to the interface followed by spontaneously forming a sealant layer at the interface and around the spiked microneedles up to the spiked microneedles reproducibility cutoff line. Briefly, for the single analyte sensors (e.g., lactate, glucose, alcohol), a 3-electrode electrochemical system was used with the electrodes ratio of 16WE/8CE/IRE (e.g., see FIGS. 19-20). The multiplexed sensors (e.g., lactate-glucose, alcohol-glucose), relied on two 3-electrode systems, with two physically isolated working electrodes, two complementary counter electrodes, and two complementary reference electrodes, in the ratio of 6WE/8CE/IRE (e.g., see FIG. 10, panel ($b_{iii}$))

Preparation of Example Biosensors.

A o-PD (5 mM) solution was prepared in an acetate buffer (I=0.2 M, pH 5.2) and electrodeposited at 0.65 V (vs. Ag/AgCl) for 15 min. The enzyme solutions GOx (20 mg/mL), LOx (12 mg/mL), and AOx (10 mg/mL) were prepared in chitosan (1 wt % in 1% HOAc) in optimized volume ratios of 1:2, 1:10, and 1:1, respectively. For example, 2 mL of each enzyme solution was used to modify the corresponding biosensor by covering the microneedle array, followed by crosslinking with 1 mL of PEGDE (1%). The electrodes were then modified by casting chitosan solution (e.g., 1 mL, 2 mL, and 1 mL for glucose, lactate, and alcohol biosensors, respectively). Finally, a 2% PVC solution prepared in THF solvent and containing 1 mM Triton X-100 was cast onto the microneedle (e.g., 1 mL for the glucose and lactate biosensors, and 1.5 mL for the alcohol biosensor) and chilled for 4 h at 4° C. for further experimentation.

Sterilization and Cytotoxicity Test.

Cytotoxicity of the spiked microneedle array was tested through Live/Dead staining of J774 cells in DMEM media (Thermo Fisher, Waltham, USA), by immersing the disposable piece of the example spiked microneedle sensor patch in advance. For example, J774 macrophage cells (e.g., 2×105/mL) were seeded to a 6-well plate and cultured for 24 h at 37° C. The sample was prepared by immersing the example spiked microneedle sensor patch that is sterilized by UVc and autoclave for 24 h. The cell-containing wells were washed with PBS, then treated with a Live/Dead staining kit (BioLegend, San Diego, USA). Fluorescence images were taken by an inverted fluorescent microscope and analyzed using ImageJ to determine the percentage of live and dead cells in each sample (N=5) (e.g., see FIG. 22). Further UVc sterilization was performed on each enzyme immobilized sensor (30 minutes, Level II) prior to application onto the body (e.g., see FIG. 22).

Example Fabrication and Assembly Techniques for the Example Electronic System.

The example components of the electronic system used in the example implementations (e.g., discussed in connection with FIGS. 8-13) were assembled onto a 4-layer FR4 printed circuit board (PCB), e.g., which measures 0.5 mm in height and 5.3 $cm^2$ in area (r=13 mm). Fabrication and assembly were performed by PCBminions (Princeton, NJ, USA & Shenzhen, China). Components were sourced from Digi-Key Electronics (Thief River Falls, MN, USA). Example components include the AD5940 electrochemical analog front end (AD5940BCBZ-RL, Analog Devices, Inc., Wilmington, MA, USA), the CYW20736S Bluetooth Low Energy (BLE) system-in-package (SiP) module (CYW20736S, Cypress Semiconductor Corporation, San Jose, CA, USA), a 2.8V low-noise, low quiescent current low-dropout (LDO) regulator (LP5907UVX-2.8/NOPB, Texas Instruments, Dallas, TX, USA), a wireless Li-ion battery charger (LTC4124EV #TRMPBF, Analog Devices, Inc., Wilmington, MA, USA), a wireless charging coil (WR202020-18M8-G, TDK, Chuo City, Tokyo, Japan), and a 110 mAh Li-ion coin cell battery (RJD2430C1ST1, Illinois Capacitor, Des Plaines, IL, USA). The electrode connection includes five gold plated nickel, 0.508 mm diameter pins (0508-0-00-15-00-00-03-0, Mill-Max Manufacturing Corporation, Oyster Bay, NY, USA).

Electrochemical Sensing Operation.

The AD5940 electrochemical analog front end (AFE) integrates multiple circuits for performing electrochemical analysis, which are functionally grouped into circuitry for multiplexed input selection, potentiostat operation, signal conditioning and digital conversion, and data communication. The AFE interfaces with the sensor array through the five gold-plated pins. Four of the pins are used as multiplexed input channels when operating in a 2-electrode configuration (labeled WE1, WE2, WE3, and WE4), with the fifth pin used for a combined counter/reference electrode. When operating in a 3-electrode configuration, three working electrodes are available for multiplexing (WE1, WE2, WE3), and the fourth and fifth pins are used for the counter and reference electrodes. Each working electrode input can be individually addressed to connect the electrode to the potentiostat circuit for electrochemical analysis.

The potentiostat circuit includes a control amplifier (CA), a transimpedance amplifier (TIA), and a 12-bit dual output digital-to-analog converter (DAC) which sets the common mode reference electrode potential ($V_{RE}$) and working electrode potential ($V_{WE}$). The TIA converts input current $I_{In}$ into a voltage to be measured by the ADC. The potential difference ($V_{WE}$-$V_{RE}$), set by the DAC, is applied to a connected electrochemical cell through the control amplifier and TIA. The operational range for the applied potential is +/−1.0V with a resolution of 0.537 mV (12-bit DAC, $V_{Ref}$=2.2V).

Signals from the TIA feed into the signal conditioning and digital conversion circuitry, which include a programmable analog RC filter, a differential multiplexer (labeled ADC MUX), a programmable gain amplifier (PGA), a 16-bit analog-to-digital converter (ADC) for digitizing signals into measurement data, and cascaded digital $sinc^3$ and $sinc^2$ filters. Both the TIA and PGA feature programmable gain values. The ADC was configured to measure the differential voltage between the amplifier output and $V_{WE}$ via the ADC MUX.

The AFE also contains data registers to store configuration information and for storing measurement data from the ADC or digital filters. Data communication with these data registers occurred through the AFE's SPI interface.

Signal filtering on the AFE, which is used to suppress random electronic noise and electrochemical noise, is accomplished in both the analog and digital domains. A single pole low pass analog filter is formed by a programmable resistor and a 1 µF capacitor located at the output of the TIA/BUF amplifier. The resistor is set to 20 kΩ, resulting in a 3 dB cutoff frequency of 7.96 Hz, which was chosen suppress noise whilst not allowing the filter's settling time to cause measurement inaccuracies for the capacitive currents found in amperometry tests. The ADC output connects to a digital $sinc^3$ filter followed by a $sinc^2$ filter. Configuring the bandwidths of these filters is done by digitally setting their oversampling ratios, which are set to 5 and 1333 for $sinc^3$ and $sinc^2$, respectively (the maximum setting on the AFE). This produces an overall filter 3 dB bandwidth of 38.32 Hz at a sampling rate of 800 kSPS (found through simulation). Note that the frequency response of digital sinc filters is similar to that of averaging/integration methods commonly used in electrochemical analysis. An additional 60 Hz/50 Hz mains filter is used after the sinc filters.

Signal amplification is performed by the TIA and PGA to ensure that their levels are always within the detectable limits of the ADC over a wide range of input current. An autoranging system is employed to dynamically adjust the TIA and PGA gains during tests to do so. The system algorithm recursively tests different transimpedance values until the signal level is within 20% to 80% of the ADC's full range. Each gain level covers 12.04 dB of range, except for the highest transimpedance level which covers 73.1 dB from 16.2 nA down to 3.6 pA (e.g., the limit of detection for the electronic system), and the lowest transimpedance gain level which extends from 0.83 mA up to 2.15 mA for a range of 8.3 dB. The autoranging system allows the electronic system to support a range of 2.15 mA to 3.6 pA (175 dB of range). Note that a diode pair is connected to the TIA's feedback path to not disturb the cell biasing (allowing current to flow) while switching between $R_{TIA}$ values.

BLE Operation.

The CYW20736S BLE SiP module features an ARM Cortex-M3 microcontroller (MCU), a BLE radio, and an embedded planar inverted-F antenna. The module is programmed to control all electronic system functionality, namely configuration of the AFE through its SPI bus, control of electrochemical measurement data acquisition, and wireless communication with a mobile device over BLE.

Wireless BLE operation of the electronic system is described, as an example. The electronic system in the some of the example implementations was configured as a Bluetooth Generic Attribute Profile (GATT) server and hosts custom services and characteristics which a GATT client—the smartphone—can interact with. The BLE GATT can be organized into "services" which group together pieces of data referred to as "characteristics." Two services were used for electrochemical tests: a configuration service and a measurement data service. The configuration service contains characteristics for setting test parameters (e.g., applied potential for amperometry). The measurement data services can act as unique data channels for transmitting data, and trivially contains a characteristic for measurement data. Prior to transmission, measurement data acquired through the ADC is converted to relevant measurement units—current in pA for amperometry.

Power Management and Wireless Recharging.

The power management and wireless recharging circuitry on the electronic system include a wireless recharger IC, a 2.8V LDO, and a wireless charging receive coil. For example, power for the electronics was sourced from the rechargeable Li-ion battery—a 2430 type (e.g., 24 mm in diameter, 3.0 mm in height) coin cell. The example battery, receive coil, and PCB were adhered to each other with double-sided tape, resulting in a total device height (e.g., from the top of the battery connector to the bottom of charging coil) of 6 mm and a diameter of 26 mm.

Under normal operation, power is sourced from battery, through the wireless recharger IC, and into the LDO. The LDO then regulates the battery voltage (~3.7V) down to 2.8V, which is supplied to the AD5940 and CYW20736S. The electronic systems begin inductively charging the battery when it is placed on a transmitter pad. Charging is regulated by the wireless recharging IC, which features over-discharge protection and constant current/constant voltage charging capability to quickly charge the battery without overcharging.

Power Optimizations.

Both the AD5940 AFE and CYW20736S BLE module feature "sleep" modes to reduce average power consumption by power-gating and/or clock-gating circuit blocks. This is leveraged on the AFE by turning the ADC and digital filters on solely for periodic sampling events and turning them off outside of these events. Furthermore, the microcontroller and BLE radio on the CYW20736S are deterministically gated between sampling events. Note that throughout an entire electrochemical test, the DAC, control amplifier, and TIA/BUF amplifier are left on to maintain the reference electrode potential and maintain/measure the working electrode potential for potential-controlled/potentiometry tests.

In the example implementations, the instantaneous current consumption before, during, and after a single sampling event included the following. An increase in current to ~10 mA was observed at t=0.4 s, indicating that the microcontroller, ADC, and digital filters have been turned on to begin a sampling event. The current drops down shortly after, indicating that data had been sampled and the microcontroller, ADC, and digital filters have turned off. Next, the current spikes to ~20-30 mA, indicating that the BLE radio and microcontroller have turned on, which occurs for 3 sequential BLE connection events. During the first, data was transmitted to a mobile device. Next, the electronic system received a confirmation from the mobile device that the measurement data had been properly received. Lastly, the electronic system received an empty BLE packet from the mobile device, telling the electronic system that no further BLE communication will take place, allowing the BLE radio to be kept off until the next sampling event. Before and after these events, the low current levels labeled "Sleep" verify that ICs were successfully placed into low power modes. Small spikes of ~5 mA appear every 100 ms—this is the CYW20736S periodically waking up to briefly to perform basic system operations, such as flashing the electronic system's LED, taking battery level measurements, or checking if data needs to be retransmitted due to a BLE disconnect.

The average current consumption of a 60 s amperometry test (sampling interval=1 s) and the instantaneous current of three sampling events during this test for reference was considered. The average current lied close to the "Sleep" current found between sampling events, as the electronic system remains primarily in sleep mode given the long sampling interval.

Current consumption decays back to 1.06 mA as the sampling interval was increased back to 1 s, resulting in a battery life of 4 days and 7.6 hours. Additionally, the electronic system can be placed into an ultra-low power mode via a BLE command whereby all components are turned off for a preset duration of time. In this mode, the electronic system consumes 53.5 µA. Duty cycling this ultra-low power mode with continuous sampling allows for significant battery life gains. For instance, 10% duty cycling with 1 minute of continuous sampling mode (e.g., sampling interval=1 s) followed by 9 minutes of ultra-low power mode results in average current consumption of 154 µA and a battery life of approximately 30 days.

Firmware Programming.

Programming and reprogramming procedure for the electronic system used in at least some of the example implementations are described. The programming used UART connections (Tx, Rx, VCC, GND), and required a physical connection between the electronics and a personal computer which hosts the firmware. This was accomplished by first connecting the electronics to a Cypress BCM92073X_LE_KIT development kit through a 6-pin Molex PicoBlade cable, and connecting the kit to the personal computer using a micro-USB cable. The development kit was needed specifically for its on-board FTDI USB-UART interface chip, which converts serial UART signals into serial USB signals. Initial programming the electronics is accomplished using Cypress' WICED SMART, a software development kit (SDK) which provides an Eclipse-based integrated development environment (IDE) for building firmware and downloading it to the electronics. Thereafter, the programming header of the electronics (which has no active components) is cut off, making the electronic system ready to be integrated with the sensor array.

Reprogramming can be done through over-the-air (OTA) updates via BLE. Afterward, programming is done wirelessly via BLE through Over-the-Air (OTA) updates. This enables rapid deployment of firmware updates in line with today's agile software development environments.

In Vitro Characterization of the Example Sensors.

In vitro characterizations were performed in an artificial ISF solution to evaluate and optimize the performance of each biosensor. The artificial ISF solution was prepared. Calibration experiments for each biomarker were performed, covering the physiological ranges of each analyte. The amperometric responses obtained at applied potential of 0.6 V (e.g., see FIG. 23B panels ($a_{ii}$), ($b_{ii}$), and ($c_{ii}$) for lactate, alcohol, and glucose, respectively), and the corresponding calibration plots (e.g., see FIG. 23B panels ($a_{iii}$), ($b_{iii}$), and ($c_{iii}$)) reveal the excellent linearity of the biosensors. The stability of biosensors was examined by attaching a modified microneedle device to a custom-designed electrochemical chamber with full sealing of the containing solution (e.g., 1 mL volume), spiking with specific target analyte concentrations (e.g., 10 mM lactate, 15 mM alcohol, and 10 mM glucose), and recording amperometric responses at 10 min intervals for 12 h. As illustrated in FIG. 23B panels ($a_{iv}$), ($b_{iv}$), and ($c_{iv}$), the biosensors exhibited remarkable stability over a prolonged duration of time. The selectivity of the biosensors was verified by adding concentrations of the target analyte into artificial ISF containing common interfering species (e.g., ascorbic acid, uric acid, acetaminophen, tryptophane, methionine and histidine) (e.g., see FIG. 23B panels ($a_{vi}$), ($b_{vi}$), and ($c_{vi}$)).

On-Body Characterization of the Sensors.

Fully sterilized sensor patches were placed on the left or right arm of each subject using double-sided medical tape and an extra tape to cover the microneedle patch on the skin. Testing commenced immediately, achieving <6 initial data points (e.g., <30 minutes) to form a stable baseline followed by the initiation of the activity (e.g., exercise, food, or alcohol consumption) while sensor operating in the background. Protocol for each activity is as follows.

Lactate Continuous Sensing:

In the unchanging single-event experiments (FIG. 12A), each participant went through a 4-minutes high-intensity exercise starting with a 1-minute body-squat (e.g., 30 repetitions), immediately followed by a 1-minute interval biking (e.g., a 30-second of slow low-intensity at 50 RPM with resistance of 3/10 that rapidly turns into a 30-seconds of a faster high-intensity at 50 RPM with resistance of 8/10), followed by 45 s of resting all of which were repeated for two times. For the varying multi-event lactate experiment (FIG. 12B), the participant first went through a 1-minute, moderate-intensity biking (i.e., at 50 RPM and a 6/10 resistance), and then four minutes of a high-intensity exercise session described above. A similar 4-minute high-intensity exercise was performed for the multiplexed lactate-glucose sensing experiment (FIG. 13).

Glucose Continuous Sensing:

For the unchanging single event (FIG. 12A), each participant consumed a double quarter pound burger with a 20 oz bottle of cola soda pop. In the varying multi-event glucose experiment (FIG. 12B), the participant, first consumed the same burger and cola combination, and then consumes one piece of a cheesecake (e.g., 120 g) and a large apple (e.g., 200 g). For both of the multiplexed sensing experiments, both participants consumed the same burger and cola combination.

Alcohol Continuous Sensing:

One glass of wine (e.g., 150 mL of 14.5% alcohol content) was consumed in every alcohol monitoring experiment (FIGS. 12A-13). In the unchanging single event experiments, the alcohol was consumed in a rapid one-single shot (e.g., <5 seconds), and in the varying multi-event experiment, the same one-glass of wine was consumed in three occasions with 15 minutes of interval in between (FIG.

12B). Amperometric experiments carried out for 60 s at 5 minutes intervals were exploited for all experiments with the last data point being calibrated versus the gold-standard metrics using two-point calibration method.

The lactate, alcohol and glucose data were validated in 10 min intervals by commercial blood lactate meter (NOVA Biomedical), breathalyzer (BACtrack S80 Pro), and blood glucose meter (ACCU-CHEK), respectively. In case of alcohol monitoring tests and according to the instructions from the manufacturer, subjects were asked to wait 15 min before recording their breath alcohol content by breathalyzer.

Figure 14:
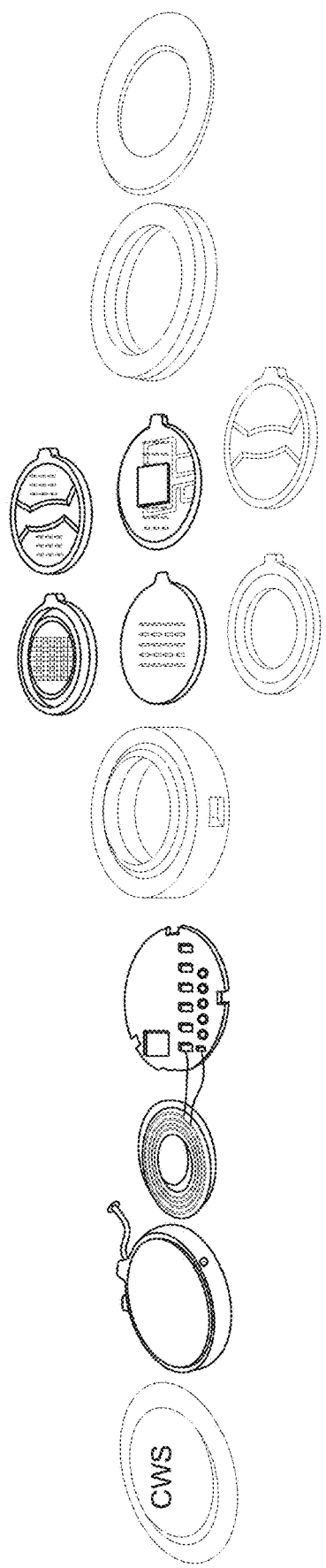
FIG. 14 shows an image of an example embodiment of the fully-integrated, non-intrusive, wirelessly-operated, wearable microneedle sensor platform shown in FIG. 8 disassembled.

FIG. 14 shows an image of an example embodiment of the fully-integrated, non-intrusive, wirelessly-operated, wearable microneedle sensor platform shown in FIG. 8 disassembled. For example, the disassembled components of the sensor are shown (from left to right) to include the patch enclosure cap, battery, recharge coil, PCB, holder B, spiked microneedle single analyte 5-by-5 sensor array, multiple analyte sensor array (with corresponding cover ring of each on the below and the assembled piece on the top of each sensor array), holder A, and a double sided disposable medical tape.

Figure 15:
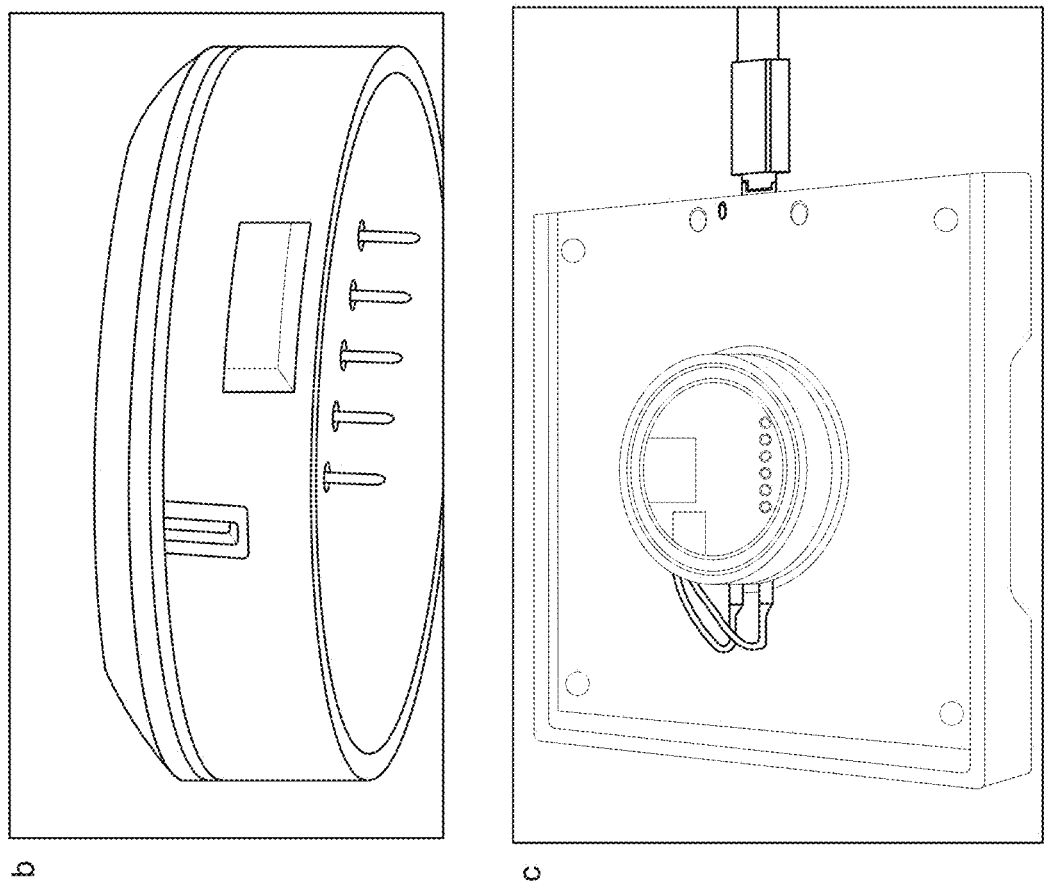
FIG. 15 shows images of wireless recharging hardware for an example electronics sub-system used in example implementations of a wearable microneedle sensor platform in accordance with the present technology.
Figure 15:
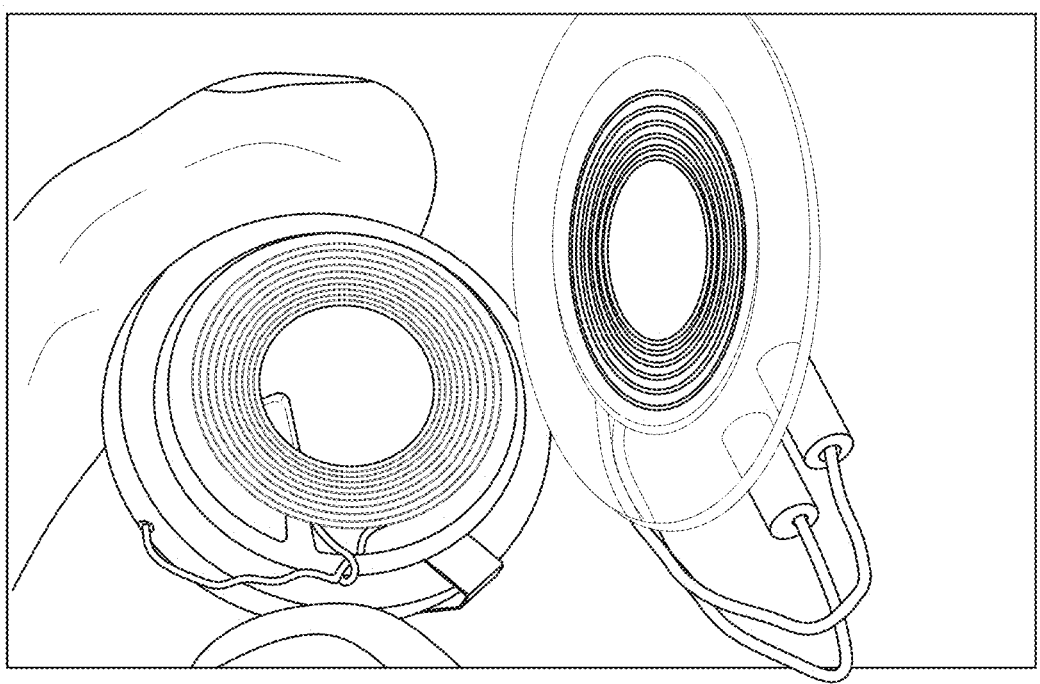

FIG. 15 shows images of example wireless recharging hardware for an example electronics sub-system. Image (a) shows inductively coupled coils on an electronics and transmitter pad (DC2771A-B WPT, Analog Devices, Inc., Wilmington, MA, USA) with coils to support wireless power transfer. Image (b) shows plastic housing on the electronics, providing an air gap between the coils when charging without degrading charging performance. Image (c) shows electronics placed on transmitter pad, receiving power via the connected micro-USB cable.

Figure 16:
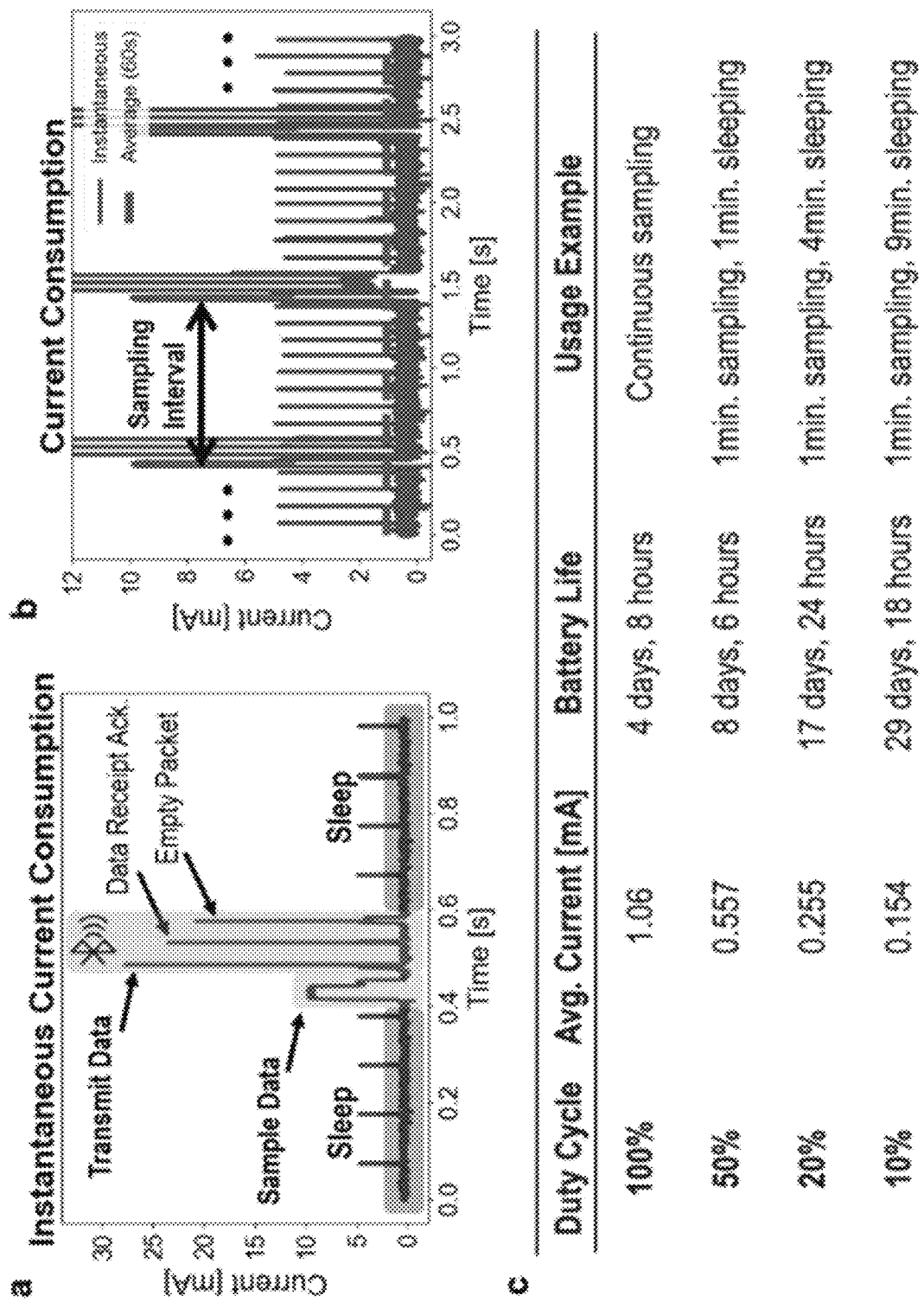
FIG. 16 shows example data of a power optimization implementation for an example embodiment of an electronics unit of a wearable microneedle sensor platform in accordance with the present technology.

FIG. 16 shows data plots of an example power optimization implementation for an example embodiment of the electronics unit. Data plot (a) of FIG. 16 shows the instantaneous current consumption for 1 sampling event. Data plot (b) of FIG. 16 shows the instantaneous and average current consumption (=1.06 mA) for a 60 s test (e.g., sampling interval of 1 s) zoomed into the first 3 sampling events. Table (c) of FIG. 16 provides data for utilization of an ultra-low power mode (e.g., current consumption=53.5 µA) to reduce average current consumption via duty cycling.

Figure 17:
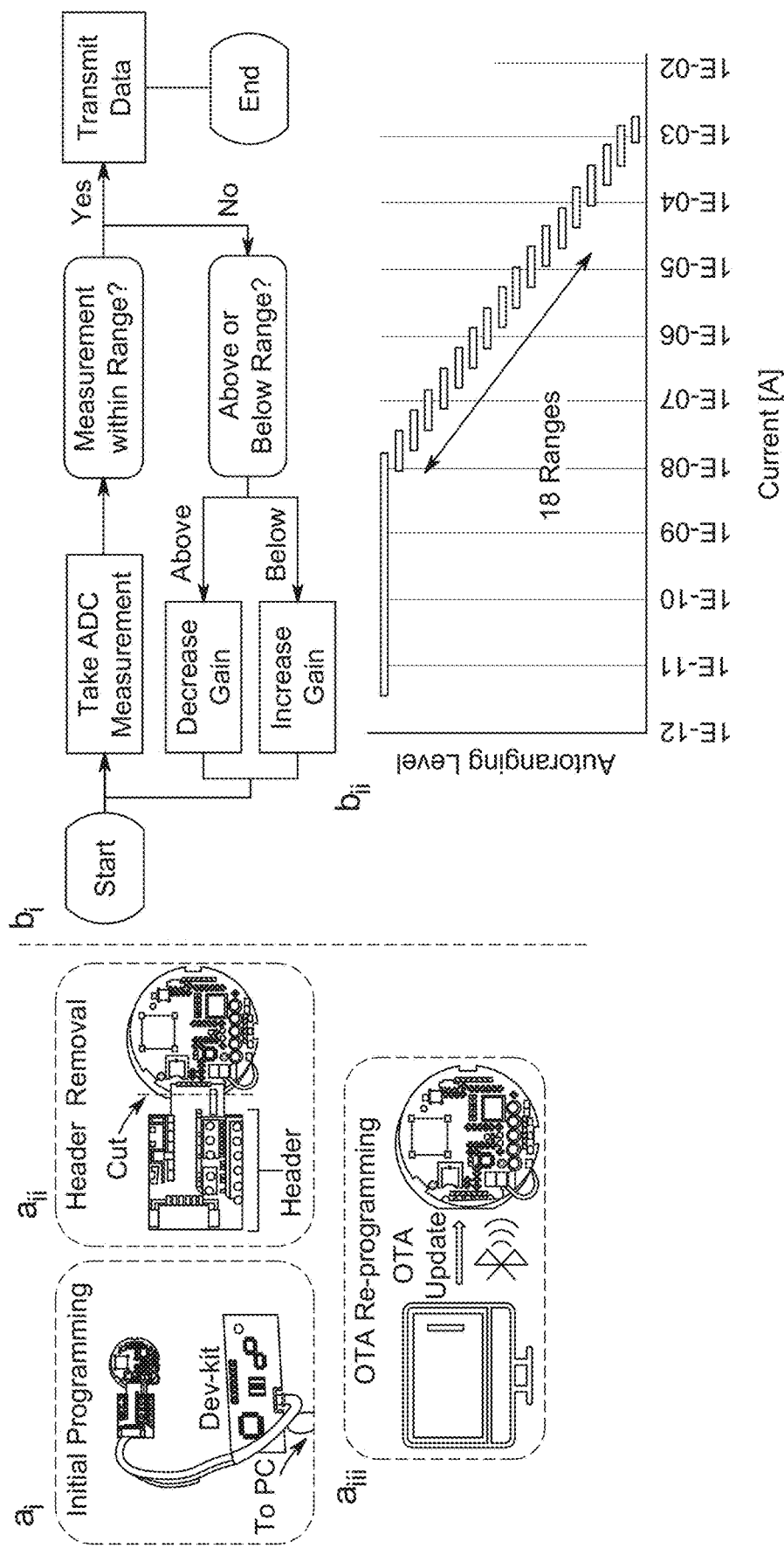
FIG. 17 shows diagrams and data plots associated with software features for example embodiments of a wearable microneedle sensor platform in accordance with the present technology.
Figure 17:
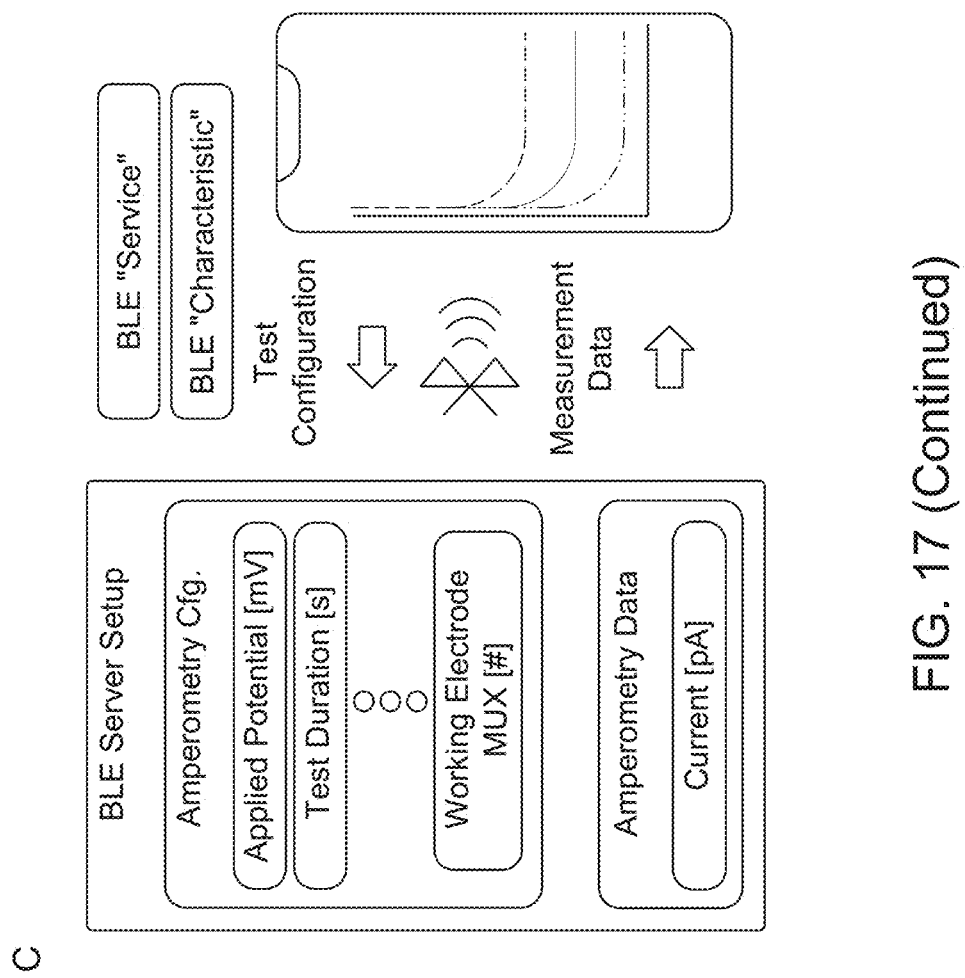

FIG. 17 shows diagrams and data plots associated with software features for example embodiments of a wearable microneedle sensor platform in accordance with the present technology. FIG. 17 panel ($a_i$) shows a diagram depicting programming and reprogramming steps of an electronics unit, e.g., including initial programming from an external computing device hosting the firmware, removal of the programming header, and OTA reprogramming through wireless BLE communication. FIG. 17 panel (b) depicts an auto-ranging system used for dynamic gain adjustment, where diagram ($b_i$) shows a flowchart of auto-ranging algorithm (method) in accordance with the present technology, and data plot ($b_{ii}$) shows current ranges corresponding to each of the example 18 levels available to the auto-ranging system. FIG. 17 panel (c) shows a diagram illustrating an example BLE operation for the electronics, in which the BLE GATT server contains BLE services for configuring electrochemical tests and for test measurement data, allowing a mobile device to act as a proxy for easy control of the electronics.

Figure 18:
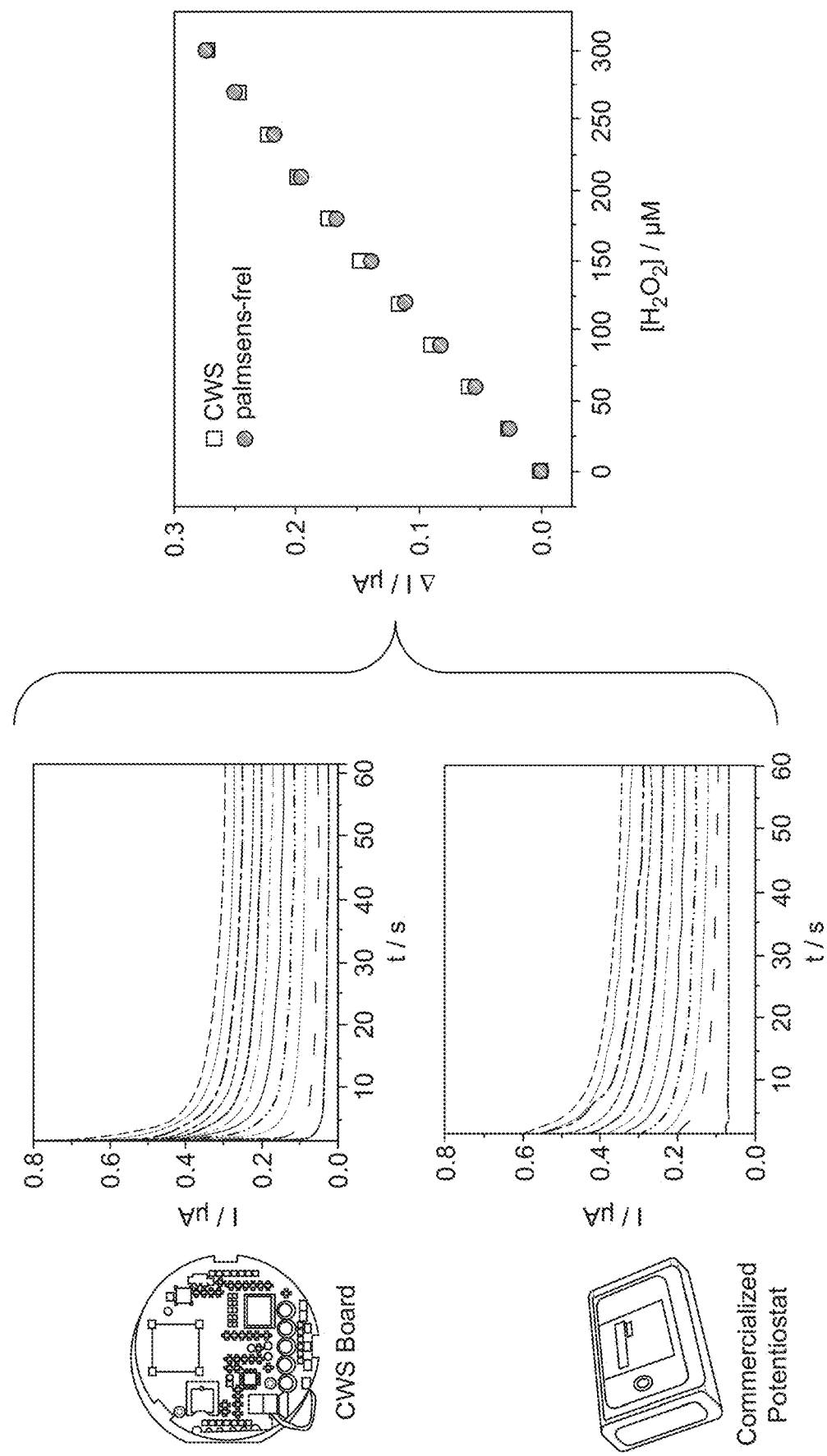
FIG. 18 shows diagrams and data plots associated with a comparative study between a CWS board electronic system and a conventional potentiostat.

FIG. 18 shows diagrams and data plots associated with a comparative study between a CWS board for an example embodiment of the electronic unit 120 (upper left) and a conventional potentiostat (lower left), including their amperometric response to standard additions of 30 µM hydrogen peroxide in a PBS solution with their overlaid calibration curves (where the applied potential was 600 mV).

FIG. 19 shows an illustrated flow diagram of an example embodiment of a fabrication method 1900 for a spiked microneedle sensor array in accordance with the present technology. The method 1900 includes a process 1910 to micro-machine an array of spiked microneedles and capillary microfluidic channels on and/or into a substrate surface (as shown in panels ($a_i$), ($a_{ii}$), and ($a_{iii}$)). For example, implementation of the process 1910 to micro-machine the capillary microfluidic channels into the substrate can (i) create a channel structure to facilitate sealing of the spiked microneedle structures on the substrate and (ii) create and define dielectric and/or insulated regions (e.g., onto bare metal surfaces) on the spiked microneedle structures, e.g., in subsequent processes of some embodiments of the method 1900. For example, a cut-off line can be designed for the microneedle structures to stop the flow up of the dielectric and/or insulated material (e.g., polymer resin) to the predefined height along the body region of the microneedle structure defined at the cut-off line, thereby ensuring a surface area of the sensing area (e.g., exposed electrically conductive material on the upper body region) will be reproducible and uniform among the spiked microneedle structures.

In some implementations of the process 1910, for example, the substrate (e.g., rectangular PMMA block) [panel ($a_i$)] is engraved to an intermediate state [panel ($a_{ii}$)] and final state [panel ($a_{iii}$)]. For example, such an intermediate state can include spiked microneedle structures with a cone shape, which can be achieved by engraving using a V groove CNC micro-bit with the desired tip angle ranging from 10°-85°, and by using a 2D contour CNC strategy that includes employing (I) a spindle speed of 3-6 krpm, (II) a surface speed of 100-157 m/min, and (III) a cutting feed rate of 700-1000 mm/min. Moreover, for example, pore structures can be created by the tip of the V groove CNC micro-bit on the surface of the cone feature using the above example machining parameters. Furthermore, for example embodiments of the microneedle structures that include the winding protrusion structures, a spiral body of the spiked microneedle can be formed by using a two-flute micro-CNC microbit followed by an inverted T micro-bits to form the spiral structure of the spike body, e.g., at the abovementioned example machining parameters. Also, for example, the micro-machining technique in the process 1910 can include using drilling bits for the formation of the microfluidic channels within the lower body alongside the external circumference of the spike structure, e.g., where these machined channels are to be responsible for carrying a curable resin polymer up to a cut-off region, e.g., reproducibility line, during a subsequent insulation process of the method 1900. In some embodiments of the method 1900, the process 1910 includes the processes among the micromachining method 3310 discussed later in connection with FIG. 33A.

The method 1900 includes a process 1920 to carry out thin-film depositions and etching to create an array of spiked microneedles. In some implementations of the process 1920, for example, the process 1920 includes (i) thin film-depositing a first material (e.g., PMMA) to form a batch of a clean spiked microneedles (e.g., PMMA array of spiked microneedles) as shown in panel ($b_i$); (ii) then thin filmdepositing a second material to the batch of clean spiked microneedles to form a first coating on the spiked microneedles, e.g., such as by sputtering Cr/Pt/Ag to form a Cr/Pt/Ag-coated array of spiked microneedles as shown in panel ($b_{ii}$); and (iii) followed by etching of a conductive material (e.g., Ag) from the spiked microneedles to be designated as the working and counter microneedle microelectrodes and subsequent reference-electrode prepping, e.g., such as chloritization of the conductive material (e.g., chloritization of Ag to Ag—AgCl as the reference microelectrodes) as shown in panel ($b_{iii}$).

The method 1900 includes a process 1930 to electrically isolate one or more working microelectrode regions (e.g., one or more sets of WE microneedles), at least one counter microelectrode region (e.g., one or more sets of CE microneedles), and at least one reference microelectrode region (e.g., one or more sets of RE microneedles), as shown in panel (bis). In some implementations of the process 1930, formation of the electrically isolated microelectrode regions can be achieved by removal of a thin film metal using mechanical abrasion (e.g., manual or using a CNC) on the traces; and/or removal of the thin film metal using laser machine. Implementations of the process 1930 can complete fabrication of a spiked microneedle array.

In some embodiments, for example, the method 1900 includes a process 1940 to assemble a cover (e.g., ring cover) over the fabricated spiked microneedle array, which can be followed by defining and sealing the spiked microneedle electrode structures. For example, in some implementations of the process 1940, the process 1940 includes forming a bond and sealing the cover and microneedle array, where the sealing process defines the sensing area. In such implementations, for example, the cover piece can first be immersed in a bath containing a thin layer of a photocurable resin; the cover can then be pressed against the microneedle array followed by UV curing to form a bonding between the two components. Also, in such implementations, for example, for sealing the bonded piece, the photocurable resin can first be introduced to microfluidic channels surrounding the interface between the cover piece and the microneedle array piece, which causes a spontaneous capillary-driven flow of the photocurable resin through the microfluidic channels towards the body of the microneedles up to the cut-off line; and the resin can subsequently be cured to create the sealed structure at the base of the microneedles.

Figure 20:
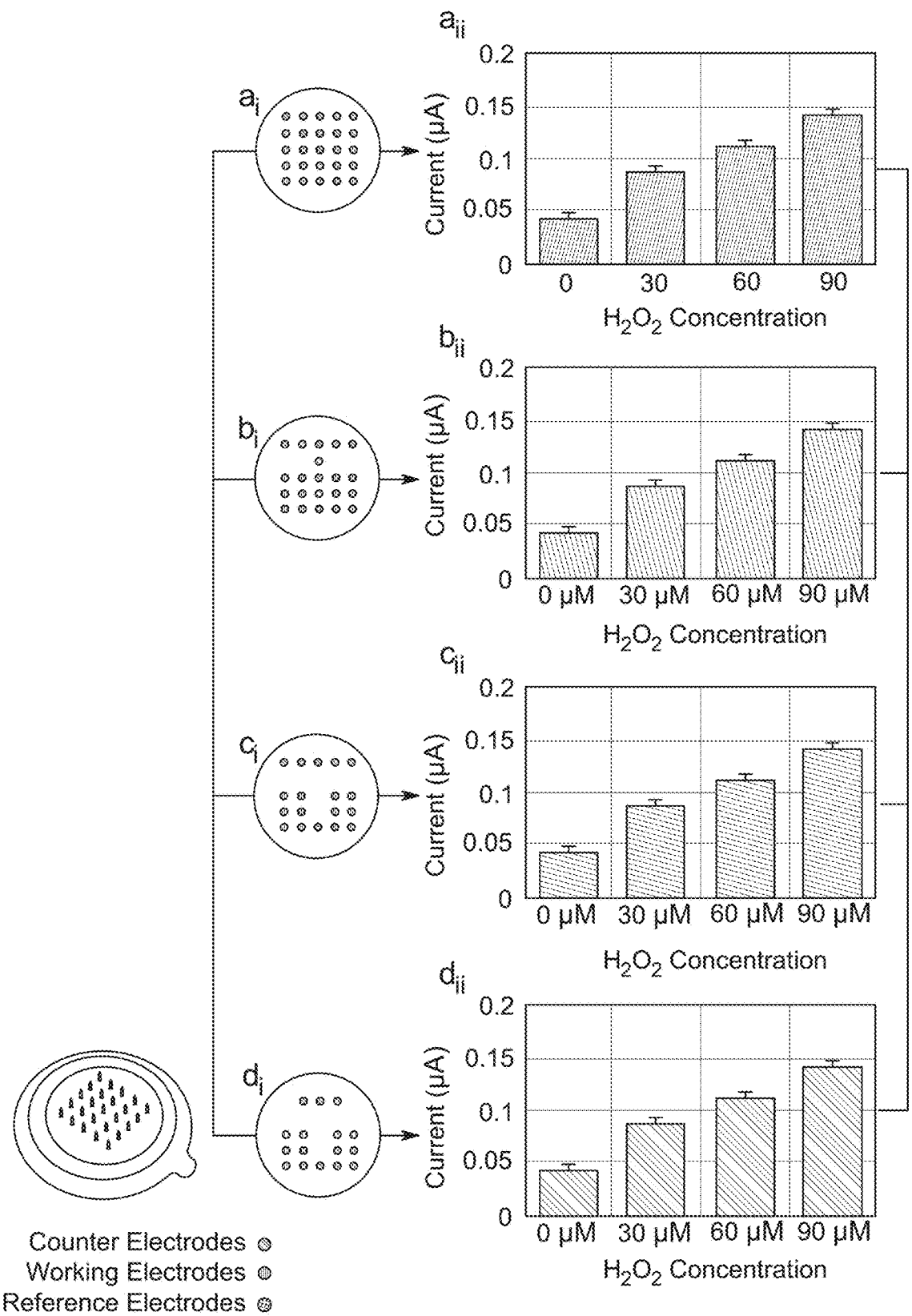
FIG. 20 shows a diagram presenting diagrams and example data associated with a WE/CE/RE ratio study for example implementations of a wearable microneedle sensor platform in accordance with the present technology.
Figure 20:
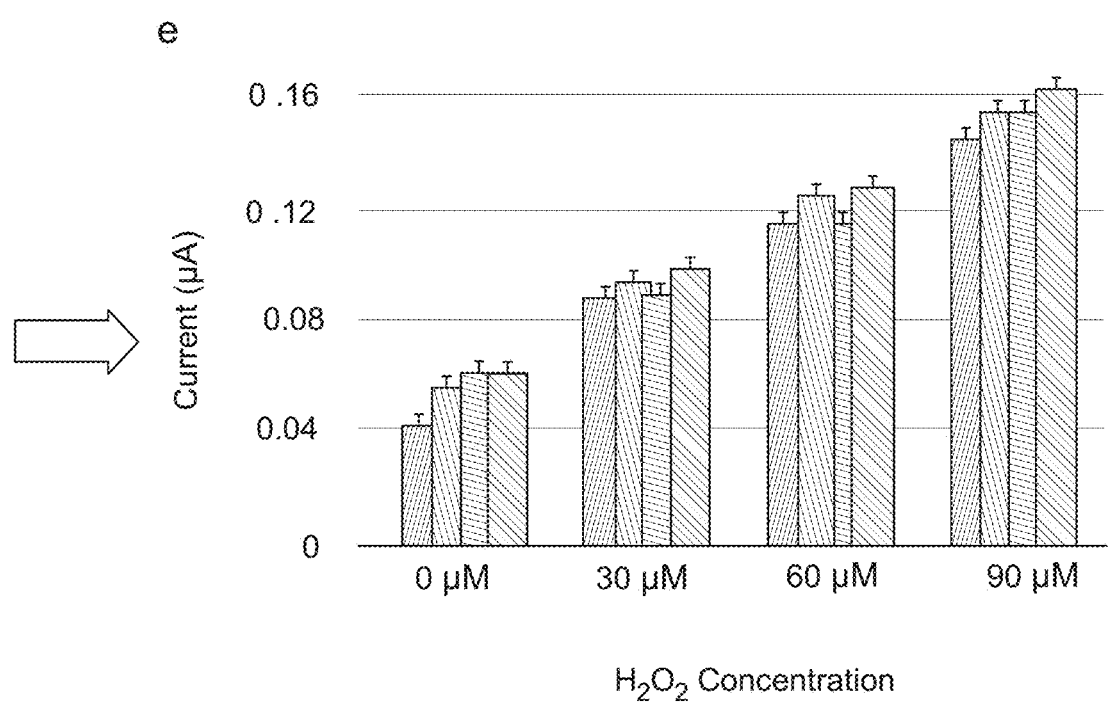

FIG. 20 shows a diagram presenting diagrams and example data associated with a WE/CE/RE ratio study for example implementations of a wearable microneedle sensor platform in accordance with the present technology. FIG. 20 panels ($a_i$) and ($a_{ii}$) show a diagram of an example spiked microneedle array with a 12/12/1 ratio of the WE/CE/RE respectively and its corresponding amperometric signal in the presence of 0 (PBS), 30, 60, and 90 µM of hydrogen peroxide. FIG. 20 panels ($b_i$) and ($b_{ii}$) show a diagram of an example spiked microneedle array with a 12/8/1 ratio of the WE/CE/RE respectively and its corresponding amperometric signal in the presence of 0 (PBS), 30, 60, and 90 µM of hydrogen peroxide. FIG. 20 panels ($c_i$) and ($c_{ii}$) show a diagram of an example spiked microneedle array with a 12/5/1 of the WE/CE/RE respectively and its corresponding amperometry signal in the presence of 0 (PBS), 30, 60, and 90 µM of hydrogen peroxide. FIG. 20 panels ($d_i$) and ($d_{ii}$) show a diagram of an example spiked microneedle array with a 12/3/1 of the WE/CE/RE respectively and its corresponding amperometry signal in the presence of 0 (PBS), 30, 60, and 90 µM of hydrogen peroxide. FIG. 20 panel (e) shows a data plot depicting overlaid results of all three microelectrode ratios and their amperometric responses versus hydrogen peroxide concentration in the sensing medium.

Figure 21:
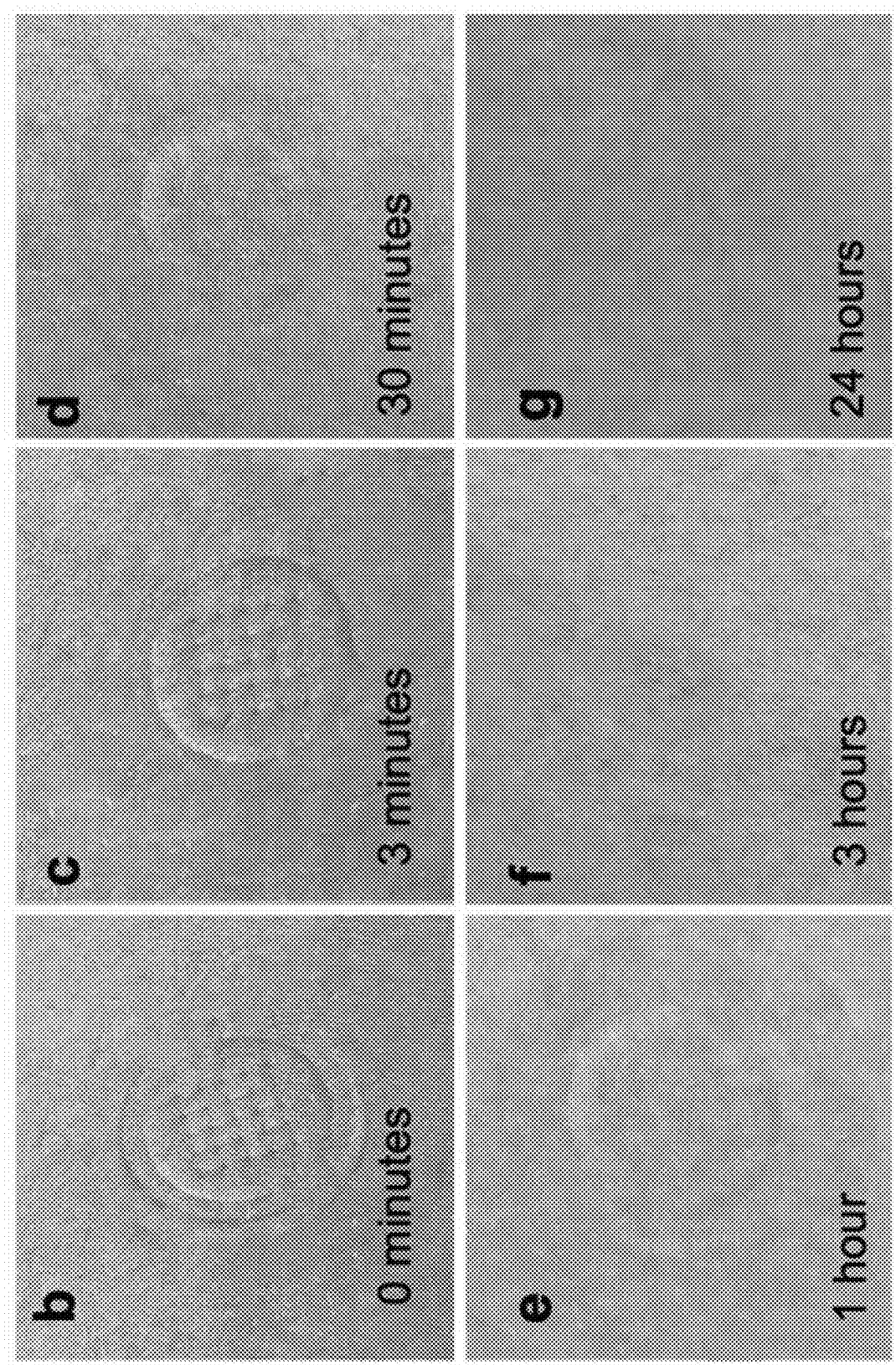
FIG. 21 shows a series of images depicting the visual impact of applying an example individual disposable spiked microneedle array (e.g., having a 5×5 spiked microneedles) to the skin of an individual subject.

FIG. 21 shows a series of images depicting the visual impact of applying an example individual disposable spiked microneedle array (e.g., having a 5×5 spiked microneedles) to the skin of an individual subject. Images (b) through (g) show the example sensor's visual impact on the subject's skin after removal of the sensor patch at 0 minutes, 3 minutes, 30 minutes, 1 hour, 3 hours and 24 hours after the time of removal, respectively.

Figure 22:
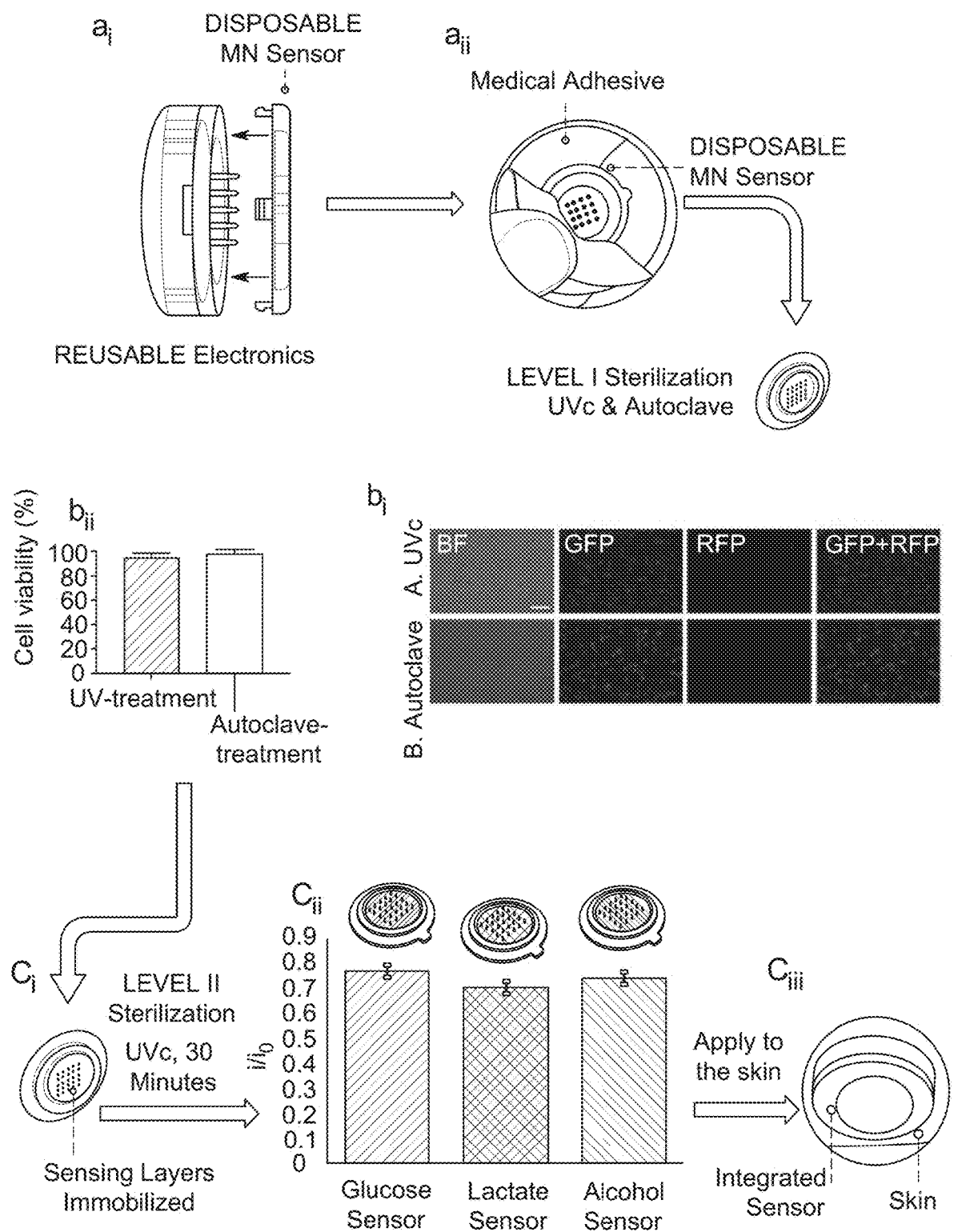
FIG. 22 shows an example sensor sterilization process and example data from cytotoxicity studies in example implementations of a wearable microneedle sensor platform in accordance with the present technology.

FIG. 22 shows an example sensor sterilization process and example data from cytotoxicity studies in example implementations of a wearable microneedle sensor platform in accordance with the present technology. FIG. 22 panel ($a_i$) shows a diagram illustrating an example embodiment of a spiked microneedle array sensor device with a disposable microneedle sensor component and a reusable electronics component. FIG. 22 panel ($a_{ii}$) shows a diagram illustrating a sterilization process of the sensor device's disposable component beginning by a 24-hour autoclave and UVc step, with the corresponding in-vitro cytotoxicity test with J774 cells. FIG. 22 panel ($b_i$) shows representative microscopy images of live and dead cells after incubation with the spiked microneedle sensor patch sterilized by ultraviolet (A) and autoclave (B), where BF refers to brightfield images, GFP refers to green fluorescent protein in fluoresce microscopy images, where GFP: Calcein AM labeled live cells, and RFP: propidium iodide labeled dead cells (scale bar: 50 µm). FIG. 22 panel ($b_{ii}$) shows a bar chart depicting the cytotoxicity of spiked microneedle patch sterilized by ultraviolet and autoclave when incubated with J774 macrophages. FIG. 22 panel ($c_i$) shows a diagram illustrating a level II UVc sterilization process of the disposable sensor component after immobilization of the sensing layers. FIG. 22 panel ($c_{ii}$) shows a bar chart depicting the impact of Level II sterilization on each sensor in terms of their sensitivity drop. FIG. 22 panel ($c_{iii}$) shows an image of a sterilized fully integrated sensor on a human subject skin with the disposable sensor being fully sterilized.

Figure 23A:
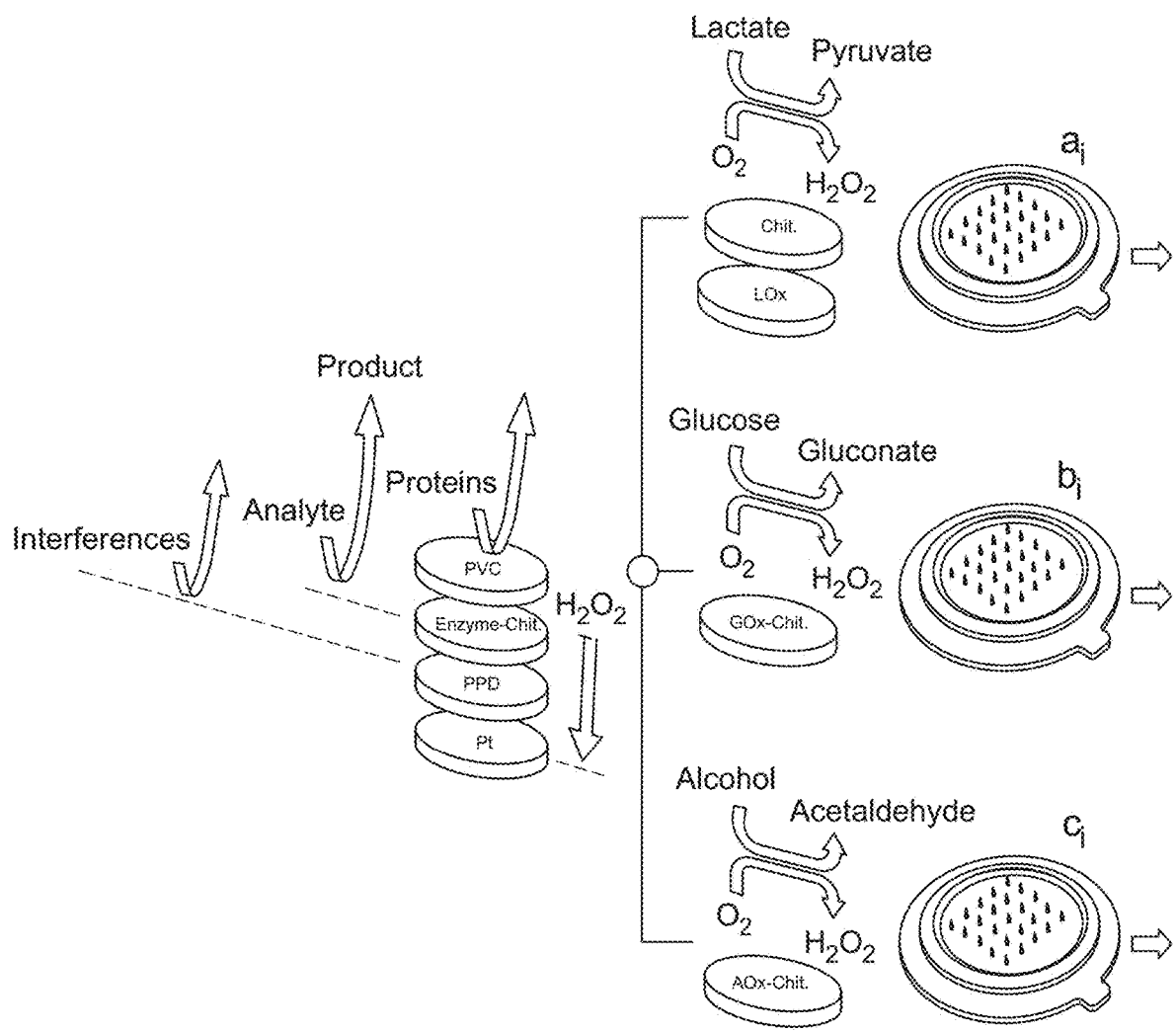
FIG. 23A shows diagrams of an example embodiment of a spiked microneedle array sensor device, in accordance with the present technology, configured for measuring glucose, lactate, and alcohol in example in vitro study.
Figure 23B:
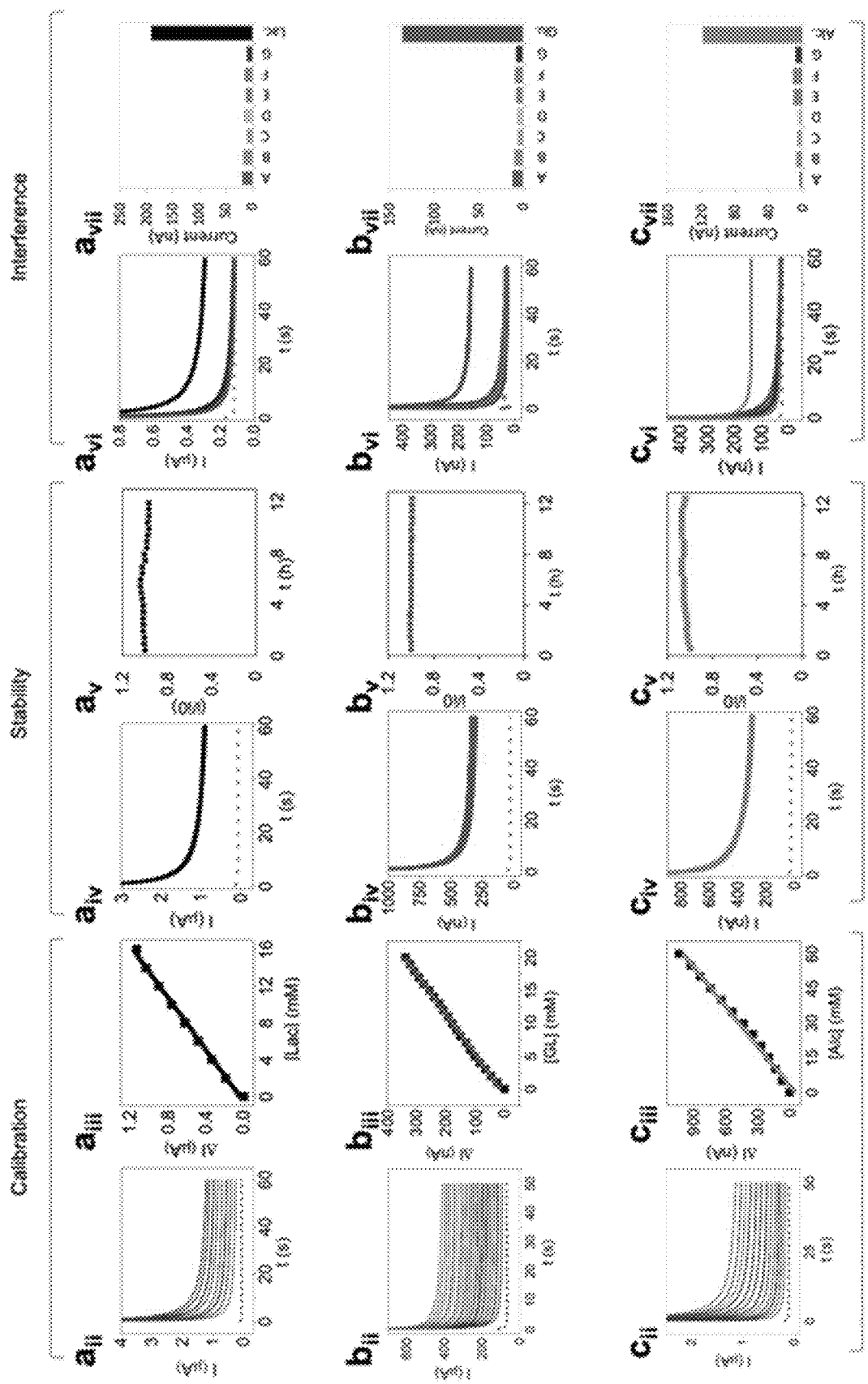
FIG. 23B shows data plots of the example data from the in vitro study using the example spiked microneedle array sensor device shown in FIG. 23A.

FIG. 23A shows diagrams of an example embodiment of a spiked microneedle array sensor device, in accordance with the present technology, configured for measuring lactate, glucose, and alcohol in example in vitro study.

FIG. 23B shows data plots of the example data from the in vitro study using the example spiked microneedle array sensor device shown in FIG. 23A. FIG. 23B panels ($a_{ii}$)-($a_{iii}$) show amperometry calibration curves and the extrapolated linear response of the lactate sensor. FIG. 23B panels ($a_{iv}$)-($a_v$) shows data on the stability of the lactate sensor for 12 hours. FIG. 23B panels ($a_{vi}$)-($a_{vii}$) show data from an interference study of the lactate sensor in artificial solution upon adding (A) ascorbic acid (200 mM), uric acid (500 mM), acetaminophen (100 mM), tryptophan (500 mM), methionine (500 mM), and histidine (500 mM) from B to G, respectively. FIG. 23B panels ($b_{ii}$)-($b_{iii}$) shows amperometry calibration curves and the extrapolated linear response of the glucose sensor. FIG. 23B panels ($b_{iv}$)-($b_v$) shows data on the stability of the glucose sensor for 12 hours. FIG. 23B panels ($b_{vi}$)-($b_{vii}$) show data from an interference study of the glucose sensor in artificial solution upon adding (A) ascorbic acid (200 mM), uric acid (500 mM), acetaminophen (100 mM), tryptophan (500 mM), methionine (500 mM), and histidine (500 mM) from B to G, respectively. FIG. 23B panels ($c_{ii}$)-($c_{iii}$) shows amperometry calibration curves and the extrapolated linear response of the alcohol sensor. FIG. 23B panels ($c_{iv}$)-($c_v$) shows data on the stability of the alcohol sensor for 12 hours. FIG. 23B panels ($c_{vi}$)-($c_{vii}$)

show data from an interference study of the alcohol sensor in artificial solution upon adding (A) ascorbic acid (200 μM), uric acid (500 μM), acetaminophen (100 μM), tryptophan (500 μM), methionine (500 μM), and histidine (500 μM) from B to G, respectively.

Figure 24:
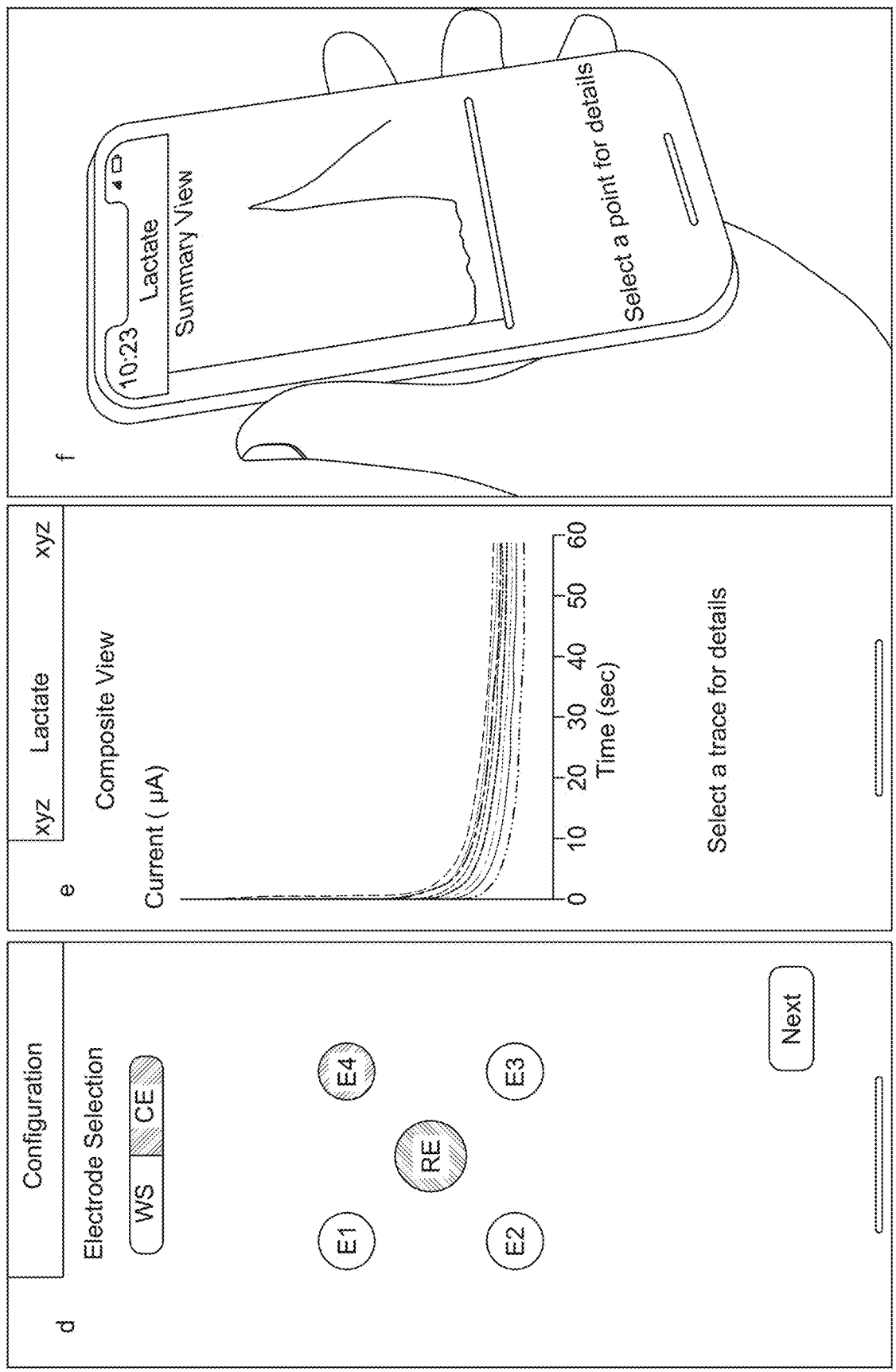
FIG. 24 shows diagrams of an example graphical user interface (GUI) for an example embodiment of a software application (app) to control features and display data for a wearable spiked microneedle array sensor device in accordance with the present technology.

FIG. 24 shows diagrams of an example graphical user interface (GUI) for an example embodiment of a software application (app) to control features and display data for a wearable spiked microneedle array sensor device in accordance with the present technology. Panel (a) shows an example Bluetooth connection page where the app searches for and connect to the sensor patch device. Panel (b) shows an example test setup page in which the amperometry experiment, its time, delay interval between each test is defined. Panel (c) shows an example individual test configuration page, where the test parameters are inserted. Panel (d) shows an example electrode selection page where up to 4 sensors can be defined to operate independently. Panel (e) shows an example composite view page, where all the amperometry results of a particular test is shown. Panel (f) shows an example summary view page, where the sensing profile for over a particular testing duration is viewed.

Figure 25:
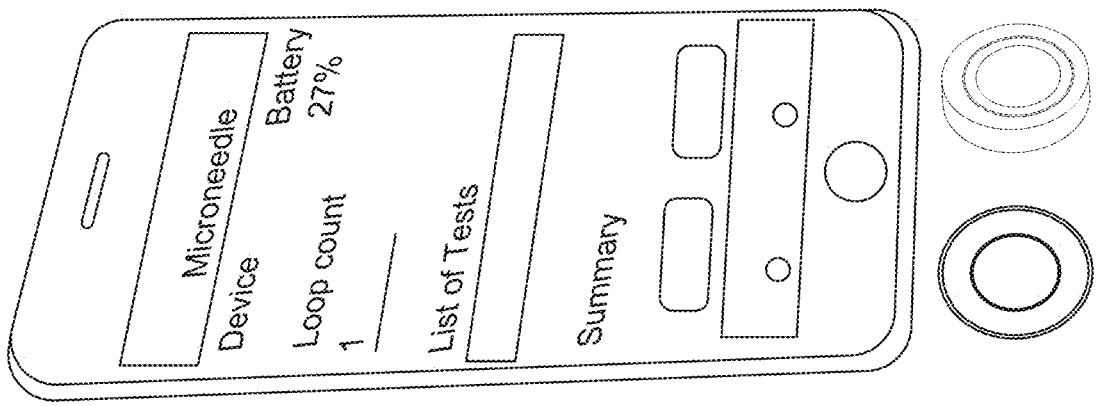
FIG. 25 shows an image depicting a demonstration of an example disposable sensor component and an example reusable component being assembled and placed on the arm of a subject followed by a signal quality test.

FIG. 25 shows an image depicting a demonstration of an example disposable sensor component and an example reusable component being assembled and placed on the arm of a subject followed by a signal quality test.

Figure 26:
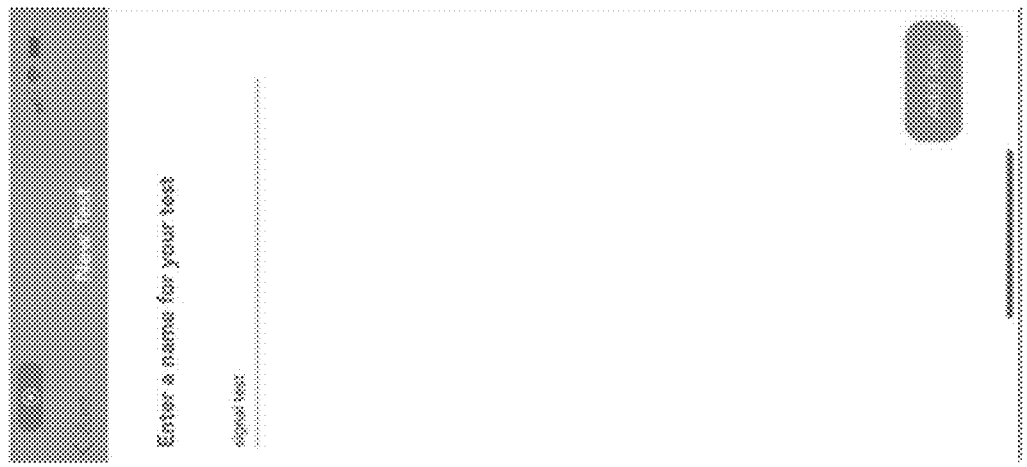
FIG. 26 shows a diagram of an example GUI for an example embodiment of a software application (app), showing an example signal quality test page for conducting after applying the sensor to the skin of a subject.

FIG. 26 shows a diagram of an example GUI for an example embodiment of a software application (app), showing an example signal quality test page for conducting after applying the sensor to the skin of a subject.

Example Implementations with Continuous, Real-Time Monitoring of Single and Multiple Analytes Including Glucose, Lactate, and Alcohol Via a Fully Integrated Wearable Microneedle Platform The disclosed spiked microneedle sensor technology is able to provide continuous monitoring of multiple and individual ISF biomarkers in a compact, non-invasive, wearable sensor platform. Described are further example embodiments and example implementations that demonstrate, e.g., on human subjects, an example spiked microneedle wearable sensor patch, including, the continuous monitoring of lactate, glucose, alcohol, ketone bodies, and sodium (e.g., as model analytes), capable of both individually and simultaneously, with the example results well correlated against standard meters for analytes in a prolonged period of time.

Using the described compact, non-invasive, wearable microneedle sensor platform, molecular level electrochemical signals from skin ISF are (i) continuously and selectively gathered by the epidermis-inserted tips of the spiked microneedles, (ii) carried from the noise-free sensor-electronics interface through the electronics (e.g., whether an engineered reusable electronics unit, or a commercialized potentiostat), and (iii) displayed on a display (e.g., smartphone, and/or personal computer) for a user to view and potentially act accordingly to the signal received. Example implementations of an example compact, wearable microneedle sensor platform for real-time, non-invasive, continuous monitoring of lactate, glucose, alcohol, ketone bodies (e.g., beta-hydroxybutyrate), and sodium are discussed below.

Figure 27:
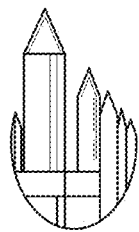
FIG. 27 shows schematic views of an example wearable, non-invasive electrochemical sensor patch device in accordance with the present technology.
Figure 27:
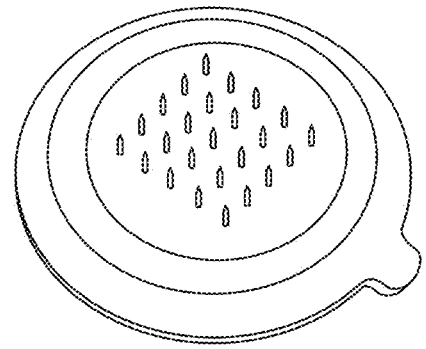
Figure 27:
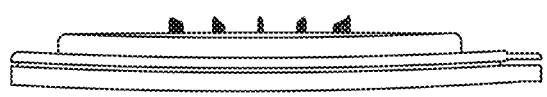
Figure 27:
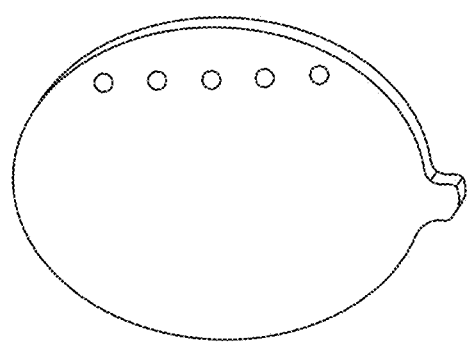

FIG. 27 shows schematic views of an example wearable, non-invasive electrochemical sensor patch device in accordance with the present technology. The schematic shows an illustration of an example spiked microneedle geometry (top-left) for an array of spiked microneedles arranged on a microneedle patch (top-right, bottom-left, and bottom-right).

Figure 28A:
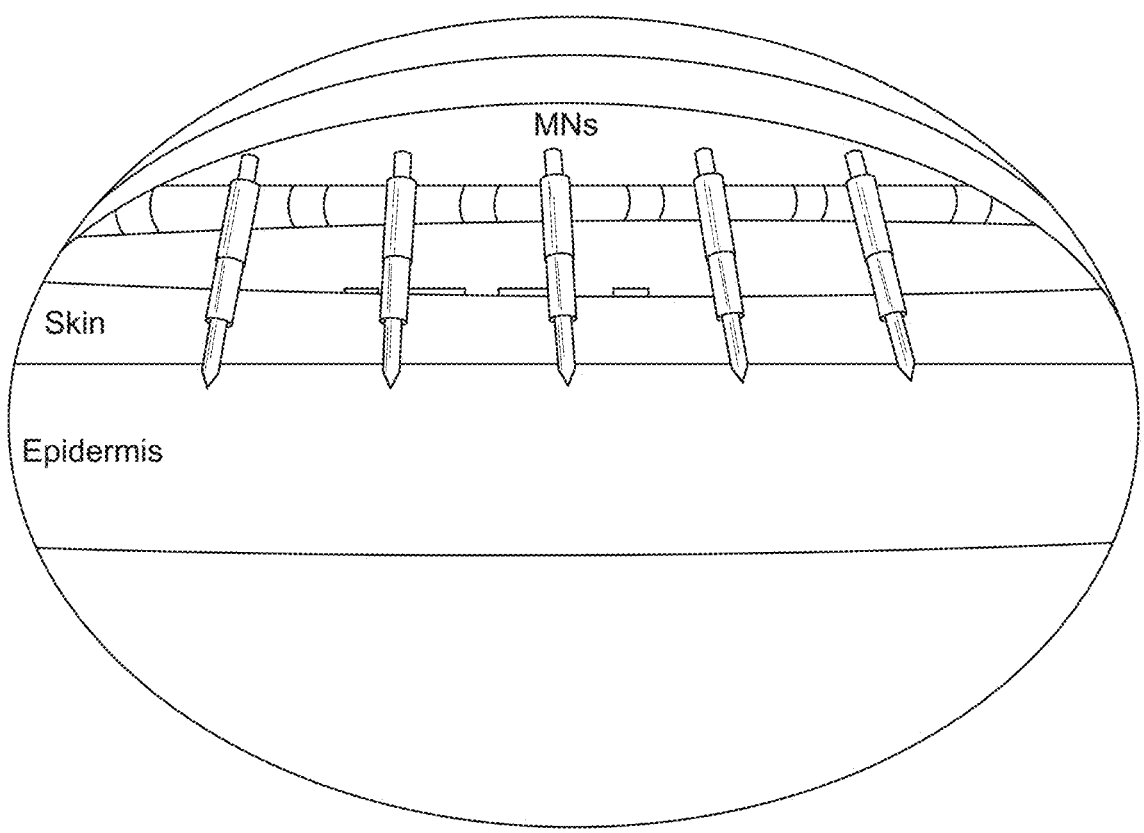
FIG. 28A shows an illustration of an array of spiked microneedles of an example wearable, non-intrusive electrochemical sensor patch inserted into skin of a user.

FIG. 28A shows an illustration of an array of spiked microneedles of an example wearable, non-intrusive electrochemical sensor patch inserted into skin of a user, as implemented in the example implementations for real-time, non-invasive, continuous monitoring of lactate, glucose, alcohol, ketone bodies, and sodium. The example wearable, non-intrusive spiked microneedle electrochemical sensor patch was configured to include (i) a spiked microneedle microelectrode design, to accommodate (ii) one or more reagent sensing layers (on the microneedle microelectrode sensor) for single- or multi-analyte sensing, and (iii) new cost-effective, scalable fabrication techniques that effectively seal the microneedle array substrate to a cover to ensure high signal-to-noise signal detection and facilitate a disposable sensing component that can be interfaced with a reusable electronics component.

Figure 28B:
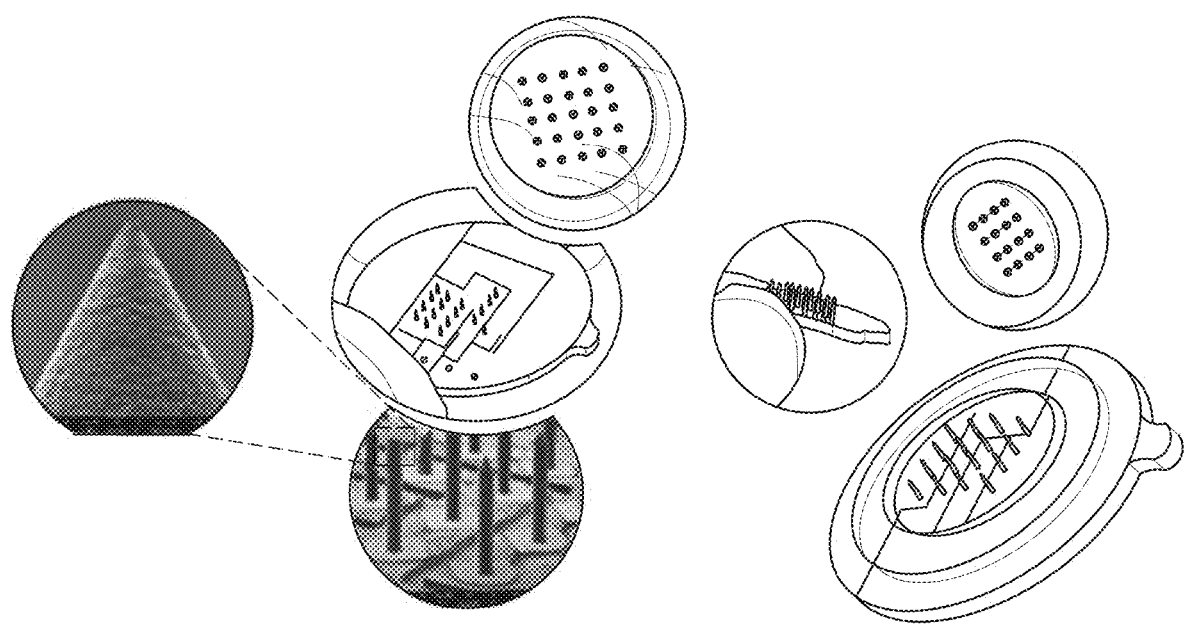
FIG. 28B shows images of the example wearable, non-intrusive electrochemical sensor patch from example implementations monitoring of lactate, glucose, alcohol, ketone bodies, and/or sodium in ISF of a subject's skin.

FIG. 28B shows images of the example wearable, non-intrusive electrochemical sensor patch, e.g., including the spiked microneedle array of the device shown in the illustration of FIG. 28A, which was used in example implementations for monitoring of lactate, glucose, alcohol, ketone bodies (e.g., beta-hydroxybutyrate), and/or sodium in ISF of a subject's skin. FIG. 28B shows a zoomed image of an example spiked microneedle tip, as well as images of the substrate surface with the spiked microneedle array and of the subject's skin after withdrawal of the spiked microneedle sensor array.

The example wearable, non-intrusive spiked microneedle electrochemical sensor patch was configured to have cone-shaped, solid spiked microneedles designed in an array for modifications of reagent sensing layer(s) and with specific geometric ranges and configurations in a single patch. For example, cone-shaped, solid microneedles can be structured to include 850 μm to 1,000 μm height and a diameter of 150-250 μm. The spiked microneedles can be arranged in a single patch for dual and single sensing, with spacing between the sensing regions for the dual sensors can be adjusted to 7-20 mm towards minimizing the cross-talk between the sensors. The spiked microneedle array patch can be sealed by a biocompatible photocurable resin that is drop-cast in between the microneedle cover and the microneedle base. For example, the resin is naturally moved to a separation line (e.g., 350-250 micron or 350-150 micron diameter shift in by capillary forces to the line insulating the microelectrodes up to the line in a reproducible manner. In the example implementations for monitoring of lactate, glucose, alcohol, ketone bodies (e.g., beta-hydroxybutyrate), and/or salt ions (e.g., sodium) in ISF of a subject's skin, the spiked microneedles included a winding protrusion (e.g., spiral-winding projection), such as the example spiked microneedle microelectrode shown previously in FIG. 2A.

The microneedle cover can be configured as a ring cover for the circular-shaped microneedle array substrate. The use of the microneedle cover assists in promoting pain-free insertion of the spiked microneedles into the skin when implementing the wearable spiked microneedle array sensor device. For instance, the microneedle cover can be designed and integrated on the microneedle sensor array. In example embodiments of a ring cover, the microneedle cover can provide a curve for the skin for a better penetration of the microneedles as well as protection of the microneedle array base from electronically contacting with the skin. The curvature of the ring cover on the skin can enhance the ease of penetration of the microneedles with negligible sensing of the penetration. An example of the ring cover used in the example implementations for glucose, lactate, alcohol, ketone bodies, and salt ion single- and/or multi-analyte monitoring is shown in FIG. 27.

The example wearable, non-intrusive spiked microneedle electrochemical sensor patch includes an engineered electronic interface between electrically-conductive contacts of or coupled to the spiked microneedle electrode structures and the corresponding electrically-conductive contacts of the electronics unit, e.g., via a friction E-Connection system. For example, friction-based pins and the corresponding pinholes allow for a robust, noise-free contact between the sensor and electronics components. In some embodiments, for example, the friction-based pins are mechanically aligned to the example PCB using the custom designed PCB/Pin soldering method with perpendicular intersection. Example embodiments of the friction E-Connection system is described in the earlier discussion pertaining to FIGS. 4A-4C and FIG. 5.

The example wearable, non-intrusive spiked microneedle electrochemical sensor patch was configured to include one or more reagent sensing layers (on the microneedle microelectrode sensor) for single- or multi-analyte sensing, including but not limited to lactate/glucose, alcohol/glucose, lactate/glucose/alcohol, glucose/ketone bodies, lactate/ketone bodies, lactate/sodium, or any individual or combination of lactate, glucose, alcohol, ketone bodies (e.g., beta-hydroxybutyrate), or salt ions (e.g., sodium) for continuous single- or multi-analyte monitoring. In example implementations for glucose monitoring, the example wearable, non-intrusive spiked microneedle electrochemical sensor patch was configured by electrodepositing poly-o-phenylene diamine (PPD) as the inner layer of the sensor, followed by drop casting an optimized composition of the mixture glucose oxidase (GOx)-Chitosan and glutaraldehyde crosslinker (and/or polyethylene glycol diglycidyl ether (PEGDE) crosslinker); and where a final step included coating the sensor with an outer polymer layer of polyvinyl chloride (PVC) containing an optimized amount of a non-inionic surfactant (e.g., Triton x-100). In example implementations for lactate monitoring, the example wearable, non-intrusive spiked microneedle electrochemical sensor patch was configured by electrodepositing poly-o-phenylene diamine (PPD) as the inner layer of the sensor, followed by drop casting an optimized amount of the enzyme lactate oxidase (LOx) and a crosslinker (e.g., PEGDE or glutaraldehyde), which was followed by sequential drop-casting of Chitosan and PVC-surfactant polymer membranes. In example implementations for alcohol monitoring, the example wearable, non-intrusive spiked microneedle electrochemical sensor patch was configured by electrodepositing PPD as the inner layer of the sensor, followed by drop casting an optimized composition of the mixture alcohol oxidase (AOx)-Chitosan, and where a final step included coating the sensor with an outer polymer layer of PVC containing Triton x-100 surfactant.

In example implementations for ketone monitoring, the example wearable, non-intrusive spiked microneedle electrochemical sensor patch was configured by the following. A beta-hydroxybutyrate dehydrogenase (HBD) enzyme and a ferrocene derivative molecule are both covalently attached to a branched polyethyleneimine (PEI) on the surface of carbon coated spiked microneedle structures, followed by glutaraldehyde crosslinking and coating by a biofouling resistant outer polymer layer, PVC including a specific concentration of a non-ionic surfactant, triton X-100.

In example implementations for hydration monitoring via target salt ions (e.g., sodium), the example wearable, non-intrusive spiked microneedle electrochemical sensor patch was configured by the following. Sodium ionophore, ion exchanger, plasticizer and PVC polymer are mixed in tailored optimized ratios and dissolved in tetrahydrofuran solvent to form the sodium sensitive cocktail layer on the surface of carbon coated spiked microneedle structures.

Figure 28C:
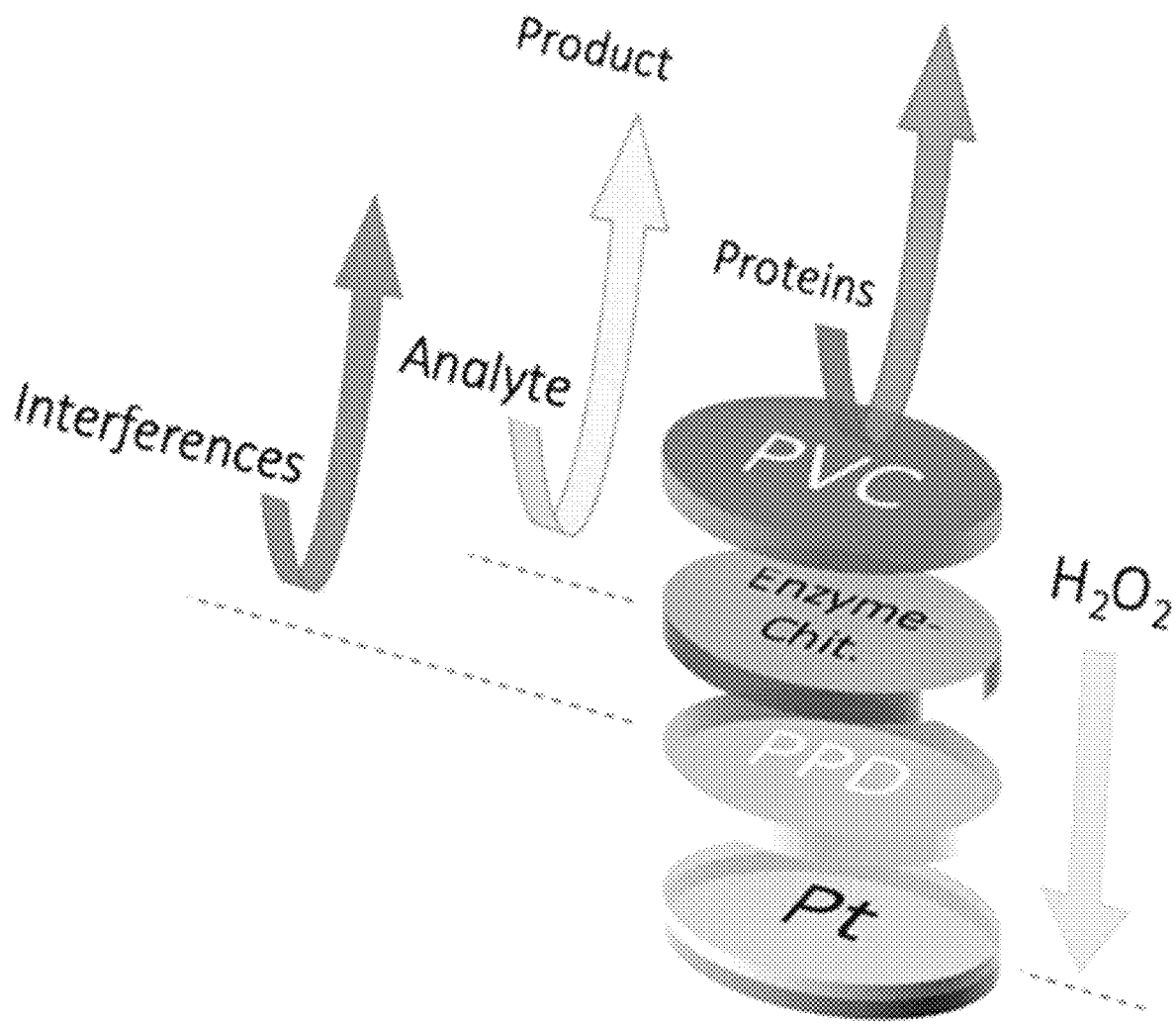
FIG. 28C shows an illustration depicting example sensing layers that can be deposited on particular spiked microneedles, enabling sensitivity of the sensors to specific biomarkers.

FIG. 28C shows an illustration depicting the sensing layers that can be deposited on particular spiked microneedles, enabling sensitivity of the sensors to specific biomarkers. For example, the spiked microneedle structures are configured as electrodes, e.g., by a reproducibly coating process of specific enzymes and polymers to create a unique composition/sequence of each for electrochemical sensing of specific biomarkers outlined above with respect to (i) continuous glucose monitoring, (ii) continuous lactate monitoring, (iii) continuous alcohol monitoring, as examples. The diagram in FIG. 28C shows an example schematic illustration of such coating process. For example, in each of the example spiked microneedle sensors, the enzyme loadings and the thickness of the polymer layers along with the crosslinking degree are judiciously optimized to enable sensitive and selective analyte sensing within their physiological range while minimizing the biofouling and foreign body response issues and hence maximizing the operational lifetime of the sensors. The modification schemes for the microelectrodes configured for continuous glucose monitoring, lactate monitoring, and alcohol monitoring is also shown in FIG. 23A, discussed above.

For the example implementations of single- and/or multiple-analyte sensing of glucose, lactate, alcohol, ketone bodies, and/or salt ions, the example wearable, non-intrusive spiked microneedle electrochemical sensor patch was fabricated based on the disclosed cost-effective microneedle sensor fabrication method, e.g., using micro-machining, 3D printing, and/or micro-injection molding techniques, e.g., fabrication strategy sequence, parameters, and tooling, which can employ the example method 1900 discussed in FIG. 19.

Figure 29:
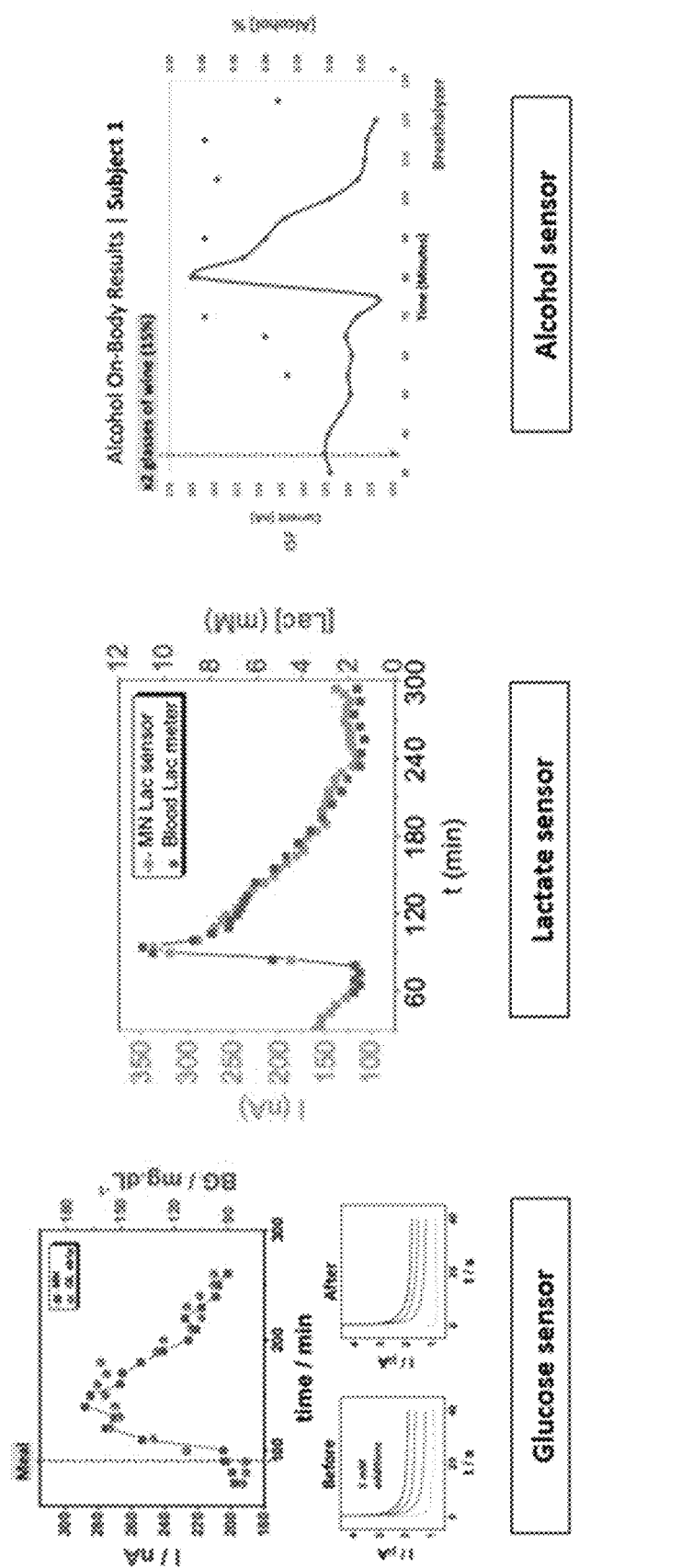
FIG. 29 shows data plots showing example human trial results for continuous monitoring of glucose, lactate, and alcohol using the example wearable, non-intrusive electrochemical sensor device shown in FIGS. 28A-28B.

FIG. 29 shows data plots showing example human trial results for continuous monitoring of glucose (left plot), lactate (center plot), and alcohol (right plot) using the example wearable, non-intrusive electrochemical sensor device shown in FIGS. 28A-28B, with the data plots also showing validation data for these analytes recorded by a conventional instrument including a blood glucose meter, a blood lactate meter, and a breathalyzer, respectively (e.g., as a control). As the data plots of FIG. 29 show, the data measured by the wearable, non-intrusive electrochemical sensor device matches with the data measured by the conventional instrument, particularly for the glucose and lactate measurements.

Figure 30:
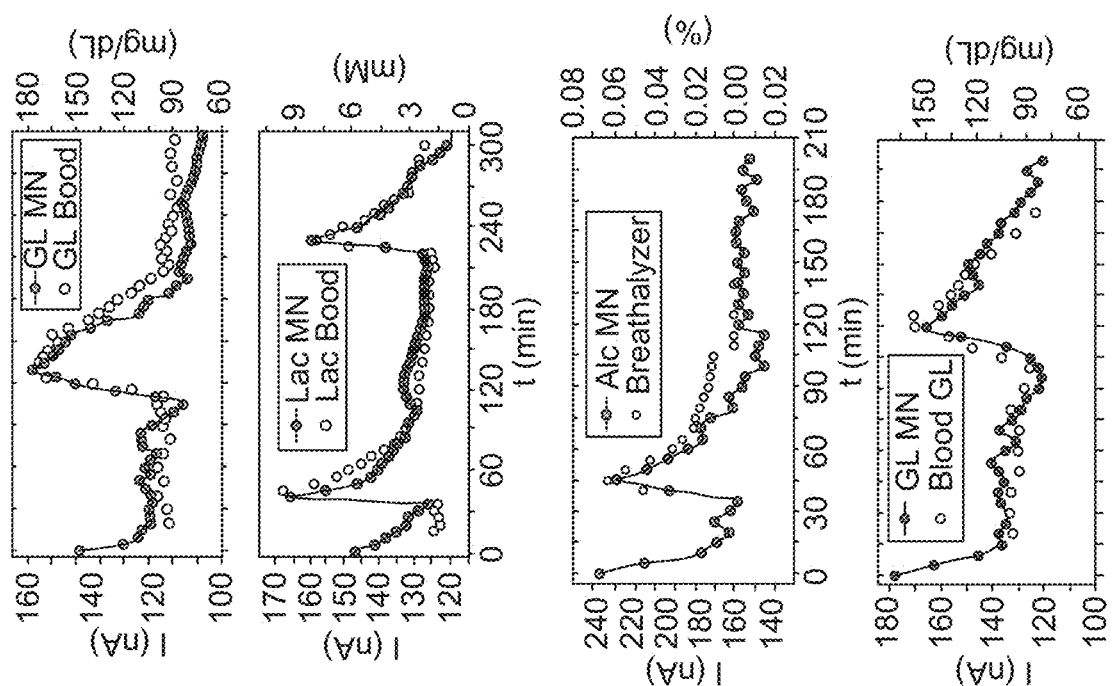
FIG. 30 shows data plots showing example on-body, multiplexed sensing for glucose and lactate or alcohol on two human subjects using the example wearable, non-intrusive electrochemical sensor patch of FIGS. 28A-28B.
Figure 30:
Figure 30:
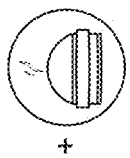
Figure 30:
Figure 30:
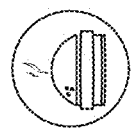
Figure 30:
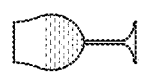

FIG. 30 shows data plots showing example on-body, multiplexed sensing for (A) glucose and lactate and (B) glucose and alcohol on two human subjects, respectively, using the example wearable, non-intrusive electrochemical sensor patch of FIGS. 28A-28B. In the example implementations, the human subject A underwent exercise, eating, and more exercise (top data set) while the sensor was continuously measuring the target analytes glucose and lactate. Also, in the example, implementations, the human subject B drank alcohol and ate (bottom data set) while the sensor was continuously measuring the target analytes glucose and alcohol.

Figure 31:
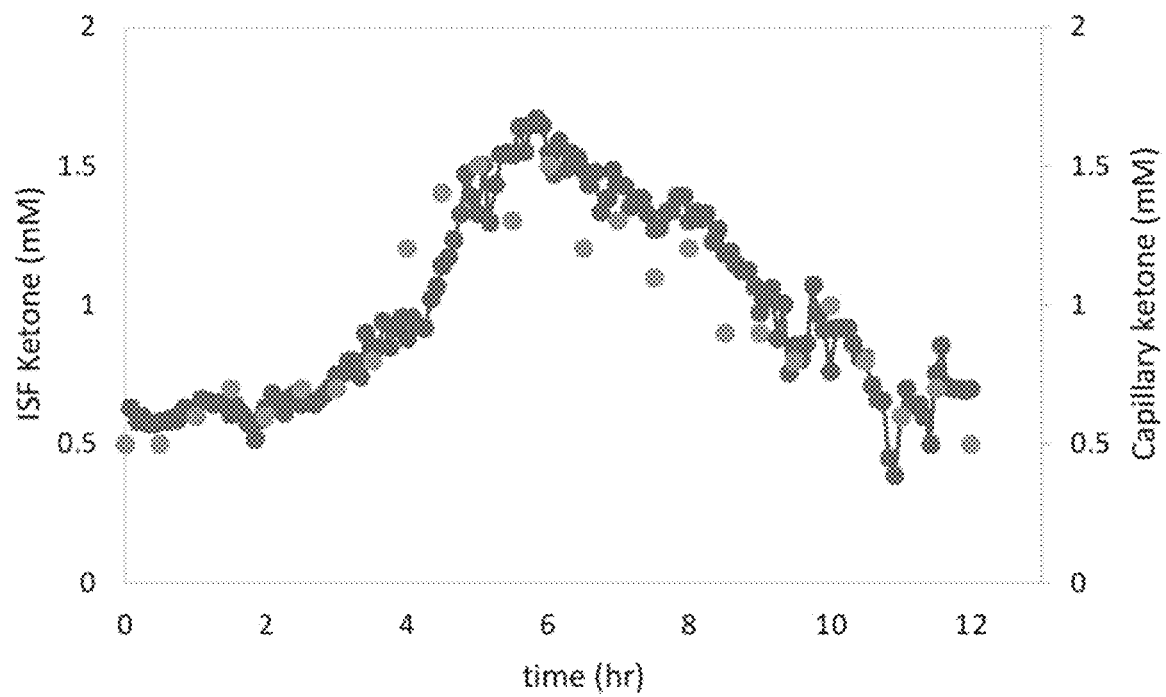
FIG. 31 shows a data plot showing example human trial results for continuous monitoring of ketone bodies with validation data using the example wearable, non-intrusive electrochemical sensor patch of FIGS. 28A-28B.

FIG. 31 shows a data plot showing example human trial results for continuous monitoring of ketone bodies (e.g., beta-hydroxybutyrate) using the example wearable, non-intrusive electrochemical sensor patch of FIGS. 28A-28B. In the data plot, the beta-hydroxybutyrate data is shown by the darker-colored, connected (blue) dots and left axis, along with validation data performed using a conventional, commercially-available instrument shown by the lighter-colored, unconnected (orange) dots and the right axis. This example data demonstrates the example wearable, non-intrusive electrochemical sensor patch used in the example ketone body monitoring study effectively characterized the amount of beta-hydroxybutyrate in the human subject.

Figure 32:
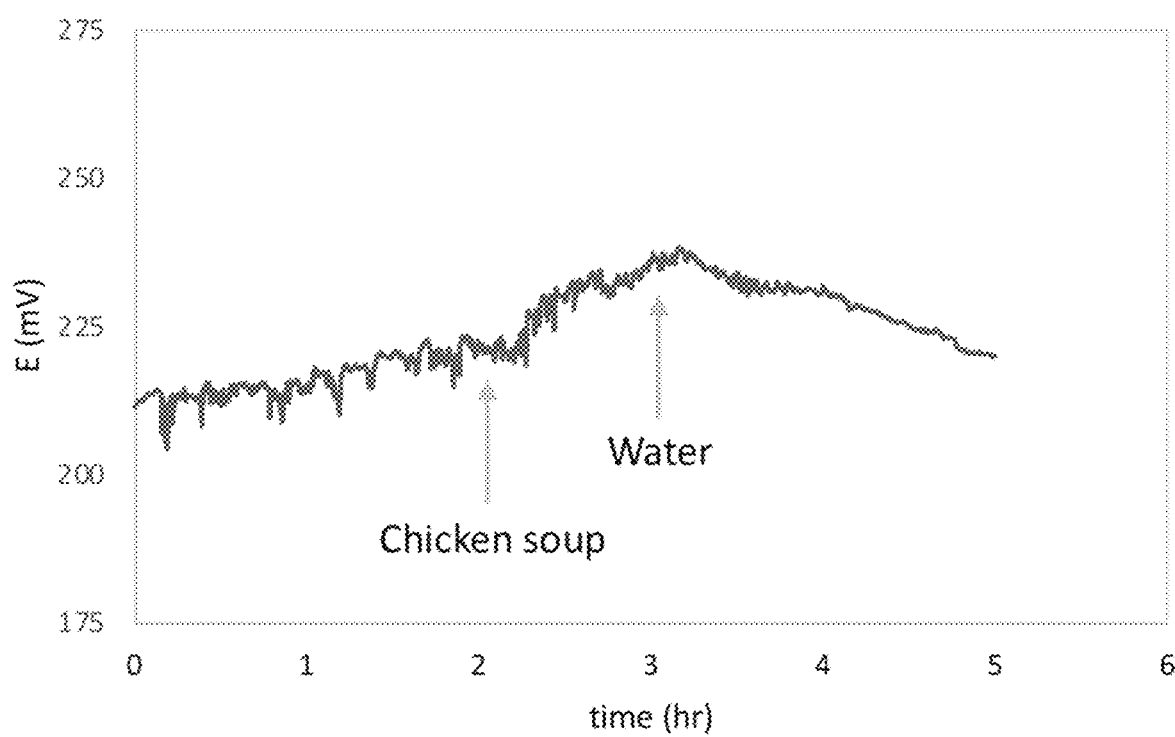
FIG. 32 shows a data plot showing example human trial results for continuous monitoring of hydration levels of the body (via monitoring of sodium ion levels) using the example wearable, non-intrusive electrochemical sensor patch of FIGS. 28A-28B.

FIG. 32 shows a data plot showing example human trial results for continuous monitoring of hydration levels of the body (via monitoring of sodium ion levels) using the example wearable, non-intrusive electrochemical sensor patch of FIGS. 28A-28B. In the data plot, the arrows show the time points when the human subject orally intakes specific amounts of a salty chicken soup and then water. This example data demonstrates the example wearable, non-intrusive electrochemical sensor patch can be used monitoring hydration levels, e.g., via sodium monitoring, in human subjects, e.g., providing real-time information about the subject's level of hydration.

Figure 33A:
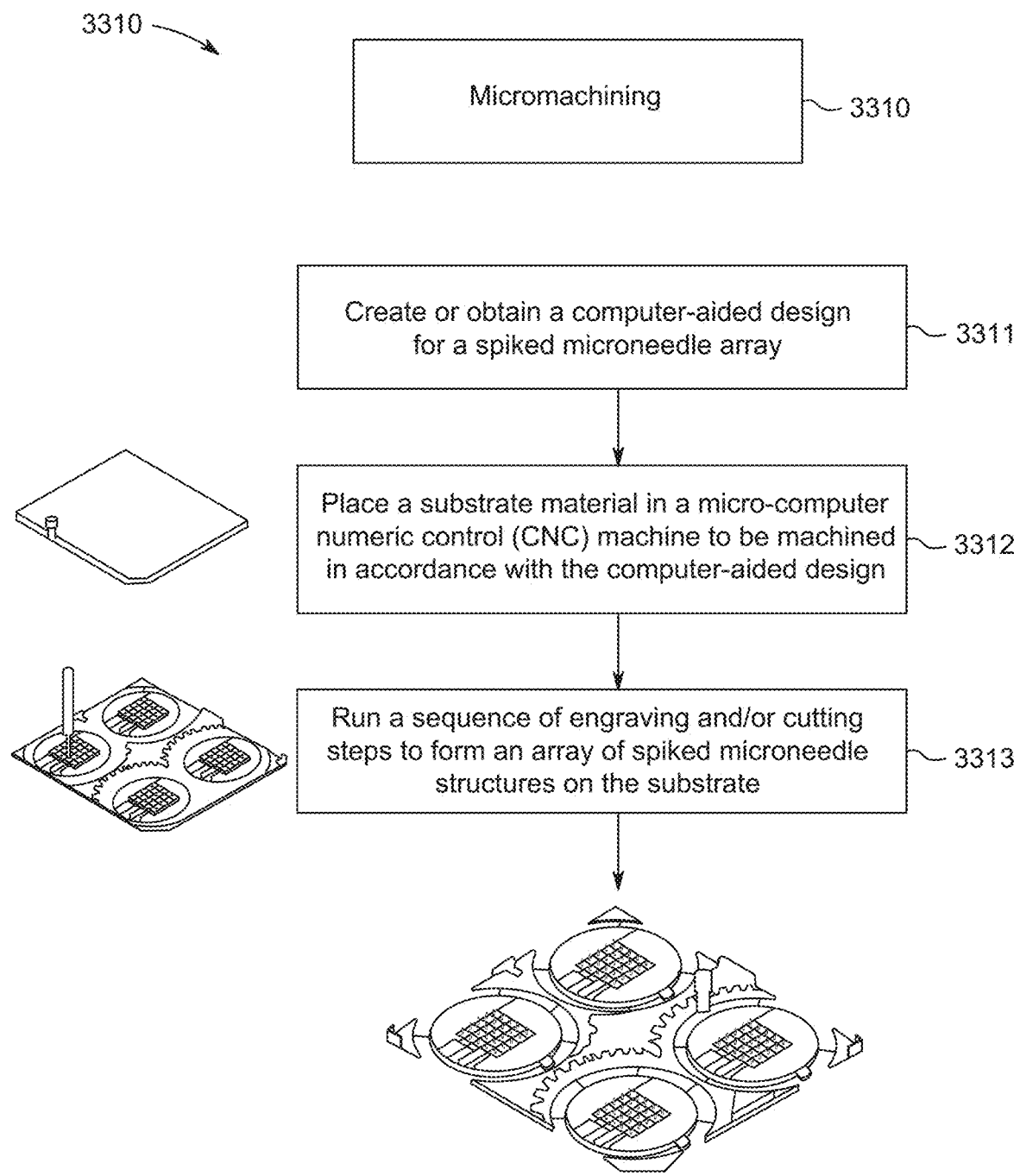
FIG. 33A shows an illustrated flow diagram of an example embodiment of a fabrication method for micromachining of a spiked microneedle sensor array in accordance with the present technology.

FIG. 33A shows an illustrated flow diagram of an example embodiment of a fabrication method 3310 for micromachining of a spiked microneedle sensor array in accordance with the present technology. In some implementations of the method 3310, the method 3310 is used to micro-machine an array of spiked microneedles protruding from a substrate with an array of microchannels formed on the surface or within the substrate. The method 3310 includes a process 3311 to create or obtain a computer-aided model/design (e.g., CAM/CAD design in a 3D modeling software, such as Fusion 360, Solidworks, etc.) for a spiked microneedle array, including 3D structures including spiked microneedles (and optionally, microchannels). The method 3310 can include a process 3312 to place a substrate (e.g., bulk material, such as PMMA) in a micro-computer numerical control (CNC) machine to be machined in accordance with the design. The method 3310 can include a process 3313 (for implementing CNC machining) to run a sequence of engraving and/or cutting steps to form the array of spiked microneedle structures on the substrate, e.g., using the appropriate CNC bit and/or drill at each sequence.

In some implementations of the method 3310, for example, the engraving/cutting of holes (at process 3313) can employ drill bits ranging from 50-1,000 μm, where the engraving/cutting by the CNC machine applies a spindle rate 500 to 25,000 rpm with the step size ranging from 1 μm-1 mm. Also, in some implementations of the process 3310, for example, for bulk material removal (at process 3313), a drilling strategy can include a 500 rpm to 12,000 rpm spindle speed, 40-120 m/min surface speed, 50-1,000 mm/min plunge federate, and feed per revolution of 0.01-0.1 mm, and retract federate of 50-1,000 mm/min.

In some implementations of the method 3310, for example, the process 3313 includes a finetuning micro-engraving process; where, in some embodiments of the finetuning micro-engraving process, a 2D adaptive (or 2D pocket) clearing or a 3D adaptive (or 3D pocket) clearing strategy for the engraving step can include using a CNC bit flat 2-4 flute, with diameters of 100-500 μm, Spindle Rates of 500 to 15,000 rpm, and feed rate of 20-100 mm/min.

Figure 33B:
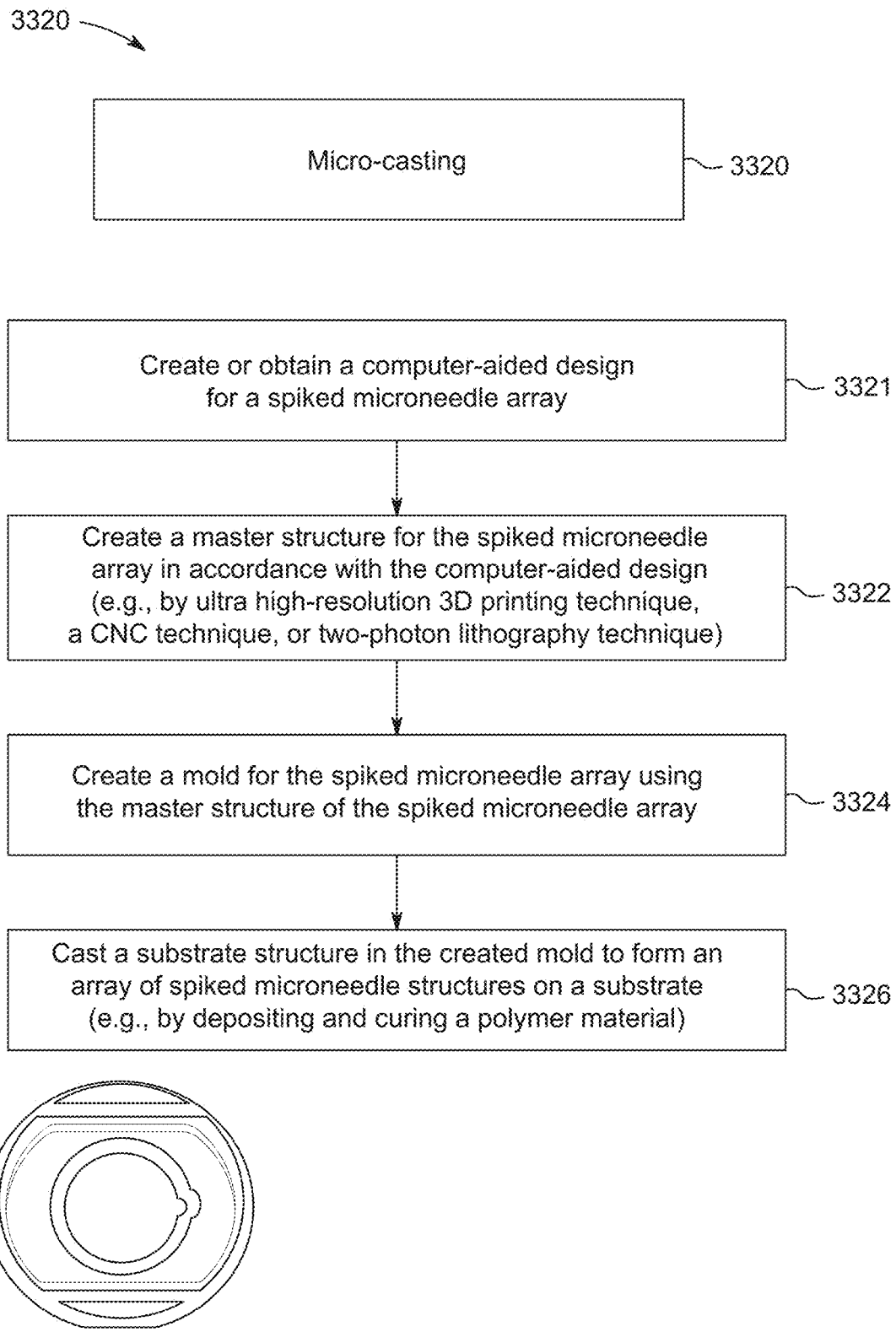
FIG. 33B shows an illustrated flow diagram of an example embodiment of a fabrication method for microcasting of a spiked microneedle sensor array in accordance with the present technology.

FIG. 33B shows an illustrated flow diagram of an example embodiment of a fabrication method 3320 for microcasting of a spiked microneedle sensor array in accordance with the present technology. In some implementations of the method 3320, the method 3320 is used to micro-cast an array of spiked microneedles protruding from a substrate structure with an array of microchannels formed on the surface or within the substrate, which involves a three-phase process including a first phase to create a master structure for a mold of the spiked microneedle array, a second phase to create a mold of the spiked microneedle array for repeatable micro-casting manufacturing, and a third phase of producing units of the spiked microneedle array via micro-casting from the mold.

The method 3320 includes a process 3321 to create or obtain a computer-aided model/design (e.g., CAM/CAD design in a 3D modeling software, such as Fusion 360, Solidworks, etc.) for a spiked microneedle array, including 3D structures including spiked microneedles (and optionally, microchannels). The method 3320 can include a process 3322 to create a master structure for the spiked microneedle array in accordance with the computer-aided model/design. In some implementations of the process 3322, for example, where the features of the spiked microneedle array include high resolution features (e.g., 5 μm or less), the process 3322 can include utilizing an ultra-high resolution 3D printing technique, a CNC technique (e.g., as in the process 3312), or two-photon lithography technique to create the master structure for the array. In some implementations of the process 3322, for example, where the features of the spiked microneedle array do not include ultra-high resolution features, the process 3322 can include utilizing a micro-machining technique or a photolithography technique.

The method 3320 includes a process 3324 to create a mold for the spiked microneedle array using the master structure of the spiked microneedle array. In some implementations of the process 3324, for example, the process 3324 includes creating the mold using molding material (e.g., including but not limited to polydimethylsiloxane (PDMS) or a silicone-based elastomer) by depositing the molding material onto and/or into the master structure; degassing and heat treating the molding material on/in the master structure to produce the mold of the spiked microneedle array, and removing the master structure from the produced mold. In implementations of the method 3320, for example, the process 3324 can be repeated to make multiple molds from a single master structure produced in the process 3322.

The method 3320 includes a process 3326 to cast a substrate structure in the created mold to form an array of spiked microneedle structures on a substrate. In some implementations of the process 3326, for example, the process 3326 includes casting a biocompatible polymer material (e.g., UV-curable resin) by depositing the biocompatible material into the mold, degassing the deposited biocompatible material in the mold, and curing the degassed biocompatible material, e.g., by UV light and/or heat. In implementations of the method 3320, for example, the process 3326 can be repeated to make multiple spiked microneedle array units from a single mold produced in the process 3324.

Example Embodiments of Spiked Microneedle Sensor Arrays with a Microporous Tip, Body Channels, and/or Interlocking Edges The disclosed spiked microneedle sensor technology is able to provide continuous monitoring of multiple and individual ISF biomarkers in a compact, non-invasive, wearable sensor platform in a manner that both increases the signal-to-noise ratio (e.g., by reducing electrical noise typically caused at the skin-electrode interface) while reducing the pain caused to the subject user from insertion, wearing, and/or removal of the microneedle sensor contingent from the subject user's skin. Described are further example embodiments and example implementations that demonstrate, e.g., on human subjects, how certain features of the example spiked microneedle structures can provide these capabilities for a spiked microneedle array sensor device, in accordance with the present technology.

Figure 34A:
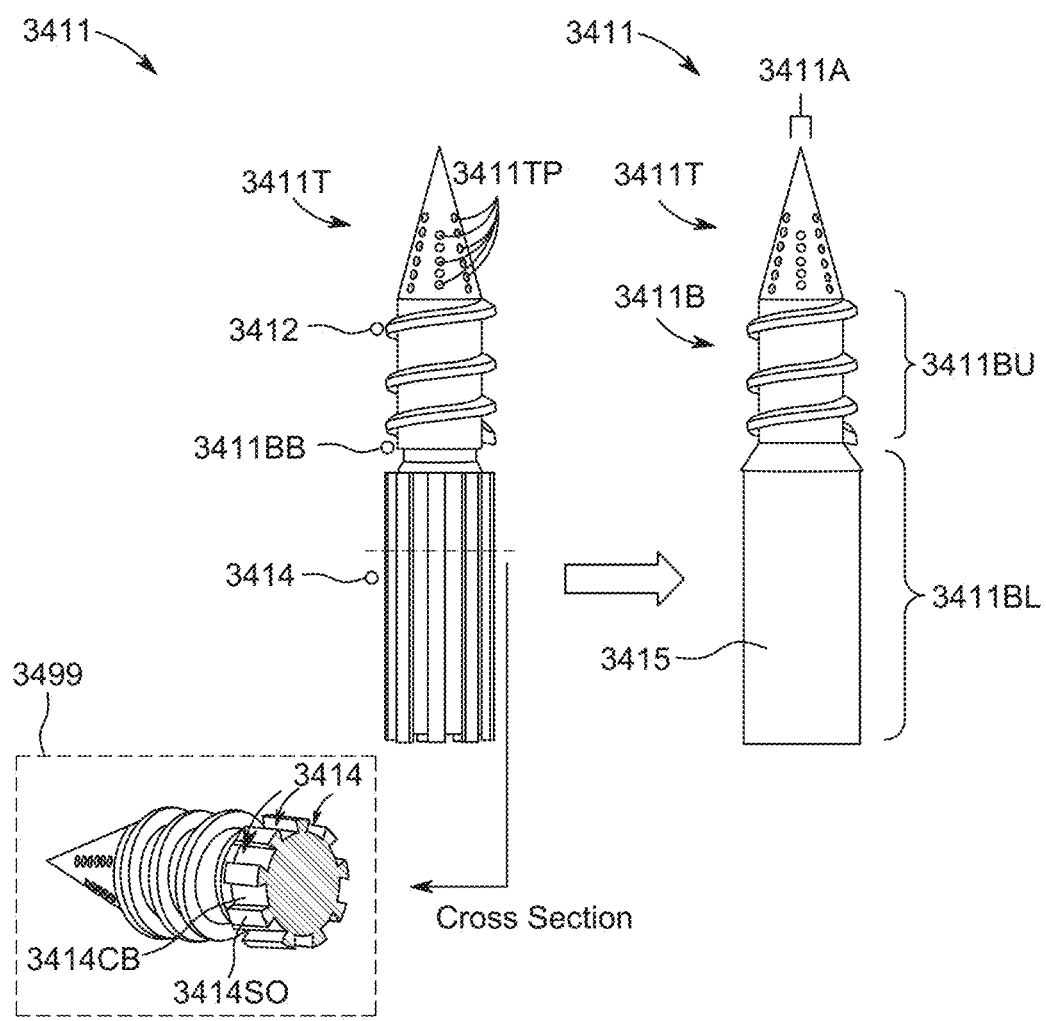
FIG. 34A shows illustrative diagrams showing various aspects of an example embodiment of a spiked microneedle structure in accordance with the present technology.

FIG. 34A shows illustrative diagrams showing various aspects of an example embodiment of a spiked microneedle structure, labeled 3411, which can be employed in a spiked microneedle array of any of the disclosed embodiments of the device 100. The example spiked microneedle structure 3411 includes a body region 3411B culminating at a tip region 3411T having at a terminal end (apex 3411A). In the example, the body region 3411B includes a cylindrical shape, and the tip region 3411T includes a conical tip. In some embodiments, the conical tip includes a 28° tip angle at apex 3411A (e.g., having a diameter of 200 µm and a height of 355 µm), but it is understood that the size of the tip region 3411T and/or apex 3411A may vary (e.g., depending on a desired application). The body region includes an upper segment 3411BU and a lower segment 3411BL, which are interfaced at a boundary region 3411BB.

In some embodiments, the spiked microneedle structure 3411 can include a protrusion 3412 that winds around the at least a portion of the upper segment 3411BU of the body region 3411B. In the example shown in FIG. 34, the protrusion 3412 of the spiked microneedle structure 3411 includes a spiral protrusion, e.g., which continuously winds from a top part of the upper segment 3411BU to a bottom part of the upper segment 3411BU, e.g., to the boundary region 3411BB. Whereas, in some embodiments, for example, the protrusion 3412 may be a discontinuous protrusion with one or more gaps between a plurality of protrusion portions that wraps around the at least a portion of the upper segment 3411BU. Also, in some embodiments, for example, the protrusion 3412 may be of a spiral configuration of varying spiral angles. For example, the protrusion 3412 may be a spiral protrusion having a spiral angle of at least 10°, or of at least 20°, or of at least 30°, or of at least 40°, or of at least 50°, or of at least 60°, etc. to 89°, which can depend on the size of the microneedle structures, which itself can be based on the desired application or subject who will receive the microneedle sensor array. In some embodiments for human subjects, for example, the protrusion 3412 may be a spiral protrusion having a spiral angle in a range of at least 10° to 60°. In some embodiments of the spiked microneedle structure 3411, for example, the protrusion 3412 includes one or more vertical protrusions (not shown), e.g., which continuously (or discontinuously) span downward from a top part of the upper segment 3411BU to a bottom part of the upper segment 3411BU, e.g., to the boundary region 3411BB. In some embodiments of the spiked microneedle structure 3411, for example, the protrusion 3412 includes one or more lateral protrusions (not shown), e.g., where a lateral protrusion can span along a circumference of the upper segment 3411BU, and where a plurality of lateral protrusions may be configured as concentric protrusions distributed along the outer wall of the upper segment 3411BU from a top part of the upper segment 3411BU to a bottom part of the upper segment 3411BU, e.g., to the boundary region 3411BB. In some embodiments of the spiked microneedle structure 3411, for example, the tip region 3411T includes a conical shape with the apex 3411A having a dimension (e.g., diameter or length) of 5 µm or less, or of 2 µm or less.

In some embodiments, the spiked microneedle structure 3411 can include a plurality of pores 3411TP (e.g., microscale-sized pores, "micropores", which can be in a range of 0.5 µm to 20 µm, or in a range of 0.5 µm to 10 µm) distributed on the tip region 3411. In some implementations, the pores 3411 are configured to attach one or more chemical compounds to provide the functional layer 116 configured to interact with a target analyte in the biofluid. For example, the pores 3411 can attach the one or more chemical compounds (e.g., reagents) to facilitate an electrochemical reaction involving the target analyte in the biofluid exposed to the spiked microneedle structure 3411 to cause production of an electrical signal detectable at an electrode portion of the spiked microneedle structure 3411 (e.g., the sensor electrode portion including an electrically conductive material at the tip region 3411T or the tip region 3411T and the upper segment 3411BU of the body region 3411B).

In some embodiments, the spiked microneedle structure 3411 can include a plurality of channels 3414 that run between the bottom of the lower segment 3411BL to the boundary region 3411BB, e.g., which can run vertically, slanted, or other. In the example shown in FIG. 34A, the plurality of channels 3414 are configured as vertical channels. In some embodiments of the plurality of channels 3414, for example, the channels are structured to include at least one an inwardly-tapered wall from an outward surface 3414SO of the channels 3414 to a channel basin 3414CB, as exemplified in the cross-sectional inset 3499.

In some implementations of the spiked microneedle structure 3411, the boundary region 3411BB includes a circumferential indention (e.g., having a smaller diameter than the interfacing diameters of the upper segment 3411BU and lower segment 3411BL), which can provide a cut-off line (e.g., cut-off line 421) that provides a location where the autonomous flow of a microfluidic sealant (e.g., polymer resin) stops flowing, allowing the sealant to be cured to form a sealed base 3415 of the spiked microneedle structure 3411. The diagram on the left shows an underlying structure of the example spiked microneedle structures 3411, e.g., prior to the capillary flow of the resin through the microfluidic channels 3414 to be cured to form the sealed base 3415; and the diagram on the right of FIG. 34A shows the example spiked microneedle structure 3411 after formation of the sealed base 3415 on the lower segment 3411BL of the body region 3411B. In various implementations, for example, the microfluidic channels 3414 can be sized to facilitate the control of the capillary flow, e.g., including to a depth, a width, and a spacing of the microfluidic channels 3414. This can also allow the control of the thickness of the sealed base 3415, e.g., which can be varied to different diameters. The location of the cut-off line can control the height of the sealed base 3415 to be configured to different heights.

For example, in implementations, the spiked microneedle structure 3411 can enhance sensing stability and surface area, where the example spiral protrusion 3412 on the body region 3411B (e.g., bare metal portion) can facilitate a pain-free skin insertion of the spiked microneedle array of an example embodiment of the spiked microneedle array sensor device, e.g., with reproducibility. Moreover, for example, the example cut-off line at the boundary region 3411BB can provide reproducible sealing to create the sealed base 3415 facilitated by the example vertical microfluidic channels 3414, for spontaneous sealant suction towards the cut-off line.

Figures 34B, 34C:
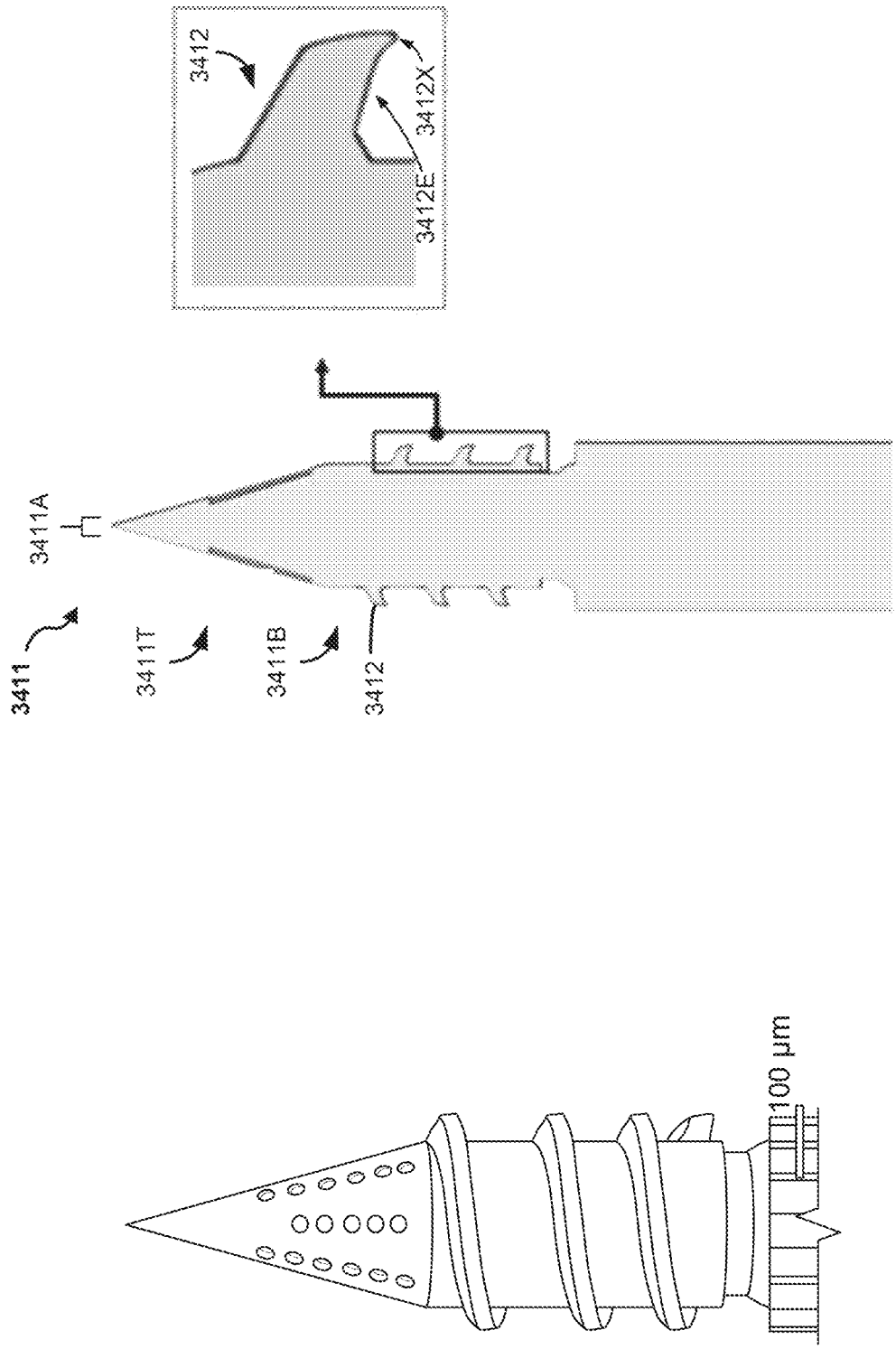
FIG. 34B shows an image of an example single spiked microneedle structure.
FIG. 34C shows a diagram depicting an example embodiment of the spiked microneedle structure in accordance with the embodiments of the spiked microneedle structure shown in FIG. 34A.

FIG. 34B shows an image of an example single spiked microneedle structure in accordance with the embodiments of the spiked microneedle structure 3411 shown in FIG. 34A, depicting a spiral protrusion in the upper segment of the body region, a cut-off line boundary, and a plurality of vertical microfluidic channels in the lower segment of the body region. In the example of FIG. 34B, the spiked microneedle structure includes a 100 μm channel depth for the vertical microfluidic channels.

FIG. 34C shows a diagram depicting an example embodiment of the spiked microneedle structure in accordance with the embodiments of the spiked microneedle structure 3411 shown in FIG. 34A, where the protrusion 3412 of the spiked microneedle structure 3411 includes a terminus portion 3412X directed downward away from the apex 3411A to form an interlocking edge 3412E on the protrusion. In implementations of a microneedle sensor device comprising the example spiked microneedle structure shown in FIG. 34C, the device is capable of reducing noise and thereby enhancing the detectable electrical signal associated with the target analyte in the biofluid to be detected. The example protrusion 3412 shown in FIG. 34C is a spiral protrusion, but it is understood that other embodiments of the protrusion 3412, including a vertical protrusion or a lateral protrusion can be configured to include the terminus portion 3412X directed downward away from the apex 3411A to form the interlocking edge 3412E on the protrusion 3412. For example, the structure of the interlocking edge 3412E with the terminus portion 3412X can support the spiked microneedle structure 3411 while inserted in the skin, which consequently can reduce noise in the detected measurements. Also, for example, the structure of the interlocking edge 3412E with the terminus portion 3412X may facilitate a reduced or pain-free insertion, wearing, and/or removal process.

Figure 34D:
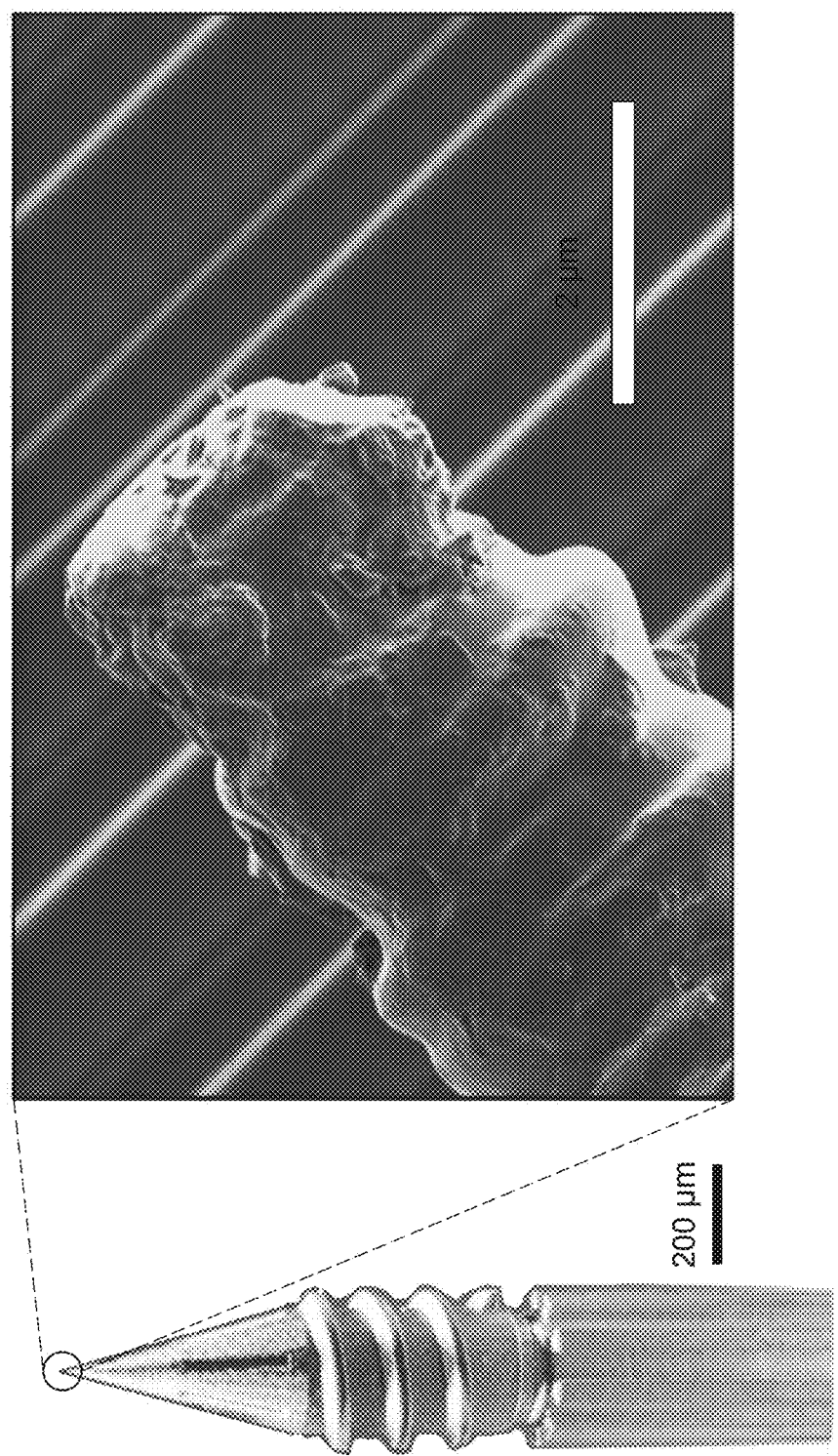
FIG. 34D shows images of an example single spiked microneedle structure in accordance with the embodiments of the spiked microneedle structure shown in FIG. 34A and its tip region, with a SEM inset image depicting the apex of the tip region.

FIG. 34D shows images of an example single spiked microneedle structure in accordance with the embodiments of the spiked microneedle structure 3411 shown in FIG. 34A and its tip region, with a SEM inset image depicting the apex of the tip region having a 2 μm dimension (e.g., diameter of the tip point).

Figure 35A:
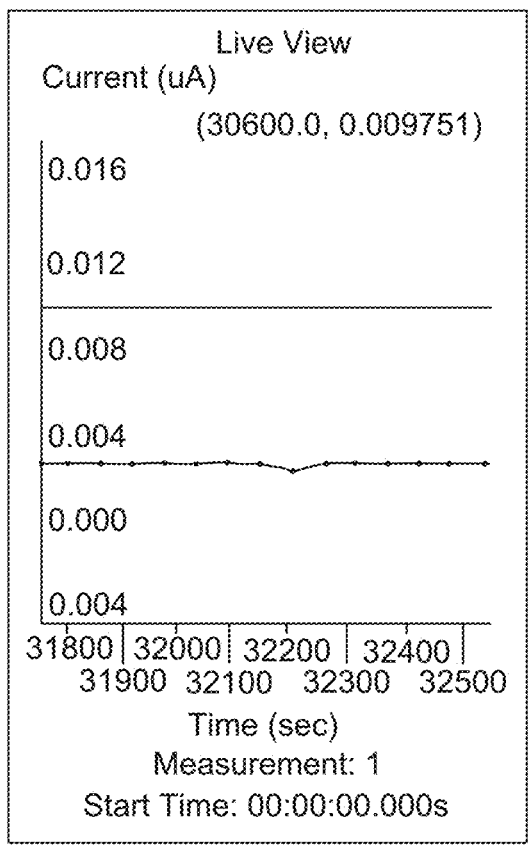
FIGS. 35A and 35B show comparative data plots depicting measured noise from an example embodiment of the spiked microneedle structure comprising the example spiral protrusion and an example spiked microneedle structure array having a flat body region, respectively, that were inserted in the skin of a subject.
Figure 35A:
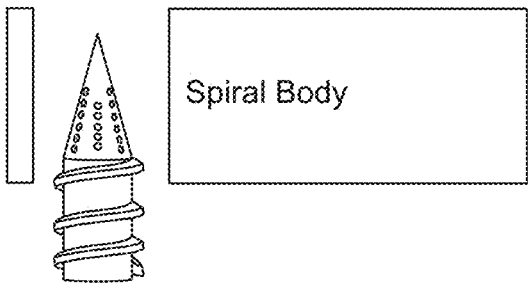
Figure 35B:
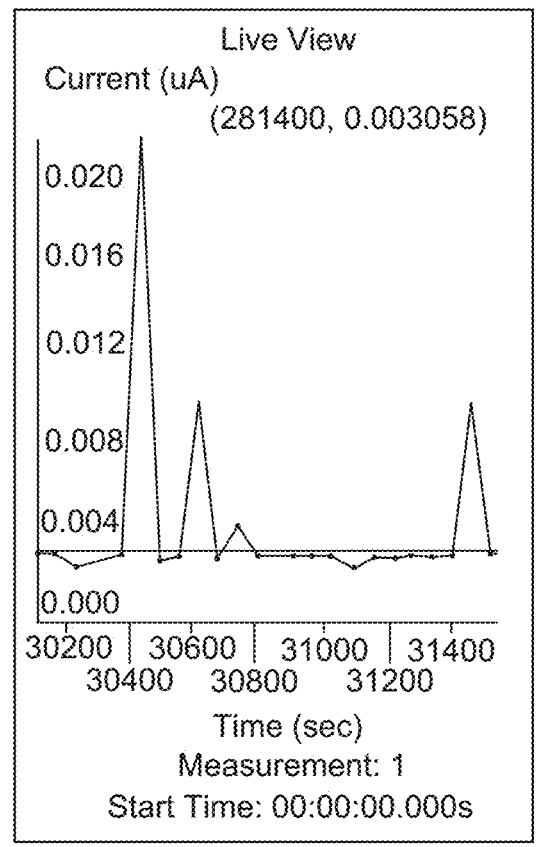
Figure 35B:
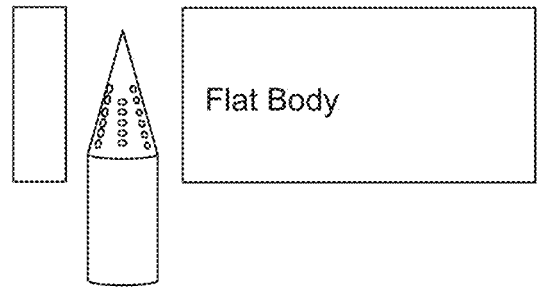

FIGS. 35A and 35B show comparative data plots of current signal versus the time elapsed from the measurement start depicting measured noise from an example embodiment of the spiked microneedle structure 3411 comprising the example spiral protrusion ("spiral body" microneedle) and an example flat-body spiked microneedle structure array ("flat body" microneedle), respectively, that were inserted in the skin of a subject. The data plots depict real-time current signal data in μA (e.g., recorded every 20 seconds) on Y axis versus elapsed time in seconds on X axis, where the spiral body microneedle exhibited no substantial fluctuations due to noise (FIG. 35A), while the flat body microneedle exhibited noise in the nanoscale level, e.g., 2 to 20 nA (FIG. 35B).

Figure 36:
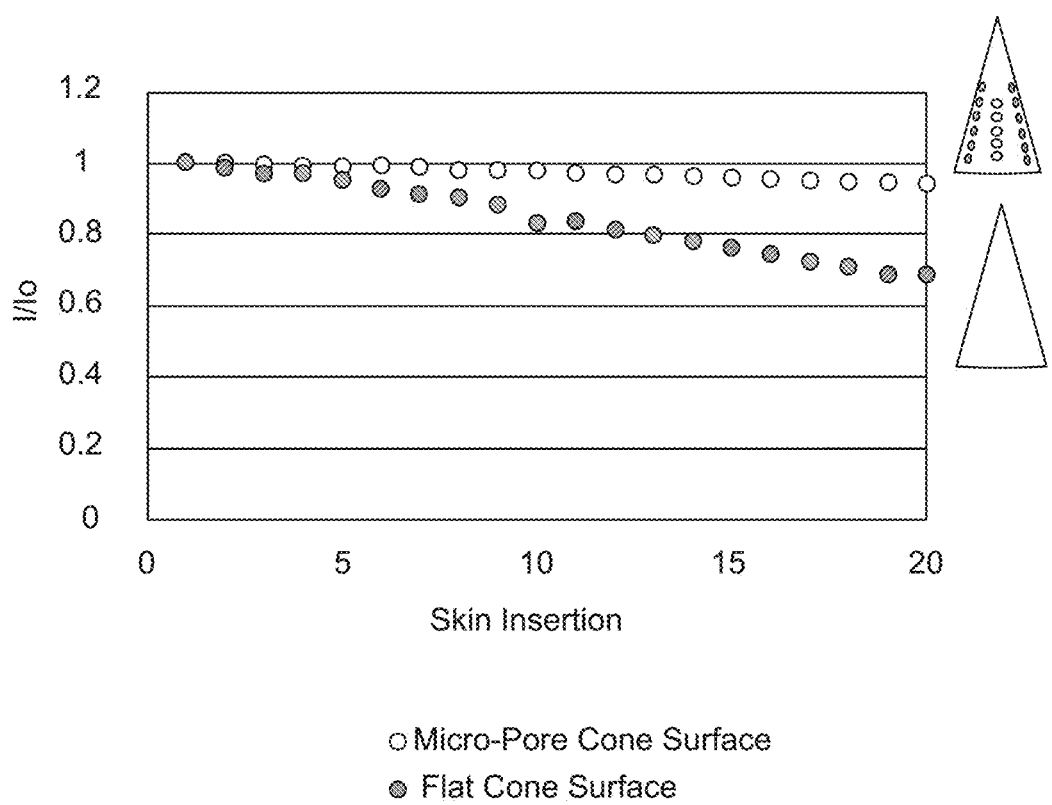
FIG. 36 shows a data plot showing data from a wear-stability study comparing the example spiral body microneedle of FIG. 35A and flat body microneedle of FIG. 35B.

FIG. 36 shows a data plot showing data from a wear-stability study comparing the example spiral body microneedle of FIG. 35A and flat body microneedle of FIG. 35B. In this study, the spiked microneedle array was inserted repeatedly into the skin of a human subject and after each insertion, the electrochemical current signal was measured resulted from a 500 μM change in concentration of hydrogen peroxide solution. The numbers in y-axis show the normalized current signals against the initial signal, $I_o$, while the numbers on x-axis show the skin insertion times.

Figure 37:
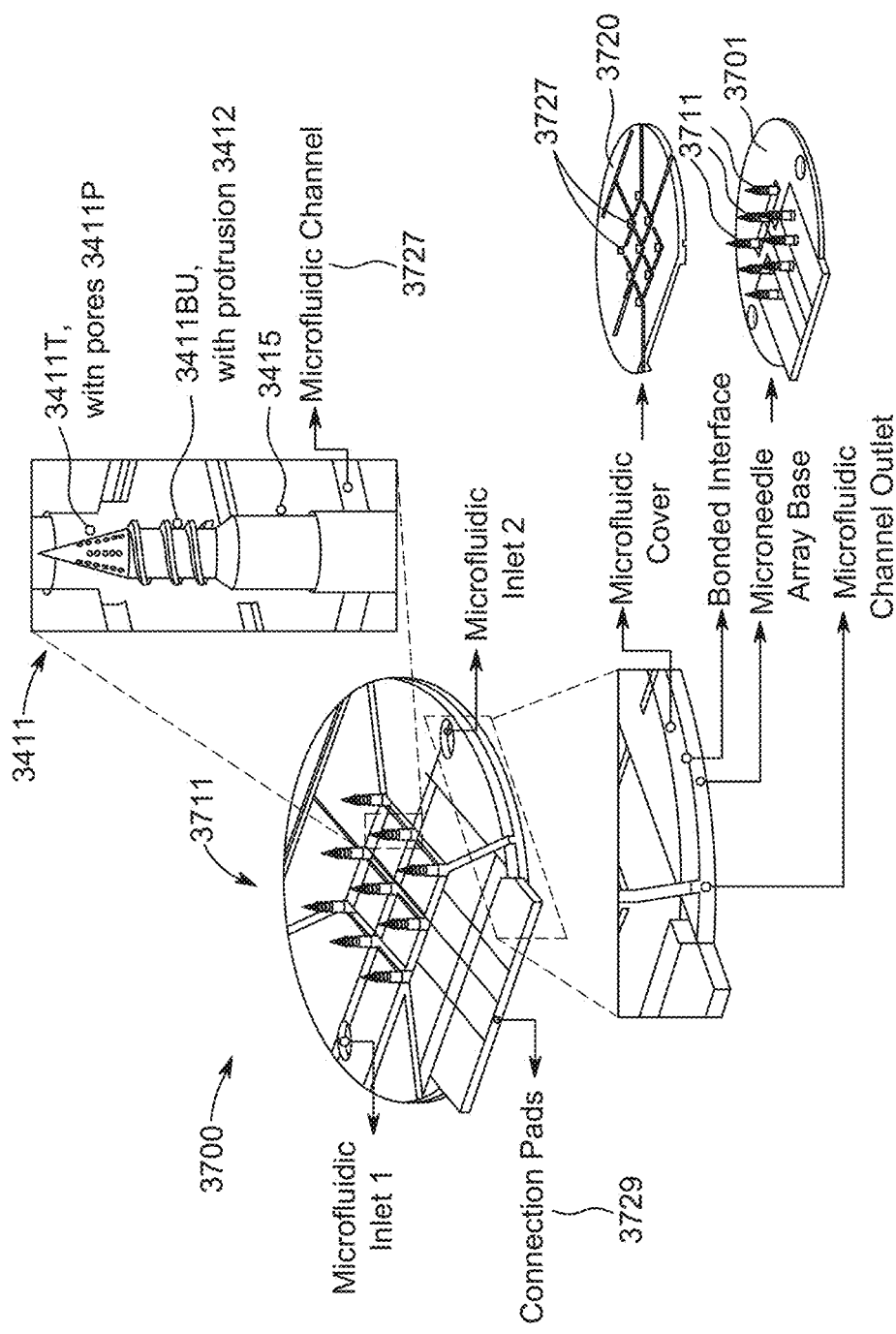
FIG. 37 shows a schematic diagram depicting various structural aspects of an example embodiment of a spiked microneedle sensor unit in accordance with the present technology.

FIG. 37 shows a schematic diagram depicting various structural aspects of an example embodiment of a spiked microneedle sensor unit, labeled 3700, in accordance with the spiked microneedle sensor unit 110. The spiked microneedle sensor unit 3700 includes an array of spiked microneedle structures 3711, which can include the spiked microneedle structure 3411 shown in FIGS. 34A-34C or other embodiments of spiked microneedle structures disclosed herein, which is disposed on a substrate 3701. On the upper-right side of FIG. 37, a diagram shows an example embodiment of the spiked microneedle structure 3411 with the insulated sealed base 3415 and network of microfluidic channels 3727 that are structured within a microfluidic cover structure 3720, within which a sealant/insulator material can flow through to create the sealed base structure 3715. The diagram of FIG. 37 shows an example 3×3 array of spiked microneedle structures 3711 on the substrate 3701 and electrical interconnections (e.g., electrically conductive traces, wires) disposed on the substrate 3701 spanning between individual spiked microneedle structures 3711 and electrically conductive terminuses or connection pads 3729. Notably, in this example, the microfluidic cover structure 3720 includes at least one microfluidic inlet and at least one microfluidic outlet that interfaces with the microfluidic channels 3727, e.g., to allow microfluidic transfer of a resin material, to form the sealed base 3415, for example, with reproducibly defined sensing tip containing the exposed metal. In this example design of the cover/spiked microneedle array component, the spontaneous capillary force-driven flow of the photocurable resin takes place upon immersing of the bonded piece on a thin layer of photocurable resin through the microfluidic inlets 1 and 2 to the microfluidic channels 3727 in between the two pieces (i.e., the microfluidic cover and the microneedle array base), through the microneedle bodily channels (e.g., example vertical, slanted, upward microfluidic channels 3414 along the lower segment 3411BL of the body region), and up to the cut-off line positioned at the boundary region 3411BB.

EXAMPLES

In some example embodiments in accordance with the present technology (example A1), a wearable, non-intrusive microneedle sensor device includes a microneedle sensor unit and an electronics unit. The microneedle sensor unit includes a substrate comprising an electrically insulative material, an array of spiked microneedle structures disposed on the substrate, wherein at least some of the spiked microneedle structures are configured as electrochemical sensor electrodes to detect an electrical signal from a reaction with a target analyte in a biofluid exposed to the array of spiked microneedle structures, wherein at least one electrochemical sensor electrode is functionalized by a chemical layer to interact with the target analyte in the biofluid and produce the electrical signal at the at least one electrochemical sensor electrode, and wherein each spiked microneedle structure of the array of spiked microneedle structures includes a body region and a tip region, the body region including a cylindrical shape having a spiral protrusion that winds around at least a portion of the body region, and the tip region including a conical shape, an array of base structures comprising an electrical insulator material, wherein each base structure encases a lower portion of the body region of a corresponding spiked microneedle structure, and a plurality of electrical interconnections disposed in or on the substrate, wherein each of the electrical interconnections is coupled to one or more of the spiked microneedle structures configured as the electrochemical sensor electrodes and to a contact terminus structure on the substrate. The electronics unit is in electrical communication with the plurality of electrical interconnections of the microneedle sensor unit, the electronics unit comprising a circuit board, a signal processing circuit configured on the circuit board, a power source in electrical communication with the signal processing circuit, and a plurality of rigid conductive pins that electrically couple the microneedle sensor unit to the electronics unit by allowing contact between an elongated region of a rigid conductive pin to the terminus region of a corresponding electrical interconnection.

Example A2 includes the device of any of examples A1-A24, wherein the microneedle sensor unit further comprises a cover unit to couple with the substrate, the cover unit comprising a sensor-cover component formed of an electrically insulative material having an array of openings configured to align with the array of spiked microneedle structures on the substrate, such that the tip region and at least a distal portion of the body region of the spiked microneedles pass through the array of openings of the sensor-cover component of the cover unit, wherein the sensor-cover component is configured to protect the microneedle sensor unit's underlying structures from undesired substances contaminating the device.

Example A3 includes the device of example A2 or any of examples A1-A24, wherein the microneedle sensor unit and the cover unit are configured to be disposable after at least a first use by a user of the wearable, non-intrusive microneedle sensor device used to continuously monitor the target analyte, and wherein the electronics unit is configured to be reusable after at least the first use.

Example A4 includes the device of example A2 or any of examples A1-A24, wherein the sensor-cover component of the cover unit includes a sidewall that surrounds an interior region and is configured to encompass a side of the substrate when the cover unit is coupled with the substrate, and the cover unit includes a back-cover component that is configured to connect with the sidewall of the sensor-cover component and contact a backside of the substrate.

Example A5 includes the device of example A4 or any of examples A1-A24, wherein the cover unit further includes a holder having a peripheral sidewall that couples to the sidewall of the cover unit, the holder having an opening such that, when the holder is coupled to the sidewall of the microneedle sensor unit, the array of spiked microneedle structures expand outward beyond the opening.

Example A6 includes the device of example A5 or any of examples A1-A24, further comprising: an outer casing configured to connect to the holder of the cover unit and encase the electronics unit and the microneedle sensor unit while exposing the array of spiked microneedle structures from beyond the opening of the holder.

Example A7 includes the device of any of examples A1-A24, wherein each spiked microneedle structure includes an electrically insulative core that is at least partially coated by an electrically conductive layer that continuously covers at least an apex of the tip region to the lower portion of the body region, such that the electrically conductive layer of the spiked microneedle structure contacts the corresponding electrical interconnection.

Example A8 includes the device of example A7 or any of examples A1-A24, wherein the electrically insulative core includes PMMA.

Example A9 includes the device of example A7 or any of examples A1-A24, wherein the electrically conductive layer includes platinum, gold, silver, chromium, carbon, or other conductive metal or alloy, or a combination thereof.

Example A10 includes the device of any of examples A1-A24, wherein the tip region of at least some of the spiked microneedle structures of the array have an angle at an apex of the tip region in a range of 40° to 85°.

Example A11 includes the device of any of examples A1-A24, wherein at least some of the spiked microneedle structures have a height-to-thickness aspect ratio in a range of 4:1 to 20:1.

Example A12 includes the device of any of examples A1-A24, wherein the substrate of the microneedle sensor unit comprises a plurality of channels disposed within or on a surface of the substrate, and wherein at least some of the plurality of channels are at least partially filled by the plurality of electrical interconnections.

Example A13 includes the device of example A12 or any of examples A1-A24, wherein the array of spiked microneedle structures is arranged into two or more subgroups of spiked microneedle structures from the array, wherein a first subgroup of spiked microneedle structures include a first chemical layer to interact with a first target analyte in the biofluid, and wherein a second subgroup of spiked microneedle structures include a second chemical layer to interact with a second target analyte in the biofluid, and wherein the plurality of channels is configured to provide a first subgroup of electrical interconnections to the first subgroup of spiked microneedle structures and a second subgroup of electrical interconnections to the second subgroup of spiked microneedle structures.

Example A14 includes the device of example A13 or any of examples A1-A24, wherein the first target analyte includes one or both of glucose and lactate, and wherein the second target analyte includes one or both of glucose and alcohol.

Example A15 includes the device of any of examples A1-A24, wherein the contact terminus structure that couples to a respective electrical interconnection is structured within a hole in the substrate that includes an electrically-conductive and mechanically frictionous contact pad, such that the elongated region of a rigid conductive pin from the electronics unit is in contact with the electrically-conductive and mechanically frictionous contact pad of the terminus region of a corresponding electrical interconnection.

Example A16 includes the device of any of examples A1-A24, wherein the electronics unit further comprises a data processing unit in communication with the signal conditioning unit, the data processing unit comprising a processor and a memory and configured to process the electrical signal as data representative of one or more parameters of the target analyte.

Example A17 includes the device of example A16 or any of examples A1-A24, wherein the signal conditioning unit is configured to process the electrical signal by one or more of amplifying the electrical signal, filtering the electrical signal, or converting the electrical signal from analog to digital, and wherein the data processing unit is configured to process the electrical signal after processing by the signal conditioning unit.

Example A18 includes the device of example A16 or any of examples A1-A24, wherein the electronics unit further comprises a wireless communication unit in communication with one or both of the signal conditioning unit and the data processing unit, the wireless communication unit comprising a wireless transmitter or wireless transceiver to at least transmit one or both of the electrical signal and the data to an external computing device.

Example A19 includes the device of any of examples A1-A24, wherein the target analyte includes one or more of a metabolite, ionophore, electrolyte, protein, amino acid, nucleic acid, lipid, liposome, nanoparticle, or drug including a therapeutic drug, licit drug, or illicit drug.

Example A20 includes the device of example A19 or any of examples A1-A24, wherein the target analyte includes a protein comprising one or more of an enzyme, peptide-based aptamer, antibody, or hormone.

Example A21 includes the device of example A19 or any of examples A1-A24, wherein the target analyte includes a nucleic acid comprising one or more of a nucleotide, oligonucleotide, oligonucleotide-based aptamer, deoxyribonucleic acid (DNA) or portion thereof, or ribonucleic acid (RNA) or portion thereof.

Example A22 includes the device of any of examples A1-A24, wherein at least one of the spiked microstructures includes a biological or chemical recognition element comprising one or more of an enzyme, an ionophore, an antibody, a peptide nucleic acid (PNA), a DNA aptamer, a RNA aptamer, or a cell.

Example A23 includes the device of any of examples A1-A24, wherein the device is configured to measure the target analyte in the biofluid, comprising any of a subdermal biological fluid.

Example A24 includes the device of example A23 or any of examples A1-A22, wherein the subdermal biological fluid comprises an interstitial fluid, an extracellular fluid, a cerebrospinal fluid, or blood.

In some example embodiments in accordance with the present technology (example B1), a wearable, non-intrusive microneedle sensor device includes a microneedle sensor unit and an electronics unit in electrical communication with the microneedle sensor unit. The microneedle sensor unit comprises (i) a substrate comprising an electrically insulative material, (ii) an array of spiked microneedle structures disposed on the substrate, wherein at least some of the spiked microneedle structures are configured as electrochemical sensor electrodes to detect an electrical signal from a reaction with a target analyte in a biofluid exposed to the array of spiked microneedle structures, wherein at least one electrochemical sensor electrode is functionalized by a chemical layer to interact with the target analyte in the biofluid and produce the electrical signal at the at least one electrochemical sensor electrode, and wherein each spiked microneedle structure of the array of spiked microneedle structures includes a body region and a tip region, the body region including a cylindrical shape having a spiral protrusion that winds around at least a portion of the body region, and the tip region including a conical shape, (iii) an array of base structures comprising an electrical insulator material, wherein each base structure encases a lower portion of the body region of a corresponding spiked microneedle structure, and (iv) a plurality of electrical interconnections disposed in or on the substrate, wherein each of the electrical interconnections is coupled to one or more of the spiked microneedle structures configured as the electrochemical sensor electrodes and to a contact terminus structure on the substrate. The electronics unit is in electrical communication with the plurality of electrical interconnections, and the electronics unit comprises a circuit board, a signal processing circuit configured on the circuit board, a power source in electrical communication with the signal processing circuit, and a plurality of conductive pins that electrically couple the microneedle sensor unit to the electronics unit by allowing contact between an elongated region of a conductive pin to the terminus region of a corresponding electrical interconnection.

Example B2 includes the device of any of examples B1-B33, wherein the microneedle sensor unit further comprises a cover unit to couple with the substrate, the cover unit comprising a sensor-cover component formed of an electrically insulative material having an array of openings configured to align with the array of spiked microneedle structures on the substrate, such that the tip region and at least a distal portion of the body region of the spiked microneedles pass through the array of openings of the sensor-cover component of the cover unit, wherein the sensor-cover component is configured to protect the microneedle sensor unit's underlying structures from undesired substances contaminating the device.

Example B3 includes the device of example B2 or any of examples B1-B33, wherein the microneedle sensor unit and the cover unit are configured to be disposable after at least a first use by a user of the wearable, non-intrusive microneedle sensor device used to continuously monitor the target analyte, and wherein the electronics unit is configured to be reusable after at least the first use.

Example B4 includes the device of example B2 or any of examples B1-B33, wherein the cover unit includes openings configured to feed a curable polymer resin to microfluidic channels disposed underneath or on a surface of the substrate to be photo-crosslinked in order to form the array of base structures comprising the electrical insulator material, which is operable to electrically insulate the substrate base and a portion of the spiked microneedle structures to a specific height.

Example B5 includes the device of example B2 or any of examples B1-B33, wherein the sensor-cover component of the cover unit includes a sidewall that surrounds an interior region and is configured to encompass a side of the substrate when the cover unit is coupled with the substrate, and the cover unit includes a back-cover component that is configured to connect with the sidewall of the sensor-cover component and contact a backside of the substrate.

Example B6 includes the device of example B5 or any of examples B1-B33, wherein the cover unit further includes a holder having a peripheral sidewall that couples to the sidewall of the cover unit, the holder having an opening such that, when the holder is coupled to the sidewall of the microneedle sensor unit, the array of spiked microneedle structures expand outward beyond the opening.

Example B7 includes the device of example B6 or any of examples B1-B33, further comprising an outer casing configured to connect to the holder of the cover unit and encase the electronics unit and the microneedle sensor unit while exposing the array of spiked microneedle structures from beyond the opening of the holder.

Example B8 includes the device of any of examples B1-B33, wherein each spiked microneedle structure includes an electrically insulative core that is at least partially coated by an electrically conductive layer that continuously covers at least an apex of the tip region to the lower portion of the body region, such that the electrically conductive layer of the spiked microneedle structure contacts the corresponding electrical interconnection.

Example B9 includes the device of example B8 or any of examples B1-B33, wherein the electrically insulative core includes PMMA.

Example B10 includes the device of example B8 or any of examples B1-B33, wherein the electrically conductive layer includes platinum, gold, silver, chromium, carbon or other conductive metal or alloy, or a combination thereof.

Example B11 includes the device of any of examples B1-B33, wherein the spiral protrusion includes a spiral angle of at least 20°, and/or wherein the spiral protrusion includes a height protruding from the body region of at least 25 μm.

Example B12 includes the device of any of examples B1-B33, wherein the spiral protrusion includes an outward terminus portion directed downward to form an interlocking edge on the protrusion spiral.

Example B13 includes the device of any of examples B1-B33, wherein the tip region of at least some of the spiked microneedle structures of the array have an angle at an apex of the tip region in a range of 40° to 85°.

Example B14 includes the device of any of examples B1-B33, wherein the tip region includes a conical shape with an apex with a dimension of 5 μm or less, or wherein the tip region includes a conical shape with an apex with a dimension of 2 μm or less.

Example B15 includes the device of any of examples B1-B33, wherein the tip region includes a plurality of pores, and wherein the plurality of pores of the tip region is configured on the at least one electrochemical sensor electrode to anchor one or more chemical compounds to create the chemical layer configured to interact with the target analyte in the biofluid.

Example B16 includes the device of any of examples B1-B33, wherein the body region includes a plurality of channels that run in a lower portion of the body region to a boundary between the lower portion and the upper portion of the body region.

Example B17 includes the device of example B16 or any of examples B1-B33, wherein the plurality of channels of the body region includes at least one of vertical channels or slanted channels.

Example B18 includes the device of example B16 or any of examples B1-B33, wherein the plurality of channels of the body region is configured to flow a curable polymer resin from one or more microfluidic channels on or in the substrate that is operable to be photo-crosslinked when the curable polymer resin is in the plurality of channels to form an electrical insulating material and create an array of base structures that encases the lower portion of the body region of a corresponding microneedle structure.

Example B19 includes the device of any of examples B1-B33, wherein at least some of the spiked microneedle structures have a height-to-thickness aspect ratio in a range of 4:1 to 20:1.

Example B20 includes the device of any of examples B1-B33, wherein the substrate of the microneedle sensor unit comprises a plurality of channels disposed within or on a surface of the substrate, and wherein at least some of the plurality of channels are at least partially filled by the plurality of electrical interconnections.

Example B21 includes the device of example B20 or any of examples B1-B33, wherein the array of spiked microneedle structures is arranged into two or more subgroups of spiked microneedle structures from the array, wherein a first subgroup of spiked microneedle structures include a first chemical layer to interact with a first target analyte in the biofluid, and wherein a second subgroup of spiked microneedle structures include a second chemical layer to interact with a second target analyte in the biofluid, and wherein the plurality of channels is configured to provide a first subgroup of electrical interconnections to the first subgroup of spiked microneedle structures and a second subgroup of electrical interconnections to the second subgroup of spiked microneedle structures.

Example B22 includes the device of example B21 or any of examples B1-B33, wherein the first target analyte is different than the second target analyte, and wherein the first target analyte and the second target analyte include at least one of glucose, ketone bodies, lactate, a salt ion, or alcohol.

Example B23 includes the device of any of examples B1-B33, wherein the contact terminus structure that couples to a respective electrical interconnection is structured within a hole in the substrate that includes an electrically-conductive and mechanically frictionous contact pad, such that the elongated region of a conductive pin from the electronics unit is in contact with the electrically-conductive and mechanically frictionous contact pad of the terminus region of a corresponding electrical interconnection.

Example B24 includes the device of any of examples B1-B33, wherein at least one conductive pin of the plurality of conductive pins includes a rigid metallic conductive pin, or at least one conductive pin of the plurality of conductive pins includes a flexible polymer-based conductive pin, or at least one conductive pin of the plurality of conductive pins includes a rigid metallic conductive pin and at least another conductive pin of the plurality of conductive pins includes a flexible polymer-based conductive pin.

Example B25 includes the device of any of examples B1-B33, wherein the electronics unit further comprises a data processing unit in communication with the signal conditioning unit, the data processing unit comprising a processor and a memory and configured to process the electrical signal as data representative of one or more parameters of the target analyte.

Example B26 includes the device of example B25 or any of examples B1-B33, wherein the signal conditioning unit is configured to process the electrical signal by one or more of amplifying the electrical signal, filtering the electrical signal, or converting the electrical signal from analog to digital, and wherein the data processing unit is configured to process the electrical signal after processing by the signal conditioning unit.

Example B27 includes the device of example B25 or any of examples B1-B33, wherein the electronics unit further comprises a wireless communication unit in communication with one or both of the signal conditioning unit and the data processing unit, the wireless communication unit comprising a wireless transmitter or wireless transceiver to at least transmit one or both of the electrical signal and the data to an external computing device.

Example B28 includes the device of any of examples B1-B33, wherein the target analyte includes one or more of a metabolite, electrolyte, protein, amino acid, nucleic acid, lipid, liposome, nanoparticle, or drug.

Example B29 includes the device of example B28 or any of examples B1-B33, wherein the target analyte includes the protein, comprising one or more of an enzyme, peptide-based aptamer, antibody, or hormone.

Example B30 includes the device of example B28 or any of examples B1-B33, wherein the target analyte includes the nucleic acid, comprising one or more of a nucleotide, oligonucleotide, oligonucleotide-based aptamer, deoxyribonucleic acid (DNA) or portion thereof, or ribonucleic acid (RNA) or portion thereof.

Example B31 includes the device of any of examples B1-B33, wherein at least one of the spiked microstructures includes a biological or chemical recognition element comprising one or more of an enzyme, an ionophore, an antibody, a peptide nucleic acid (PNA), a DNA aptamer, a RNA aptamer, or a cell.

Example B32 includes the device of any of examples B1-B33, wherein the device is configured to measure the target analyte in the biofluid, comprising any of a subdermal biological fluid.

Example B33 includes the device of example B32 or any of examples B1-B31, wherein the subdermal biological fluid comprises an interstitial fluid, an extracellular fluid, a cerebrospinal fluid, or blood.

In some example embodiments in accordance with the present technology (example B34), a wearable, non-intrusive microneedle sensor device includes a microneedle sensor unit and an electronics unit in electrical communication with the microneedle sensor unit. The microneedle sensor unit comprises (i) a substrate comprising an electrically insulative material, and (ii) an array of microneedle structures disposed on the substrate and comprising a body region and a tip region, wherein the body region includes a protrusion that winds around at least an upper portion of the body region, wherein at least some of the microneedle structures are configured as electrochemical sensor electrodes to detect an electrical signal from a reaction with a target analyte in a biofluid exposed to the array of microneedle structures, wherein at least one electrochemical sensor electrode is functionalized by a chemical layer to interact with the target analyte in the biofluid and produce the electrical signal at the at least one electrochemical sensor electrode. The electronics unit is in electrical communication with the microneedle sensor unit, and the electronics unit comprises a circuit board, and a plurality of conductive pins that electrically couple the microneedle sensor unit to the circuit board of the electronics unit by allowing contact between an elongated region of a conductive pin to an electrically conductive portion of the microneedle sensor unit.

Example B35 includes the device of any of examples B34-B60, wherein the protrusion that winds around the at least an upper portion of the body region of the microneedle structures includes a spiral protrusion.

Example B36 includes the device of example B35 or any of examples B34-B60, wherein the spiral protrusion includes a spiral angle of at least 20°, and/or wherein the spiral protrusion includes a height protruding from the body region of at least 25 µm.

Example B37 includes the device of any of examples B34-B36 or any of examples B33-B60, wherein the protrusion includes an outward terminus portion directed downward to form an interlocking edge on the protrusion.

Example B38 includes the device of any of examples B34-B60, wherein the tip region includes a conical shape with an apex with a dimension of 5 µm or less, or wherein the tip region includes a conical shape with an apex with a dimension of 2 µm or less.

Example B39 includes the device of any of examples B34-B60, wherein the tip region includes a plurality of pores.

Example B40 includes the device of example B39 or any of examples B34-B60, wherein the plurality of pores of the tip region is configured on the at least one electrochemical sensor electrode to anchor one or more chemical compounds to create the chemical layer configured to interact with the target analyte in the biofluid.

Example B41 includes the device of any of examples B34-B60, wherein the body region includes a plurality of channels that run in a lower portion of the body region to a boundary between the lower portion and the upper portion of the body region.

Example B42 includes the device of example B41 or any of examples B34-B60, wherein the plurality of channels of the body region includes vertical channels.

Example B43 includes the device of example B41 or any of examples B34-B60, wherein the plurality of channels of the body region is configured to flow a curable polymer resin from one or more microfluidic channels on or in the substrate that is operable to be photo-crosslinked when the curable polymer resin is in the plurality of channels to form an electrical insulating material and create an array of base structures that encases the lower portion of the body region of a corresponding microneedle structure.

Example B44 includes the device of any of examples B34-B60, wherein the body region includes a cylindrical shape having at least two segments, wherein a lower segment of the body region of the microneedle structures is encased by an electrically-insulative base structure and comprises a plurality of vertically aligned microfluidic channels, and wherein an upper segment of the body region of the microneedle structures includes the upper portion of the body region where the protrusion is disposed.

Example B45 includes the device of any of examples B34-B60, wherein the array of microneedle structures includes an array of base structures comprising an electrical insulator material, wherein each base structure encases a lower portion of the body region of a corresponding microneedle structure.

Example B46 includes the device of any of examples B34-B60, wherein the microneedle sensor unit comprises a plurality of contact terminus structures on the substrate, and a plurality of electrical interconnections disposed in or on the substrate, wherein each of the electrical interconnections is coupled to one or more of the microneedle structures configured as the electrochemical sensor electrodes and to at least one contact terminus structure of the plurality of contact terminus structures.

Example B47 includes the device of example B46 or any of examples B34-B60, wherein each microneedle structure includes an electrically insulative core that is at least partially coated by an electrically conductive layer that continuously covers at least an apex of the tip region to a lower portion of the body region, wherein that the electrically conductive layer of the microneedle structure contacts a corresponding electrical interconnection of the plurality of electrical interconnections.

Example B48 includes the device of any of examples B34-B60, wherein the microneedle sensor unit further comprises a cover unit to couple with the substrate, the cover unit comprising a sensor-cover component formed of an electrically insulative material having an array of openings configured to align with the array of microneedle structures on the substrate, such that the tip region and at least a distal portion of the body region of the microneedles pass through the array of openings of the sensor-cover component of the cover unit.

Example B49 includes the device of example B48 or any of examples B34-B60, wherein the microneedle sensor unit and the cover unit are configured to be disposable after at least a first use by a user of the wearable, non-intrusive microneedle sensor device used to continuously monitor the target analyte, and wherein the electronics unit is configured to be reusable after at least the first use.

Example B50 includes the device of example B48 or any of examples B34-B60, wherein the sensor-cover component of the cover unit includes a sidewall that surrounds an interior region and is configured to encompass a side of the substrate when the cover unit is coupled with the substrate, and the cover unit includes a back-cover component that is configured to connect with the sidewall of the sensor-cover component and contact a backside of the substrate.

Example B51 includes the device of example B50 or any of examples B34-B60, wherein the cover unit further includes a holder having a peripheral sidewall that couples to the sidewall of the cover unit, the holder having an opening such that, when the holder is coupled to the sidewall of the microneedle sensor unit, the array of microneedle structures expand outward beyond the opening.

Example B52 includes the device of example B51 or any of examples B34-B60, further comprising an outer casing configured to connect to the holder of the cover unit and encase the electronics unit and the microneedle sensor unit while exposing the array of microneedle structures from beyond the opening of the holder.

Example B53 includes the device of any of examples B34-B60, wherein the array of microneedle structures is arranged into two or more subgroups of microneedle structures from the array, wherein a first subgroup of microneedle structures include a first chemical layer to interact with a first target analyte in the biofluid, and wherein a second subgroup of microneedle structures include a second chemical layer to interact with a second target analyte in the biofluid.

Example B54 includes the device of any of examples B34-B60, wherein the microneedle sensor unit includes a plurality of contact terminus structures that couple to the plurality of electrical interconnections, where each of the plurality of contact terminus structures is structured within a hole in the substrate that includes an electrically-conductive and mechanically frictionous contact pad, such that an elongated region of a conductive pin of the plurality of conductive pins from the electronics unit is in contact with the electrically-conductive and mechanically frictionous contact pad of the contact terminus region of a corresponding electrical interconnection.

Example B55 includes the device of any of examples B34-B60, wherein at least one conductive pin of the plurality of conductive pins includes a rigid metallic conductive pin, or at least one conductive pin of the plurality of conductive pins includes a flexible polymer-based conductive pin, or at least one conductive pin of the plurality of conductive pins includes a rigid metallic conductive pin and at least another conductive pin of the plurality of conductive pins includes a flexible polymer-based conductive pin.

Example B56 includes the device of any of examples B34-B60, wherein the electronics unit further comprises a signal conditioning unit and a data processing unit in communication with the signal conditioning unit, the data processing unit comprising a processor and a memory and configured to process the electrical signal as data representative of one or more parameters of the target analyte.

Example B57 includes the device of example B56 or any of examples B34-B60, wherein the signal conditioning unit is configured to process the electrical signal by one or more of amplifying the electrical signal, filtering the electrical signal, or converting the electrical signal from analog to digital, and wherein the data processing unit is configured to process the electrical signal after processing by the signal conditioning unit.

Example B58 includes the device of example B57 or any of examples B34-B60, wherein the electronics unit further comprises a wireless communication unit in communication with one or both of the signal conditioning unit and the data processing unit, the wireless communication unit comprising a wireless transmitter or wireless transceiver to at least transmit one or both of the electrical signal and the data to an external computing device.

Example B59 includes the device of any of examples B34-B60, wherein the target analyte includes one or more of a metabolite, electrolyte, protein, amino acid, nucleic acid, lipid, liposome, nanoparticle, or drug, and wherein at least one of the spiked microstructures includes a biological or chemical recognition element comprising one or more of an enzyme, an ionophore, an antibody, a peptide nucleic acid (PNA), a DNA aptamer, a RNA aptamer, or a cell.

Example B60 includes the device of any of examples B34-B59, wherein the device is configured to measure the target analyte in the biofluid, comprising any of a subdermal biological fluid that comprises an interstitial fluid, an extracellular fluid, a cerebrospinal fluid, or blood.

In some example embodiments in accordance with the present technology (example B61), a wearable, non-intrusive microneedle sensor patch device includes a substrate comprising an electrically insulative material, and an array of microneedle structures disposed on the substrate and comprising a body region and a tip region, wherein the body region includes a protrusion that winds around at least an upper portion of the body region, wherein at least some of the microneedle structures are configured as electrochemical sensor electrodes to detect an electrical signal from a reaction with a target analyte in a biofluid exposed to the array of microneedle structures, wherein at least one electrochemical sensor electrode is functionalized by a chemical layer to interact with the target analyte in the biofluid and produce the electrical signal at the at least one electrochemical sensor electrode.

Example B62 includes the device of any of examples B61-B82, wherein the protrusion that winds around the at least an upper portion of the body region of the microneedle structures includes a spiral protrusion.

Example B63 includes the device of example B62 or any of examples B61-B82, wherein the spiral protrusion includes a spiral angle of at least 20°, and/or wherein the spiral protrusion includes a height protruding from the body region of at least 25 μm.

Example B64 includes the device of any of examples B61-B63 or any of examples B61-B82, wherein the protrusion includes an outward terminus portion directed downward to form an interlocking edge on the protrusion.

Example B65 includes the device of any of examples B61-B82, wherein the tip region includes a conical shape with an apex with a dimension of 5 μm or less, or wherein the tip region includes a conical shape with an apex with a dimension of 2 μm or less.

Example B66 includes the device of any of examples B61-B82, wherein the tip region includes a plurality of pores.

Example B67 includes the device of example B66 or any of examples B61-B82, wherein the plurality of pores of the tip region is configured on the at least one electrochemical sensor electrode to anchor one or more chemical compounds to create the chemical layer configured to interact with the target analyte in the biofluid.

Example B68 includes the device of any of examples B61-B82, wherein the body region includes a plurality of channels that run in a lower portion of the body region to a boundary between the lower portion and the upper portion of the body region.

Example B69 includes the device of example B68 or any of examples B61-B82, wherein the plurality of channels of the body region includes vertical channels.

Example B70 includes the device of example B68 or any of examples B61-B82, wherein the plurality of channels of the body region is configured to flow a curable polymer resin from one or more microfluidic channels on or in the substrate that is operable to be photo-crosslinked when the curable polymer resin is in the plurality of channels to form an electrical insulating material and create an array of base structures that encases the lower portion of the body region of a corresponding microneedle structure.

Example B71 includes the device of any of examples B61-B82, wherein the body region includes a cylindrical shape having at least two segments, wherein a lower segment of the body region of the microneedle structures is encased by an electrically-insulative base structure and comprises a plurality of vertically aligned microfluidic channels, and wherein an upper segment of the body region of the microneedle structures includes the upper portion of the body region where the protrusion is disposed.

Example B72 includes the device of any of examples B61-B82, wherein the array of microneedle structures includes an array of base structures comprising an electrical insulator material, wherein each base structure encases a lower portion of the body region of a corresponding microneedle structure.

Example B73 includes the device of any of examples B61-B82, further comprising a plurality of contact terminus structures on the substrate, and a plurality of electrical interconnections disposed in or on the substrate, wherein each of the electrical interconnections is coupled to one or more of the microneedle structures configured as the electrochemical sensor electrodes and to at least one contact terminus structure of the plurality of contact terminus structures.

Example B74 includes the device of example B73 or any of examples B61-B82, wherein each microneedle structure includes an electrically insulative core that is at least partially coated by an electrically conductive layer that continuously covers at least an apex of the tip region to a lower portion of the body region, wherein that the electrically conductive layer of the microneedle structure contacts a corresponding electrical interconnection of the plurality of electrical interconnections.

Example B75 includes the device of any of examples B61-B82, wherein the array of microneedle structures is arranged into two or more subgroups of microneedle structures from the array, wherein a first subgroup of microneedle structures include a first chemical layer to interact with a first target analyte in the biofluid, and wherein a second subgroup of microneedle structures include a second chemical layer to interact with a second target analyte in the biofluid.

Example B76 includes the device of any of examples B61-B82, further comprising a cover unit to couple with the substrate, the cover unit comprising a sensor-cover component formed of an electrically insulative material having an array of openings configured to align with the array of microneedle structures on the substrate, such that the tip region and at least a distal portion of the body region of the microneedles pass through the array of openings of the sensor-cover component of the cover unit.

Example B77 includes the device of example B76 or any of examples B61-B82, wherein the sensor-cover component of the cover unit includes a sidewall that surrounds an interior region and is configured to encompass a side of the substrate when the cover unit is coupled with the substrate, and the cover unit includes a back-cover component that is configured to connect with the sidewall of the sensor-cover component and contact a backside of the substrate.

Example B78 includes the device of example B77 or any of examples B61-B82, wherein the cover unit further includes a holder having a peripheral sidewall that couples to the sidewall of the cover unit, the holder having an opening such that, when the holder is coupled to the sidewall of the microneedle sensor unit, the array of microneedle structures expand outward beyond the opening.

Example B79 includes the device of any of example B61-B78 or any of examples B61-B82, wherein the device is configured to be disposable after at least a first use by a user of the wearable, non-intrusive microneedle sensor device used to continuously monitor the target analyte.

Example B80 includes the device of any of examples B61-B82, wherein the target analyte includes one or more of a metabolite, electrolyte, protein, amino acid, nucleic acid, lipid, liposome, nanoparticle, or drug, and wherein at least one of the spiked microstructures includes a biological or chemical recognition element comprising one or more of an enzyme, an ionophore, an antibody, a peptide nucleic acid (PNA), a DNA aptamer, a RNA aptamer, or a cell.

Example B81 includes the device of any of examples B61-B82, wherein the device is configured to measure the target analyte in the biofluid, comprising any of a subdermal biological fluid that comprises an interstitial fluid, an extracellular fluid, a cerebrospinal fluid, or blood.

Example B82 includes the device of any of examples B61-B81, wherein the wearable, non-intrusive microneedle sensor patch device is configured to interface with an electronics unit in accordance with any of examples B1-B60.

In some example embodiments in accordance with the present technology (example B83), a method for fabricating a wearable, non-intrusive microneedle sensor device includes creating or obtaining a computer-aided design of a microneedle sensor array comprising a plurality of microneedle structures arranged on a substrate, wherein the plurality of microneedle structures includes a body region, a tip region, a protrusion that winds around at least an upper portion of the body region; producing a physical rendition of the microneedle sensor array, wherein at least some of the plurality of microneedle structures of the produced physical rendition of the microneedle sensor array include an electrically-conductive region to form microelectrodes of the at least some of the plurality of microneedle structures; and attaching a cover to the physical rendition of the microneedle sensor array, the cover comprising an electrically insulative material having a plurality of openings configured to align with the plurality of microneedle structures on the substrate, such that the tip region and at least a distal portion of the body region of the microneedle structures pass through the openings of the cover.

Example B84 includes the method of any of examples B83-B102, wherein the producing the physical rendition of the microneedle sensor array includes initiating a computer numeric control (CNC) machining process to run a programmed sequence of engraving steps and/or cutting steps to form a physical rendition of the microneedle sensor array.

Example B85 includes the method of example B84 or any of examples B83-B102, wherein the programmed sequence of engraving steps and/or cutting steps includes one or both of (i) utilizing drill bits ranging from 50 μm to 1 mm, and (ii) applying a spindle rate in a range of 500 to 25,000 rpm.

Example B86 includes the method of example B85 or any of examples B83-B102, wherein the programmed sequence of engraving steps and/or cutting steps includes one or both of (i) a step size ranging from 1 μm-1 mm, and (ii) implementing operations with parameters including one or more of [a] a spindle speed of 500 rpm to 12,000 rpm, [b] a surface speed of 40-120 m/min, [c] a plunge federate of 50-1,000 mm/min, [d] a feed per revolution of 0.01-0.1 mm, and/or [e] a retract federate of 50-1,000 mm/min.

Example B87 includes the method of example B85 or any of examples B83-B102, wherein the programmed sequence of engraving steps and/or cutting steps includes a finetuning micro-engraving process including a 2D or 3D adaptive or pocket strategy for an engraving step that includes using one or more of [a] a CNC bit flat 2-4 flute, [b] spindle rates of 500 to 15,000 rpm, and/or [c] a feed rate of 20-100 mm/min.

Example B88 includes the method of any of examples B83-B102, wherein the producing the physical rendition of the microneedle sensor array includes: creating a master structure for the microneedle sensor array, in accordance with the computer-aided design, that comprises a physical rendition of the plurality of microneedle structures arranged on a base; creating a mold based on the master structure for the microneedle sensor array; and casting at least one material in the created mold to form the physical rendition of array of microneedle sensor array.

Example B89 includes the method of example B88 or any of examples B83-B102, wherein the producing the master structuring for the microneedle sensor array includes initiating a computer numeric control (CNC) machining process to run a programmed sequence of engraving steps and/or cutting steps to form a physical model of the microneedle sensor array, or initiating a photolithography technique.

Example B90 includes the method of example B88 or any of examples B83-B102, wherein the master structure for the microneedle sensor array includes ultra-high resolution features of the microneedle structures, and wherein the producing the master structuring for the microneedle sensor array includes using a ultra-high resolution 3D printing technique, a computer numeric control (CNC) machining process, or a two-photon lithography technique.

Example B91 includes the method of example B88 or any of examples B83-B102, wherein the creating the mold includes depositing a molding material onto and/or into the master structure, degassing and heat treating the molding material on/in the master structure to produce the mold, and removing the master structure from the produced mold.

Example B92 includes the method of example B88 or any of examples B83-B102, wherein the casting includes depositing the at least one material that comprises a polymer material, and curing the polymer material to form the substrate and the plurality of microneedle structures arranged on the substrate.

Example B93 includes the method of any of examples B83-B102, wherein the producing the physical rendition of the microneedle sensor array includes: creating the substrate and the plurality of microneedle structures arranged on the substrate using a first material that is electrically insulative; and creating electrically conductive regions on the plurality of microneedle structures and the substrate to produce the microelectrodes and electrical interconnection lines, respectively.

Example B94 includes the method of example B93 or any of examples B83-B102, wherein the creating the electrically conductive regions includes: thin film-depositing an electrically conductive material onto particular portions of the microneedle structures to form a first coating; and etching at least a portion of the electrically conductive material on at least one of the microneedle structures to be designated as a working electrode and/or a counter electrode; and prepping at least a portion of the electrically conductive material on at least another one of the microneedle structures to be designated as a reference electrode.

Example B95 includes the method of examples B83-B102, further comprising: creating a base structure on a lower portion of the body region of the microneedle.

Example B96 includes the method of example B95 or any of examples B83-B102, wherein the creating the base structure includes: flowing a resin material through a plurality of microfluidic channels on a surface or below a surface of the substrate that are positioned proximate to a bottom portion of the body region of the microneedle structures, wherein the resin material flows through the microfluidic channels via capillary forces; and creating a sealed base structure on a lower portion of the body region of the microneedle structures by curing the resin material that flows upward on the lower portion of the body region.

Example B97 includes the method of example B96 or any of examples B83-B102, wherein the sealed base structure defines a sensing area including a non-covered portion of the body region of the microneedle structures for the physical rendition of the microneedle sensor array.

Example B98 includes the method of example B96 or any of examples B83-B102, wherein the resin material includes a polymer that is modified by a non-ionic surfactant and thermal treatment to render viscosity properties within a range of 0.01 to 0.5 Pa·s.

Example B99 includes the method of example B98 or any of examples B83-B102, wherein the resin material includes a biomedical grade polymer composed of a mixture of acrylate and methacrylate based monomers and oligomers and a benzil ketal compound as a photoinitiator.

Example B100 includes the method of example B99 or any of examples B83-B102, wherein the biomedical grade polymer has an initial viscosity of 5 Pa's that is lowered by the non-ionic surfactant via thermal treatment.

Example B101 includes the method of example B96 or any of examples B83-B102, wherein the resin material is configured to have resolution size lower than 500 nm.

Example B102 includes the method of example B96 or any of examples B83-B101, wherein the curing the resin material includes applying light energy to cause photo-crosslinking within the resin material to form a solid electrically insulative material to create the sealed base structure.

Example B103 includes the method of any of examples B83-B101, wherein the method is implemented on the device of any of examples B1-B82.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A wearable biosensor device, comprising:
a microneedle array comprising a substrate integral with microneedles at a top surface of the substrate, the microneedle array comprising an electrically insulative material and coated with an electrically conductive layer, wherein each of the microneedles comprises a tip region, a body region and a base, and wherein at least one of the microneedles is configured as a working electrode functionalized with at least one chemical layer on the electrically conductive layer to interact with analytes in a biofluid and configured to produce electrical signals associated with reactions detectable at the working electrode,
a cover unit fitted to the substrate, wherein the cover unit comprises first openings aligned so that at least a portion of the microneedles extends from the cover unit, and wherein microfluidic channels containing a custom cured resin are positioned on an inner surface of the cover unit or in or on the top surface of the substrate, the custom cured resin being an electrical insulator and also positioned as a base structure at the base of the microneedles thereby sealing the first openings and strengthening the microneedle array, and
an electronics unit positioned underneath the microneedle array and electrically connected thereto by a plurality of electrical interconnections.

2. The device of claim 1 wherein the microneedles are arranged into two or more sensing regions, wherein each of the sensing regions is configured to be separated electrically from the other sensing regions, each of the sensing regions comprising at least one of the working electrodes functionalized with a portion of the at least one chemical layer configured to interact with a different one of the analytes, so that each of the sensing regions is configured to produce the electrical signals associated with the reactions detectable at the working electrode.

3. The device of claim 2 wherein each of the sensing regions further comprises at least one reference electrode and at least one counter electrode.

4. The device of claim 1 wherein the microneedle array and the cover unit are configured to be disposable after at least a first use by a user of the wearable biosensor device used to continuously monitor the analytes, and wherein the electronics unit is configured to be reusable after at least the first use.

5. The device of claim 1 wherein the cover unit comprises second openings configured to feed a custom curable resin to the microfluidic channels to be photo-crosslinked in order to fill the microfluidic channels and to create the base structures.

6. The device of claim 1 wherein at least some of the microneedles comprise a cut-off line below which the base is wider than the body region in a configuration to assist in defining a height of the base structures reproducibly.

7. The device of claim 1, wherein the electronics unit comprises a data processing unit in communication with a signal processing circuit, the data processing unit comprising a processor and a memory and configured to process the electrical signal as data representative of one or more parameters of the analytes.

8. The device of claim 7, wherein the signal processing circuit is configured to process the electrical signals by one or more of amplifying the electrical signals, filtering the electrical signals, or converting the electrical signals from analog to digital, and wherein the data processing unit is configured to process the electrical signals after processing by the signal processing circuit.

9. The device of claim 1 wherein the cover unit comprises a sidewall surrounding an interior region and is configured to encompass a side of the substrate when the cover unit is coupled to the substrate.

10. The device of claim 9 wherein the cover unit further comprises a back-cover component that is configured to connect with the sidewall of the cover unit and contact a backside of the substrate.

11. The device of claim 9 wherein the cover unit further comprises a holder comprising a peripheral sidewall coupled to the sidewall of the cover unit.

12. The device of claim 11 wherein the holder comprises an opening such that, when the holder is coupled to a sidewall of the substrate, the microneedles expand outward beyond the first openings.

13. The device of claim 12 further comprising an outer casing configured to connect to the holder and encase the electronics unit and the microneedle array while exposing the microneedles from beyond the opening of the holder.

14. The device of claim 1 wherein the plurality of electrical interconnections comprises:

a plurality of electronic-connection holes in the substrate comprising at least one wall onto which the electrically conductive layer extends, and conductive pins comprising a first and second end, wherein the first end of each of the conductive pins is connected to the electronic-connection holes and the second end of each of the conductive pins is connected to the electronics unit.

15. The device of claim 14 wherein the electrically conductive layer is mechanically frictionous, and the first end of each of the conductive pins is connected to the electronic-connection holes by a friction fit.

16. The device of claim 1, wherein the analytes are selected from the group consisting of a metabolite, electrolyte, protein, amino acid, hormone, steroid, amine, nucleic acid, lipid, liposome, nanoparticle, and drug.

17. The device of claim 1, wherein the chemical layer comprises a material which is selected from the group consisting of an enzyme, an ionophore, an antibody, a peptide nucleic acid (PNA), a DNA aptamer, a RNA aptamer, a molecularly imprinted polymer (MIP), and a cell.

18. The device of claim 1, wherein the biofluid is selected from the group consisting of an interstitial fluid, an extracellular fluid, a cerebrospinal fluid, and blood.

* * * * *